US006458953B1

(12) United States Patent
Jones

(10) Patent No.: US 6,458,953 B1
(45) Date of Patent: Oct. 1, 2002

(54) VALENCY PLATFORM MOLECULES COMPRISING CARBAMATE LINKAGES

(75) Inventor: David S. Jones, San Diego, CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 0 days.

(21) Appl. No.: 09/457,607

(22) Filed: Dec. 8, 1999

Related U.S. Application Data
(60) Provisional application No. 60/111,641, filed on Dec. 9, 1998.

(51) Int. Cl.$^7$ .................. C07D 241/04; C07C 271/06
(52) U.S. Cl. .................. 544/357; 560/26; 560/115; 560/158; 530/402; 530/409
(58) Field of Search .................. 544/357; 560/26, 560/115, 158

(56) References Cited

U.S. PATENT DOCUMENTS

| | | | |
|---|---|---|---|
| 4,191,668 A | 3/1980 | Katz | 260/6 |
| 4,245,110 A | 1/1981 | Engelhard et al. | 560/160 |
| 4,751,181 A | 6/1988 | Keene | 435/70 |
| 4,987,130 A * | 1/1991 | Tsushima et al. | 514/210 |
| 5,126,131 A | 6/1992 | Dintzis et al. | 424/88 |
| 5,162,515 A | 11/1992 | Conrad et al. | 530/17 |
| 5,268,454 A | 12/1993 | Barstad et al. | 435/172.2 |
| 5,276,013 A | 1/1994 | Conrad et al. | 514/2 |
| 5,391,785 A | 2/1995 | Jones et al. | 552/105 |
| 5,552,391 A | 9/1996 | Coutts et al. | 514/44 |
| 5,606,047 A | 2/1997 | Coutts et al. | 536/26.1 |
| 5,663,395 A | 9/1997 | Göbel et al. | 556/427 |
| 5,726,329 A | 3/1998 | Jones et al. | 552/105 |
| 5,786,512 A | 7/1998 | Jones et al. | 568/22 |
| 6,022,544 A | 2/2000 | Dintzis et al. | 424/193.01 |
| 6,060,056 A | 5/2000 | Coutts et al. | 424/184.1 |

FOREIGN PATENT DOCUMENTS

| | | |
|---|---|---|
| DE | 24 12 217 A1 | 10/1975 |
| EP | 0 278 621 A1 | 8/1988 |
| EP | 0 438 259 | 7/1991 |
| EP | 0 442 724 | 8/1991 |
| EP | 0 523 978 | 1/1993 |
| EP | 0 642 798 | 3/1995 |
| WO | WO 87/00056 | 1/1987 |
| WO | WO 88/09810 | 12/1988 |
| WO | WO 91/10426 | 7/1991 |
| WO | WO 93/02093 | 2/1993 |
| WO | WO 95/07073 | 3/1995 |
| WO | WO 96/40197 | 12/1996 |
| WO | WO 97/46251 | 12/1997 |
| WO | WO 98/33528 | 8/1998 |
| WO | WO 98/47915 | 10/1998 |
| WO | WO 99/47494 A1 | 9/1999 |
| WO | WO 99/64595 A1 | 12/1999 |

OTHER PUBLICATIONS

Eisenbach, C. D. and Heinemann, T. (1995). "Thermoplastic Graft Copolymer Elastomers with Chain–Folding or Bifurcated Side Chains," *Macromol. Chem. Phys.* 196(8);2669–2686.

Eisenbach, C. D. and Heinemann, T. (Mar. 27, 1995). "Synthesis and Characterization of Thermoplastic Graft Copolymer Elastomers with a Polyether Main and Uniform Urethane–Based Side Chains," *Macromolecules* 28(7):2133–2139.

Lu, C. X. et al., (Jun. 1988). "Nucleic Acid Base Grafted Imino Grafted Imino Polyurethane," *J. Polymer Sci./Part A: Polymer Chem.*, John Wiley & Sons, Inc. (publisher), 26(6):1659–1669.

Bordunov et al. (1995) "Synthesis of new pyridinoazacrown ethers containing aromatic and heteroaromatic proton ionizable substituents" *J. Org. Chem.* 60:6097–6102.

Fischer et al. (1998) "Dendrimers: From design to application—a progress report" *Angew. Chem. Int. Ed.* 38:885–905.

Taylor et al. (1998) "Polyurethane dendrimers via Curtius reaction" *Tetrahedron Lett.* 39:8005–8008.

Jones, D.S. et al. (1994). "Conjugates of Double–Stranded Oligonucleotides with Poly(ethylene glycol) and Keyhole Limpet Hemocyanin: A Model for Treating Systemic Lupus Erythematosus," *Bioconjugate Chem.* 5:390–399.

Jones, D.S. et al. (1995). "Immunospecfic Reduction of Antioligonucleotide Antibody–Forming Cells with a Tetrakis–oligonucleotide Conjugate (LJP 394), a Therapeutic Candidate for the Treatment of Lupus Nephritis," *J. Med. Chem.* 38:2138–2144.

Sehon, A.H. (1991). "Suppression of Antibody Responses by Conjugates of Antigens and Monomethypoly(Ethylene Glycol)," *Advanced Drug Delivery Reviews* 6:203–217.

Efimov, V.A. et al. (1993). "Synthesis of Polyethylene Glycol–Oligonucleotide Conjugates," *Bioorg. Khim.*, 19(8):800–804 (English abstract on p. 804).

Hertler, A.A. (1988). "Human Immune Response to Immunotoxins," *Cancer Treatment Research* 37:475–480.

Galili et al. (1988) "Man, apes, and old world monkeys differ from other mammals in the expression of α–galactosyl epitopes on nucleated cells" *J. Biol. Chem.* 263:17755–17762.

Galili et al. (1998) "Anti–gal antibody prevents xenotransplantation" *Science and Medicine*.

* cited by examiner

*Primary Examiner*—Richard L. Raymond
(74) *Attorney, Agent, or Firm*—Morrison & Foerster LLP

(57) ABSTRACT

This invention pertains generally to valency molecules, such as valency platform molecules which act as scaffolds to which one or more molecules may be covalently tethered to form a conjugate. More particularly, the present invention pertains to valency platform molecules which comprise a carbamate linkage (i.e., —O—C(=O)—N<). In one aspect, the present invention pertains to valency platforms comprising carbamate linkages, which molecules have the structure of any one of Formulae I, II, or III, shown in FIG. 1. In one aspect, the present invention pertains to valency platforms comprising carbamate linkages, which molecules have the structure of any one of Formulae IV, V, or VI, shown in FIG. 8. The present invention also pertains to methods of preparing such valency platform molecules, conjugates comprising such valency platform molecules, and methods of preparing such conjugates.

37 Claims, 30 Drawing Sheets

Formula I

Formula II

Formula III

Formula I: n=1, y¹=1, Z=NR^A R^B

Formula I: n=2, y¹=1, Z=NR^A R^B

Formula I: $n=1$, $y^1=2$, $Z=NR^AR^B$

Formula I: $n=2$, $y^1=2$, $Z=NR^AR^B$

Formula II: $n=1$, $y^1=2$, $y^2=1$, $Z=NR^AR^B$

Formula II: $n=1$, $y^1=2$, $y^2=2$, $Z=NR^AR^B$

Formula II: $n=2$, $y^1=2$, $y^2=2$, $Z=NR^AR^B$

Formula IV: $n=2, y^1=2, y^2=2, y^3=2, Z=NR^AR^B$

Formula IV

Formula V

Formula VI

39b

39c

VALENCY PLATFORM MOLECULES COMPRISING CARBAMATE LINKAGES

RELATED APPLICATIONS

This application claims the priority benefit of provisional application U.S. Ser. No. 60/111,641, filed Dec. 9, 1998, the contents of which are incorporated herein in their entirety.

TECHNICAL FIELD

This invention pertains generally to valency molecules. The invention also relates to the field of valency platform molecules which act as scaffolds to which one or more molecules may be covalently tethered to form a conjugate. More particularly, the present invention pertains to valency molecules which comprise a carbamate linkage (i.e., —O—C(=O)—N<). In one aspect, the present invention pertains to valency platforms comprising carbamate linkages, which molecules have the structure of any one of Formulae I, II, or III, shown in FIG. 1. In one aspect, the present invention pertains to valency platforms comprising carbamate linkages, which molecules have the structure of any one of Formulae IV, V, or VI, shown in FIG. 8. The present invention also pertains to methods of preparing such valency molecules, conjugates comprising such valency molecules, and methods of preparing such conjugates.

BACKGROUND

A "valency platform" is a molecule with one or more (and typically multiple) attachment sites which can be used to covalently attach biologically active molecules of interest to a common scaffold. The attachment of biologically active molecules to a common scaffold provides multivalent conjugates in which multiple copies of the biologically active molecule are covalently linked to the same platform. A "defined" or "chemically defined" valency platform is a platform with defined structure, thus a defined number of attachment points and a defined valency. A defined valency platform conjugate is a conjugate with defined structure and has a defined number of attached biologically active compounds. Examples of biologically active molecules include oligonucleotides, peptides, polypeptides, proteins, antibodies, saccharides, polysaccharides, epitopes, mimotopes, drugs, and the like. In general, biologically active compounds interact specifically with proteinaceous receptors.

Certain classes of chemically defined valency platforms, methods for their preparation, conjugates comprising them, and methods for the preparation of such conjugates, have been described in the U.S. Pat. Nos. 5,162,515; 5,391,785; 5,276,013; 5,786,512; 5,726,329; 5,268,454; 5,552,391; 5,606,047; and 5,663,395.

The valency platforms of the present invention reflect a new class of valency platforms which comprise a carbamate linkage, as shown, for example, in Formulae I, II, and III in FIG. 1 and in Formulae IV, V, and VI in FIG. 8.

SUMMARY OF THE INVENTION

One aspect of the present invention pertains to a valency platform compound having the structure of one of the following formulae:

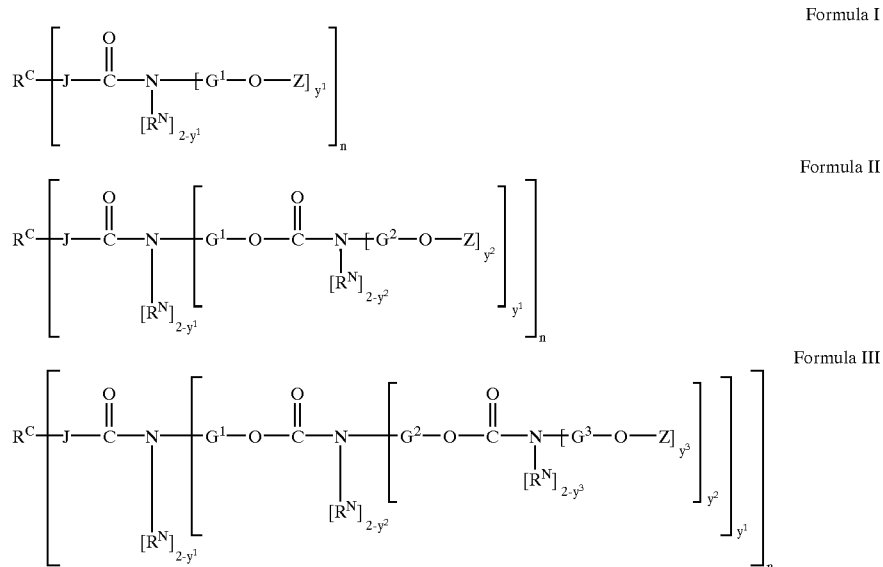

wherein:
- n is a positive integer from 1 to 10;
- $y^1$, $y^2$, and $y^3$ are independently 1 or 2;
- J independently denotes either an oxygen atom or a covalent bond;
- $R^C$ is selected from the group consisting of:
  - hydrocarbyl groups having from 1 to 20 carbon atoms;
  - organic groups consisting only of carbon, oxygen, and hydrogen atoms, and having from 1 to 20 carbon atoms;
  - organic groups consisting only of carbon, oxygen, nitrogen, and hydrogen atoms, and having from 1 to 20 carbon atoms;
  - organic groups consisting only of carbon, oxygen, sulfur, and hydrogen atoms, and having from 1 to 20 carbon atoms;
- each $G^1$, $G^2$, and $G^3$ is independently selected from the group consisting of:

hydrocarbyl groups having from 1 to 20 carbon atoms;
organic groups consisting only of carbon, oxygen, and hydrogen atoms, and having from 1 to 20 carbon atoms;
organic groups consisting only of carbon, oxygen, nitrogen, and hydrogen atoms, and having from 1 to 20 carbon atoms;

each $R^N$ is independently selected from the group consisting of: hydrogen;
linear or branched alkyl groups having from 1 to 15 carbon atoms;
alkyl groups comprising an alicyclic structure and having from 1 to 15 carbon atoms;
aromatic groups having from 6 to 20 carbon atoms;
heteroaromatic groups having from 3 to 20 carbon atoms;

each Z is independently selected from the group consisting of:
—H
—C(=O)OR$^{CARB}$
—C(=O)R$^{ESTER}$
—C(=O)NR$^A$R$^B$ wherein:

each R$^{CARB}$ is organic groups comprising from 1 to about 20 carbon atoms;

each R$^{ESTER}$ is organic groups comprising from 1 to about 20 carbon atoms;

each group —NR$^A$R$^B$ is independently selected from the group consisting of:
—NH$_2$
—NHR$^A$
—NR$^A$R$^B$
—NR$^{AB}$ wherein each monovalent R$^A$ and R$^B$ and each divalent R$^{AB}$ is independently an organic group comprising from 1 to 20 carbon atoms, and further comprising a reactive conjugating functional group.

In one embodiment, said compound has the structure of Formula I. In one embodiment, said compound has the structure of Formula II. In one embodiment, said compound has the structure of Formula III. In one embodiment, said compound has the structure of Formula IV. In one embodiment, n is a positive integer from 2 to 4. In one embodiment, $y^1$, $y^2$, and $y^3$ are each 2. In one embodiment, J is an oxygen atom. In one embodiment, J is a covalent bond. In one embodiment, R$^C$ is selected from the group consisting of hydrocarbyl groups having from 1 to 20 carbon atoms. In one embodiment, R$^C$ is selected from the group consisting of:

—CH$_2$—;

—CH$_2$CH$_2$—;

—CH$_2$CH$_2$CH$_2$—;

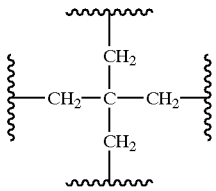 ; and

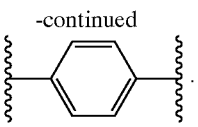

In one embodiment, R$^C$ is selected from the group consisting of organic groups consisting only of carbon, oxygen, and hydrogen atoms, and having from 1 to 20 carbon atoms. In one embodiment, R$^C$ is:

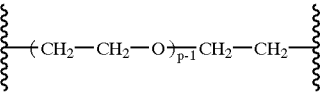

wherein p is a positive integer from 2 to 20. In one embodiment, each G$^1$, G$^2$, and G$^3$ is independently selected from the group consisting of hydrocarbyl groups having from 1 to 20 carbon atoms. In one embodiment, each G$^1$, G$^2$, and G$^3$ is —(CH$_2$)$_q$— wherein q is a positive integer from 1 to 20. In one embodiment, each G$^1$, G$^2$, and G$^3$ is independently selected from the group consisting of organic groups consisting only of carbon, oxygen, and hydrogen atoms, and having from 1 to 20 carbon atoms. In one embodiment, each G$^1$, G$^2$, and G$^3$ is:

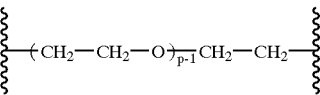

wherein p is a positive integer from 2 to 20. In one embodiment, R$^N$ is independently selected from the group consisting of —H, —CH$_3$, and —CH$_2$CH$_3$. In one embodiment, each group —NR$^A$R$^B$ is independently selected from the group consisting of:

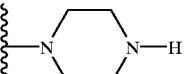

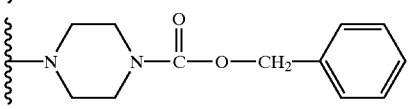

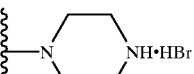

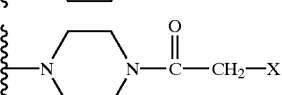

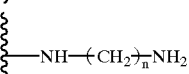

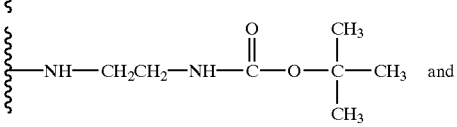 and

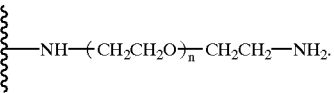

Another aspect of the present invention pertains to a valency platform compound having the structure of one of the following formulae:

Formula IV $$R^C\left[J-\overset{O}{\underset{\underset{R^N}{|}}{C}}-N-G^1-[O-Z]_{y^1}\right]_n$$

Formula V $$R^C\left[J-\overset{O}{\underset{\underset{R^N}{|}}{C}}-N-G^1-\left[O-\overset{O}{\underset{\underset{R^N}{|}}{C}}-N-G^2-[O-Z]_{y^2}\right]_{y^1}\right]_n$$

Formula VI $$R^C\left[J-\overset{O}{\underset{\underset{R^N}{|}}{C}}-N-G^1-\left[O-\overset{O}{\underset{\underset{R^N}{|}}{C}}-N-G^2-\left[O-\overset{O}{\underset{\underset{R^N}{|}}{C}}-N-G^3-[O-Z]_{y^3}\right]_{y^2}\right]_{y^1}\right]_n$$

wherein:
n is a positive integer from 1 to 10;
$y^1$, $y^2$, and $y^3$ are independently a positive integer from 1 to 10;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
  organic groups consisting only of carbon, oxygen, sulfur, and hydrogen atoms, and having from 1 to 20 carbon atoms;
each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
each $R^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms;
  heteroaromatic groups having from 3 to 20 carbon atoms;
each Z is independently selected from the group consisting of:
  —H
  —C(=O)OR$^{CARB}$
  —C(=O)R$^{ESTER}$
  —C(=O)NR$^A$R$^B$
wherein:
  each R$^{CARB}$ is organic groups comprising from 1 to about 20 carbon atoms;

each R$^{ESTER}$ is organic groups comprising from 1 to about 20 carbon atoms;
  each group —NR$^A$R$^B$ is independently selected from the group consisting of:
    —NH$_2$
    —NHR$^A$
    —NR$^A$R$^B$
    —NR$^{AB}$
  wherein each monovalent R$^A$ and R$^B$ and each divalent R$^{AB}$ is independently an organic group comprising from 1 to 20 carbon atoms, and further comprising a reactive conjugating functional group.

In one embodiment, said compound has the structure of Formula V. In one embodiment, said compound has the structure of Formula VI. In one embodiment, said compound has the structure of Formula VII. In one embodiment, n is a positive integer from 2 to 4. In one embodiment, $y^1$, $y^2$, and $y^3$ are each 2. In one embodiment, J is an oxygen atom. In one embodiment, J is a covalent bond. In one embodiment, RC is selected from the group consisting of hydrocarbyl groups having from 1 to 20 carbon atoms. In one embodiment, $R^C$ is selected from the group consisting of:

—CH$_2$—;

—CH$_2$CH$_2$—;

—CH$_2$CH$_2$CH$_2$—;

$$-CH_2-\underset{\underset{CH_2}{|}}{\overset{\overset{CH_2}{|}}{C}}-CH_2-\text{; and}$$

$$-\!\!\!\left\langle\!\!\!\begin{array}{c}\phantom{x}\\\phantom{x}\end{array}\!\!\!\right\rangle\!\!\!-.$$

In one embodiment, $R^C$ is selected from the group consisting of organic groups consisting only of carbon, oxygen, and hydrogen atoms, and having from 1 to 20 carbon atoms. In one embodiment, $R^C$ is:

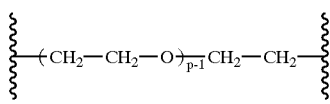

wherein p is a positive integer from 2 to 20. In one embodiment, each $G^1$, $G^2$, and $G^3$ is independently selected from the group consisting of hydrocarbyl groups having from 1 to 20 carbon atoms. In one embodiment, each $G^1$, $G^2$, and $G^3$ is selected from the group consisting of:

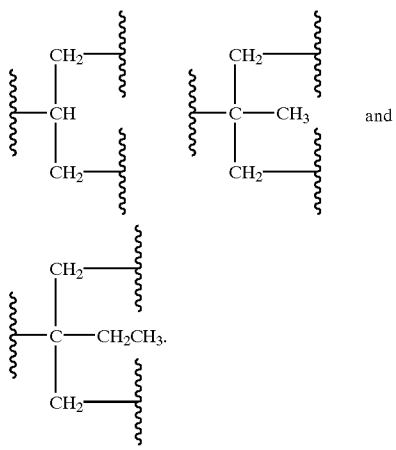

In one embodiment, each $G^1$, $G^2$, and $G^3$ is independently selected from the group consisting of organic groups consisting only of carbon, oxygen, and hydrogen atoms, and having from 1 to 20 carbon atoms. In one embodiment, each $R^N$ is independently selected from the group consisting of —H, —CH$_3$, and —CH$_2$CH$_3$. In one embodiment, each group —NR$^A$R$^B$ is independently selected from the group consisting of:

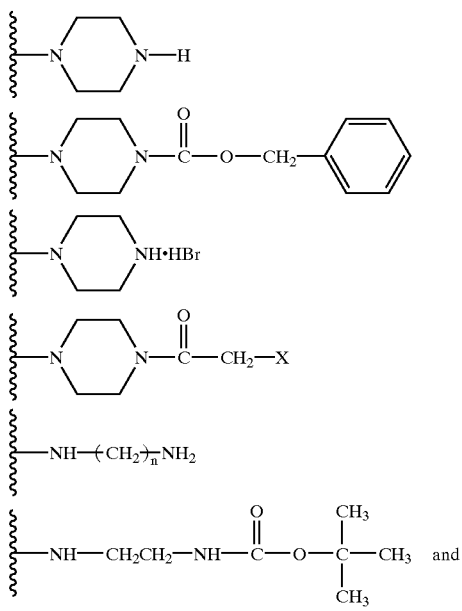

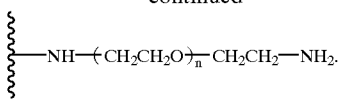

Another aspect of the present invention pertains to methods of preparing a valency platform compound, as described herein.

Another aspect of the present invention pertains to a conjugate comprising a valency platform compound, as described herein, covalently linked to one or more biologically active molecules. In one embodiment, said biologically active molecules are selected from the group consisting of: oligonucleotides, peptides, polypeptides, proteins, antibodies, saccharides, polysaccharides, epitopes, mimotopes, and drugs.

Another aspect of the present invention pertains to methods of preparing conjugates, as described herein.

As will be appreciated by one of skill in the art, features of one aspect or embodiment of the invention are also applicable to other aspects or embodiments of the invention.

DETAILED DESCRIPTION OF THE INVENTION

Figure 1:
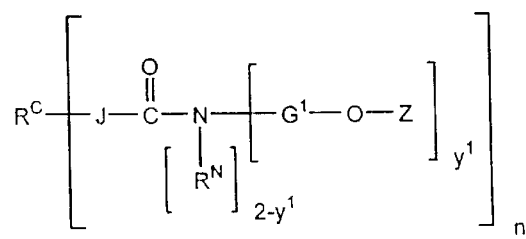
FIG. 1 shows certain valency platforms of the present invention, specifically, those having the structure of Formulae I, II, and III.
Figure 1:
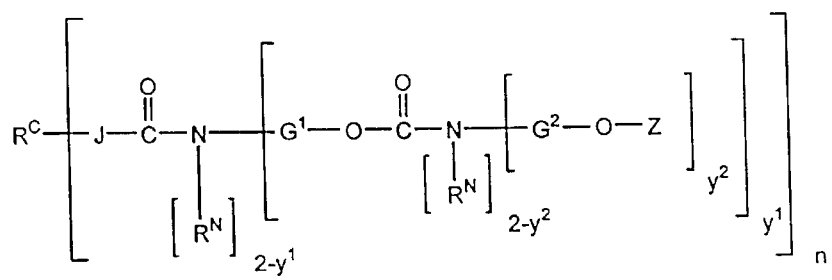
Figure 1:
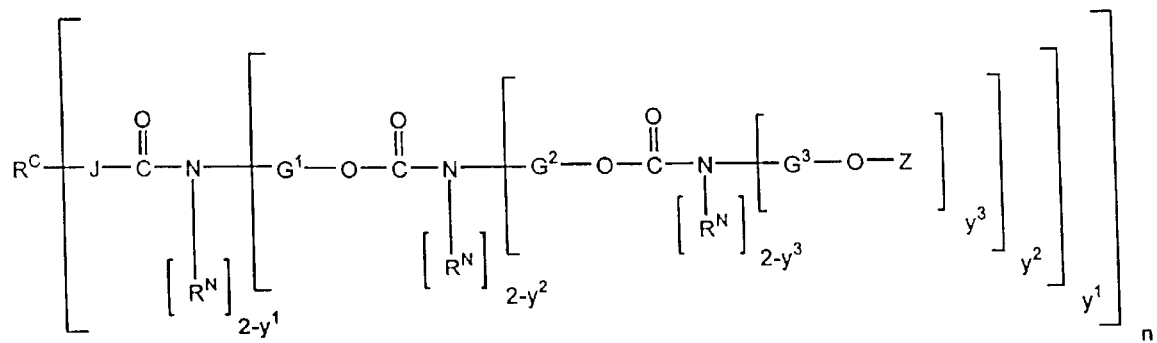

Throughout this application, various publications, patents, and published patent applications are referred to by an identifying citation. The disclosures of the publications, patents, and published patent specifications referenced in this application are hereby incorporated by reference into the present disclosure in their entirety.

In one embodiment, valency molecules are provided that comprise branches, wherein at each branch, the molecule branches into two or more arms. The arms also may comprise branches. The valency molecule further comprises terminal groups on arms extending from the branches. Exemplary terminal groups are reactive conjugating functional groups. This is illustrated in the Figures, for example, by compound 14 in FIG. 11B, which includes 6 branches and 8 terminal CBZ-protected amino groups.

Thus, in one embodiment, provided is a composition comprising valency molecules, wherein each valency molecule comprises at least two branches, at least four terminal groups, and at least 2 carbamate linkages; and wherein said valency molecules have a polydispersity less than about 1.2, or for example, less than about 1.07. The valency molecules further can comprise, for example, at least 4 carbamate linkages, at least 4 branches and at least 8 terminal groups. The valency molecules may be dendrimers.

The number of branches in the valency molecule may vary and may be, for example, 2, 3, 4, 5, 6, 8, 9, 10, 11, 12, 16, 32, 64, 100 or more branches. The number of branches can be, for example, 2–64, 2–32, 2–16, 4–64, 4–32, 8–64, or 8–32. In a further embodiment, the number of branches may be, for example, at least 2, at least 4, at least 6, or at least 8.

The number of carbamate linkages may vary. The valency molecule can include, for example, 2, 3, 4, 5, 6, 8, 9, 10, 11, 12, 15, 16, 18, 20, 24, 29, 32, 64, 100 or more carbamate linkages. The number of carbamate linkages can be, for example, 2–64, 2–32, 2–16, 4–64, 4–32, 8–64, or 8–32. In a further embodiment, the number of carbamate linkages may be, for example, at least 2, at least 4, at least 6, or at least 8.

Each valency molecule can comprise for example, 1 to 100, e.g, 1–50 terminal groups. For example, the valency molecule may comprise 4, 6, 8, 9, 10, 12, 14, 15, 16, 18, 20, 21, 24, 29, or 32 or more terminal groups. The valency molecule, for example, may comprise at least 4 terminal groups, or at least 6 terminal groups, or at least 8 terminal groups. The valency molecule in one embodiment has, for example, 4–16, 4–32, 4–64, 8–32, 8–64, 12–32 or 12–64 terminal groups. The said terminal groups are in one embodiment identical.

Examples of valency molecules include valency platform molecules. Valency molecules can be made as described herein for the synthesis of valency platform molecules.

A. Valency Platforms

In one aspect, the present invention pertains to valency platforms comprising carbamate linkages and methods for the preparation of such platforms.

Particular advantages of the present invention include, but are not limited to, (1) the ease of synthesis of valency platform molecules, (2) the metabolic stability of the carbamate linkages in the valency platform, (3) the ability to adjust the length and water solubility of the "arms" of the valency platform by using, for example, different dialcoholamines, (4) the ability to further attenuate the properties of the valency platform by choice of the core group (e.g., attachment of solubilizing groups, chromophores, reporting groups, targeting groups, and the like).

In one embodiment, a composition is provided comprising valency platform molecules, wherein each valency platform molecule comprises at least 2 carbamate linkages and at least 4 reactive conjugating functional groups; and wherein said valency platform molecules have a polydispersity less than about 1.2, or optionally a polydispersity less than about 1.07. The valency platform molecules of the composition may comprise, for example, at least 4 carbamate linkages and at least 8 reactive functional groups. In one embodiment, the valency platform molecules comprise at least 4 identical reactive conjugating functional groups. In another embodiment, the valency platform molecules comprise, for example, 2–32 carbamate linkages and 4–64 reactive functional groups. The valency platform molecules optionally may be linked to one or more biologically active molecules, e.g., via the reactive conjugating functional groups.

The valency molecules, such as valency platform molecules have the advantage of having a substantially homogeneous (i.e., uniform) molecular weight (as opposed to polydisperse molecular weight), and are thus "chemically defined". Accordingly, a population of these molecules (or conjugates thereof) are substantially monodisperse, i.e., have a narrow molecular weight distribution. A measure of the breadth of distribution of molecular weight of a sample of a platform molecule (such as a composition and/or population of platform molecules) is the polydispersity of the sample. Polydispersity is used as a measure of the molecular weight homogeneity or nonhomogeneity of a polymer sample. Polydispersity is calculated by dividing the weight average molecular weight (Mw) by the number average molecular weight (Mn). The value of Mw/Mn is unity for a perfectly monodisperse polymer. Polydispersity (Mw/Mn) is measured by methods available in the art, such as gel permeation chromatography. The polydispersity (Mw/Mn) of a sample of valency molecules is preferably less than 2, more preferably, less than 1.5, or less than 1.2, less than 1.1, less than 1.07, less than 1.02, or, e.g., about 1.05 to 1.5 or about 1.05 to 1.2. Typical polymers generally have a polydispersity of 2–5, or in some cases, 20 or more. Advantages of the low polydispersity property of the valency platform molecules include improved biocompatibility and bioavailability since the molecules are substantially homogeneous in size, and variations in biological activity due to wide variations in molecular weight are minimized. The low polydispersity molecules thus are pharmaceutically optimally formulated and easy to analyze.

Further there is controlled valency in a population of the valency molecules. Thus, in a population of valency platform molecules, for example, the number of attachment sites, e.g., reactive conjugating functional groups, is controlled and defined. Each valency platform molecule can comprise for example, 1 to 100, e.g, 1–50 attachment sites. For example, the valency platform molecule may comprise 4, 6, 8, 9, 10, 12, 14, 15, 16, 18, 20, 21, 24, 29, or 32 or more attachment sites. The valency platform molecule, for example, may comprise at least 4 attachment sites, or at least 6 attachment sites, or at least 8 attachment sites. The valency platform molecule in one embodiment has, for example, 4–16, 4–32, 4–64, 8–32, 8–64, 12–32 or 12–64 attachment sites. The said attachment sites are in one preferred embodiment identical.

The number of carbamate linkages may vary. The valency platform molecule can include, for example, 2, 3, 4, 5, 6, 8, 9, 10, 11, 12, 15, 16, 18, 20, 24, 29, 32, 64, 100 or more carbamate linkages. The number of carbamate linkages can be, for example, 2–64, 2–32, 2–16, 4–64, 4–32, 8–64, or 8–32. In a further embodiment, the number of carbamate linkages may be, for example, at least 2, at least 4, at least 6, or at least 8.

The valency platform molecule can comprise various combinations of the carbamate linkages and attachment sites such as reactive functional groups depending on the method of preparation, for example, 2–32, e.g., 2–16 carbamate linkages; and 4–64, e.g., 4–32 reactive functional groups.

Formula I

In one embodiment, the present invention pertains to a valency platform having the structure of Formula I, as shown in FIG. 1.

Formula I

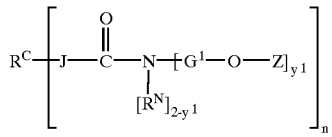

In Formula I, n is a positive integer from 1 to 10, more preferably from 1 to 5. In one embodiment, n is a positive integer from 2 to 10, more preferably from 2 to 5. In one embodiment, n is 1. In one embodiment, n is 2. In one embodiment, n is 3. In one embodiment, n is 4.

In Formula I, $y^1$ is 1 or 2, and the subscript "$2-y^1$" is therefore 1 or 0, respectively.

In Formula I, J independently denotes either an oxygen atom (i.e., —O—) or a covalent bond (i.e., no atom is present). When J is —O—, $R^C$ is bound to the corresponding sidechain via a carbamate linkage (i. e., —O—C(=O)—N<). When J is a covalent bond, $R^C$ is bound to the corresponding sidechain via an amide linkage (i.e., —C(=O)—N<).

In Formula I, $R^C$ denotes a "core group," that is, an organic group which forms the core of the valency platform, and to which one or more sidechains is attached. The valency of the core group is determined by n. If n is 1, then $R^C$ is monovalent; if n is 2, then $R^C$ is divalent; if n is 3, then $R^C$ is trivalent; if n is 4, then $R^C$ is tetravalent, and so on.

In one embodiment, $R^C$ is a hydrocarbyl group (i. e., consisting only of carbon and hydrogen) having from 1 to 20 carbon atoms, more preferably from 1 to 10 carbon atoms, still more preferably from 1 to 6 carbon atoms. In one embodiment, $R^C$ is linear. In one embodiment, $R^C$ is branched. In one embodiment, $R^C$ comprises a cyclic structure. In one embodiment, $R^C$ is cyclic. In one embodiment, $R^C$ is fully saturated. In one embodiment, $R_C$ is partially unsaturated. In one embodiment, $R^C$ comprises an aromatic structure. In one embodiment, $R^C$ is aromatic. In one embodiment, $R^C$ is —CH$_2$—. In one embodiment, $R^C$ is —CH$_2$CH$_2$—. In one embodiment, $R^C$ is —CH$_2$CH$_2$CH$_2$—. In one embodiment, $R^C$ is:

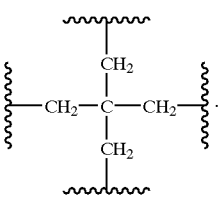

In one embodiment, $R^C$ is:

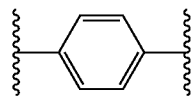

In one embodiment, $R^C$ is an organic group consisting only of carbon, oxygen, and hydrogen atoms, and having from 1 to 20 carbon atoms, more preferably from 1 to 10 carbon atoms, still more preferably from 1 to 6 carbon atoms. In one embodiment, $R^C$ is derived from a polyalkylene oxide group. In one embodiment, $R^C$ is derived from a polyethylene oxide group. In one embodiment, $R^C$ is a divalent polyalkylene oxide group. In one embodiment, $R^C$ is a divalent polyethylene oxide group. In one embodiment, $R^C$ is a divalent polypropylene oxide group. In one embodiment, $R^C$ is:

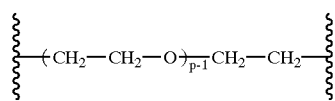

wherein p is a positive integer from 2 to about 200, more preferably from 2 to about 50, more preferably from 2 to about 20, more preferably from 2 to about 10, more preferably from 2 to about 6. In one embodiment, p is 2. In one embodiment, p is 3. In one embodiment, p is 4. In one embodiment, p is 5. In one embodiment, p is 6.

In one embodiment, $R^C$ is an organic group consisting only of carbon, oxygen, nitrogen, and hydrogen atoms, and having from 1 to 20 carbon atoms, more preferably from 1 to 10 carbon atoms, still more preferably from 1 to 6 carbon atoms. Examples of such core groups include, but are not limited to, those derive from the "core compounds" described below which consist only of carbon, oxygen, nitrogen, and hydrogen atoms.

In one embodiment, $R^C$ is an organic group consisting only of carbon, oxygen, sulfur, and hydrogen atoms, and having from 1 to 20 carbon atoms, more preferably from 1 to 10 carbon atoms, still more preferably from 1 to 6 carbon atoms. Examples of such core groups include, but are not limited to, those derive from the "core compounds" described below which consist only of carbon, oxygen, sulfur, and hydrogen atoms.

In Formula I, $G^1$ denotes an organic "linker group." In one embodiment, $G^1$ is a hydrocarbyl group (i.e., consisting only of carbon and hydrogen) having from 1 to 20 carbon atoms, more preferably from 1 to 10 carbon atoms, still more preferably from 1 to 6 carbon atoms. In one embodiment, $G^1$ is linear. In one embodiment, $G^1$ is branched. In one embodiment, $G^1$ comprises a cyclic structure. In one embodiment, $G^1$ is cyclic. In one embodiment, $G^1$ is fully saturated. In one embodiment, $G^1$ is partially unsaturated. In one embodiment, $G^1$ comprises an aromatic structure. In one embodiment, $G^1$ is aromatic. In one embodiment, $G^1$ is divalent. In one embodiment, $R^C$ is —$(CH_2)_q$— wherein q is a positive integer from 1 to about 20, more preferably from 1 to about 10, more preferably from 1 to about 6, more preferably from 1 to about 4. In one embodiment, $G^1$ is —$CH_2$—. In one embodiment, $G^1$ is —$CH_2CH_2$—. In one embodiment, $G^1$ is —$CH_2CH_2CH_2$—.

In one embodiment, $G^1$ is an organic group consisting only of carbon, oxygen, and hydrogen atoms, and having from 1 to 20 carbon atoms, more preferably from 1 to 10 carbon atoms, still more preferably from 1 to 6 carbon atoms. In one embodiment, $G^1$ is derived from a polyalkylene oxide group. In one embodiment, $G^1$ is a divalent polyalkylene oxide group. In one embodiment, $G^1$ is a divalent polyethylene oxide group. In one embodiment, $G^1$ is a divalent polypropylene oxide group. In one embodiment, $G^1$ is:

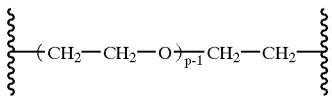

wherein p is a positive integer from 2 to about 200, more preferably from 2 to about 50, more preferably from 2 to about 20, more preferably from 2 to about 10, more preferably from 2 to about 6. In one embodiment, p is 2. In one embodiment, p is 3. In one embodiment, p is 4. In one embodiment, p is 5. In one embodiment, p is 6.

In one embodiment, $G^1$ is an organic group consisting only of carbon, oxygen, nitrogen, and hydrogen atoms, and having from 1 to 20 carbon atoms, more preferably from 1 to 10 carbon atoms, still more preferably from 1 to 6 carbon atoms.

In Formula I, $R^N$ denotes a nitrogen substituent, more specifically, an amino substituent. In one embodiment $R^N$, if present, is hydrogen (i.e., —H). In one embodiment, $R^N$, if present, is a linear or branched alkyl group having from 1 to 15 carbon atoms, more preferably from 1 to 10 carbon atoms, more preferably from 1 to 6 carbon atoms. In one embodiment, $R^N$, if present, is an alkyl group comprising an alicyclic structure and having from 1 to 15 carbon atoms, more preferably from 1 to 10 carbon atoms, more preferably from 1 to 6 carbon atoms. In one embodiment, $R^N$, if present, is or comprises an aromatic group. In one embodiment, $R^N$, if present, is or comprises a heteroaromatic group. In one embodiment, $R^N$, if present, is or comprises an aromatic group having from 6 to 20 carbon atoms, more preferably from 6 to 15 carbon atoms, more preferably from 6 to 10 carbon atoms. In one embodiment, $R^N$, if present, is or comprises a heteroaromatic group having from 3 to 20 carbon atoms, more preferably from 3 to 15 carbon atoms, more preferably from 3 to 10 carbon atoms. In one embodiment, $R^N$ is selected from the group consisting of —H, —$CH_3$, and —$CH_2CH_3$.

In Formula I, Z denotes a terminal group, which is independently selected from the group consisting of: —H (which yields a terminal alcohol group), —$C(=O)OR^{CARB}$ (which yields a terminal carbonate group), —$C(=O)R^{ESTER}$ (which yield a terminal ester group), and —$C(=O)NR^AR^B$ (which yields a terminal carbamate group).

In the above formulae, each $R^{CARB}$ is a carbonate substituent or an activated carbonate substituent. Many carbonate substituents are well known in the art, including, for example, organic groups comprising from 1 to about 20 carbon atoms, including, for example, primary, secondary, and tertiary, substituted and unsubstituted, alkyl and aryl groups having from 1 to about 20 carbon atoms. Other examples of carbonate groups include those described herein for $R^N$. Still other examples of carbonate groups include those described below for activated carbonates.

In the above formulae, each $R^{ESTER}$ is an ester substituent or an activated ester substituent. Many ester and activated ester substituents are well known in the art, including, for example, organic groups comprising from 1 to about 20 carbon atoms, including, for example, primary, secondary, and tertiary alkyl and aryl groups having from 1 to about 20 carbon atoms. Other examples of carbonate groups include those described herein for $R^N$. Examples of $R^{ESTER}$ include, but are not limited to, —$CH_3$ (to give an acetate group), —$CH_2SH$ (to give a mercaptoacetate group), and —$CH_2C_6H_5$, to give a benzoate group).

In one embodiment, Z is —$NR^AR^B$ and denotes an amino group. The amino group may be unsubstituted, in which case, $R^A$ and $R^B$ are both hydrogen (i.e., —$NR^AR^B$ is —$NH_2$). The amino group may be monosubstituted, in which case $R^B$ is hydrogen (i.e., —$NR^AR^B$ is —$NHR^A$). The amino group may be disubstituted. In this case, $R^A$ and $R^B$ may be separate moieties, as in —$NR^AR^B$, or $R^A$ and $R^B$ may be covalently linked together and form a divalent substituent, denoted $R^{AB}$ (i.e., —$NR^AR^B$ is —$NR^{AB}$). Thus, in one embodiment, each group —$NR^AR^B$ is independently selected from the group consisting of: —$NH_2$, —$NHR^A$, —$NHR^AR^B$, and —$NR^{AB}$, wherein each monovalent $R^A$ and $R^B$ and each divalent $R^{AB}$ is independently an organic group comprising from 1 to 20 carbon atoms, and further comprising a reactive conjugating functional group. In one embodiment, each group —$NR^AR^B$ is independently selected from the group consisting of: —$NHR^A$, —$NHR^AR^B$, and —$NR^{AB}$. When not hydrogen, $R^A$, $R^B$, and $R^{AB}$, preferably comprise a reactive conjugating functional group.

The term "reactive conjugating functional group" is used herein to refer to reactive functional groups which facilitate conjugation, for example, with a biologically active molecule. Examples of such reactive conjugating functional groups include, but are not limited to, the following:

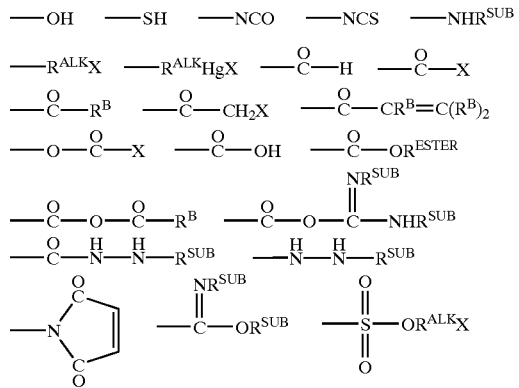

-continued

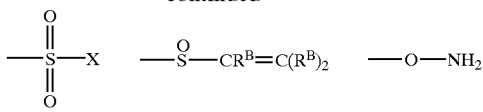

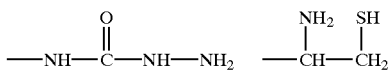

In the above reactive conjugating functional groups, each X is independently F, Cl, Br, I, or other good leaving group; each $R^{ALK}$ is independently an alkyl group, such as a linear or branched alkyl or cycloalkyl group having from 1 to about 20 carbon atoms; each $R^{SUB}$ is independently H or an organic group, such as a linear or branched alkyl group, or a cycloalkyl group having from 1 to about 20 carbon atoms, an aryl group having from 6 to about 20 carbon atoms, or an alkaryl group having from 7 to about 30 carbon atoms; each $R^{ESTER}$ is independently an organic group having from 1 to about 20 carbon atoms, including, for example, primary, secondary, and tertiary alkyl and aryl groups having from 1 to about 20 carbon atoms; and, each $R^B$ is independently a organic group, such as an organic group comprising 1 to 50 atoms selected from the group consisting of C, H, N, O, Si, P, and S.

In a preferred embodiment, the reactive conjugating functional group is an amino group or a protected amino group. In one embodiment, the group —$NR^AR^B$ comprises an amino group, and has the structure:

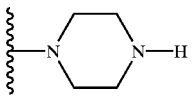

In one embodiment, the group —$NR^AR^B$ comprises a protected amino group, and has the structure:

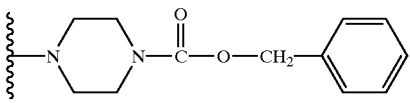

which is often conveniently abbreviated using "CBZ" to denote "carbobenzyloxy":

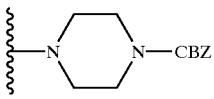

In one embodiment, the group —$NR^AR^B$ comprises a hydrobromide salt of an amino group, and has the structure:

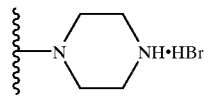

In one embodiment, the group —$NR^AR^B$ comprises a haloacetyl group (where X denotes Cl, Br, or I), and has the structure:

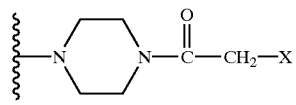

In one embodiment, the group —$NR^AR^B$ comprises an amino group, and has the structure:

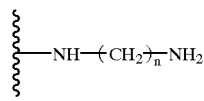

wherein n is a positive integer from 1 to about 20, preferably from 1 to about 10, preferably from 1 to about 5. In one embodiment, the group —$NR^AR^B$ comprises a protected amino group, and has the structure:

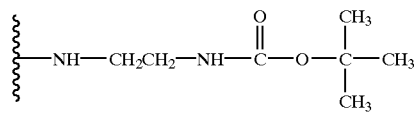

which is often conveniently abbreviated using "BOC" to denote "tert-butoxycarbonyl":

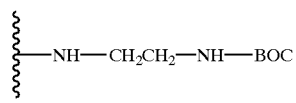

In one embodiment, the group —$NR^AR^B$ comprises an amino group, and has the structure:

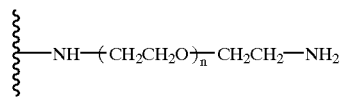

wherein n is a positive integer from 1 to about 20, preferably from 1 to about 10, preferably from 1 to about 5.

Figure 2:
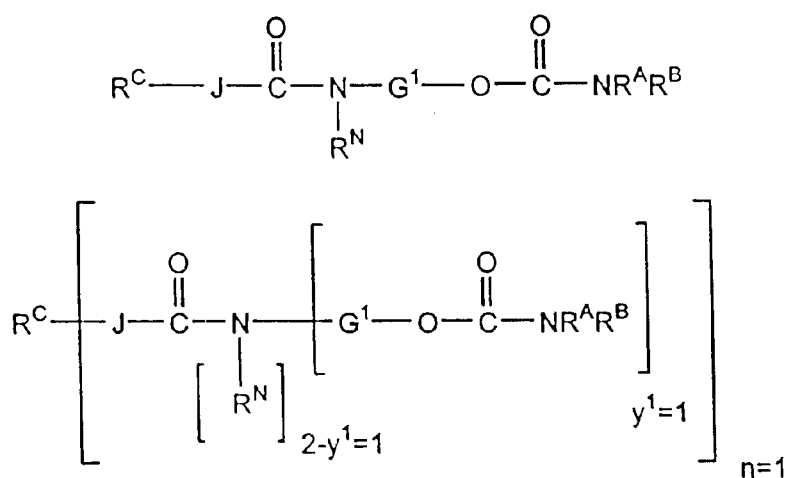
FIG. 2 shows certain valency platforms of the present invention, specifically, some of those having the structure of Formula I.
Figure 2:
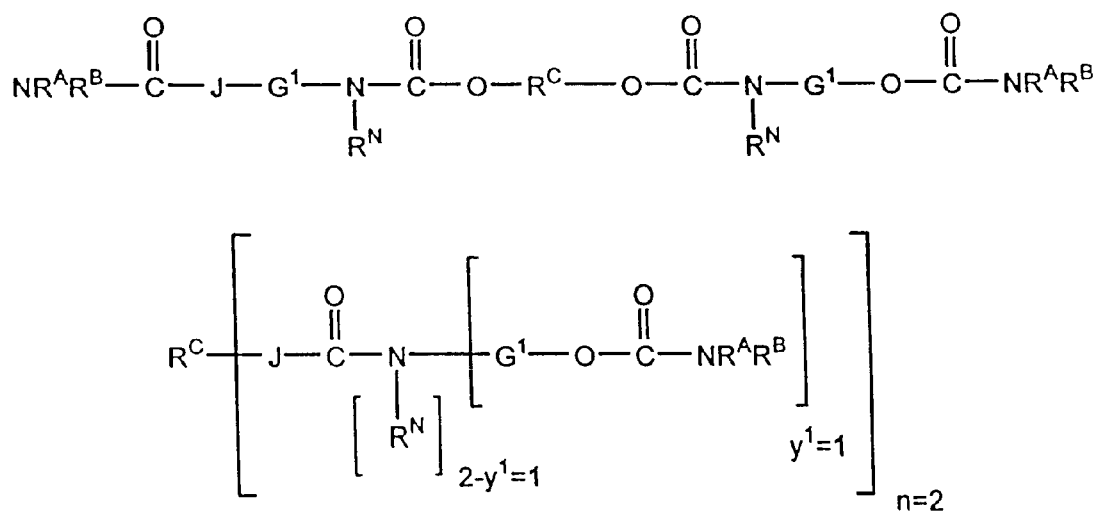
Figure 3:
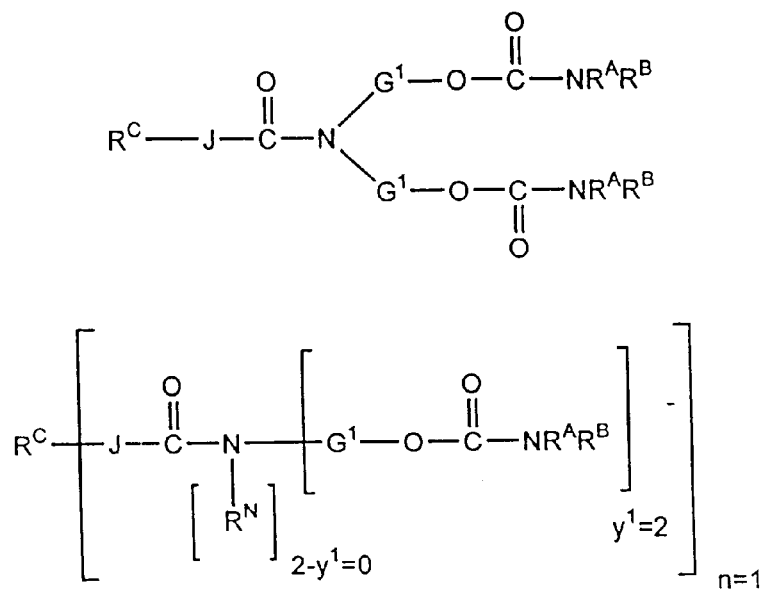
FIG. 3 shows certain valency platforms of the present invention, specifically, some of those having the structure of Formula I.
Figure 3:
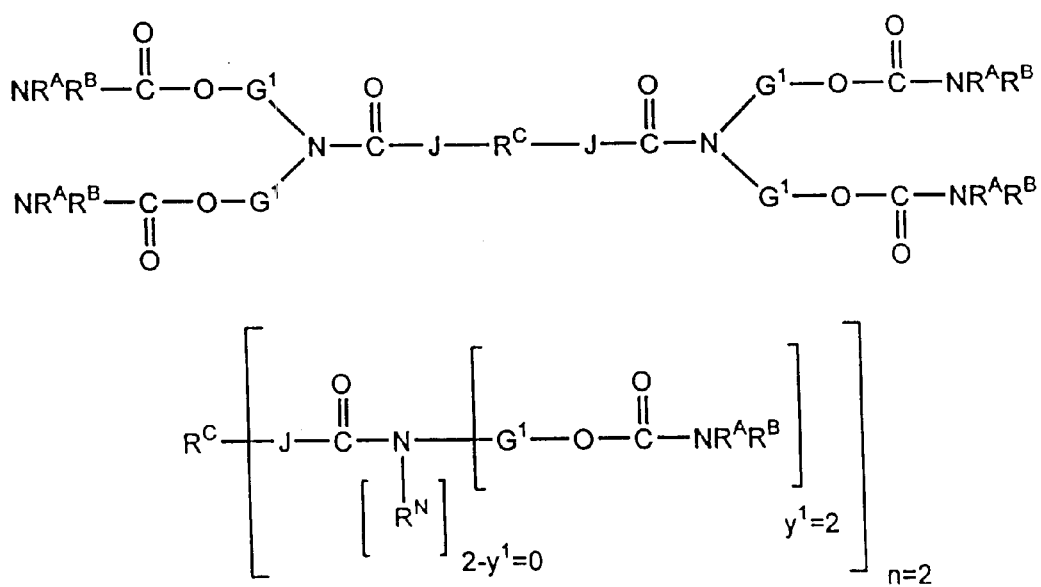
Figure 7:
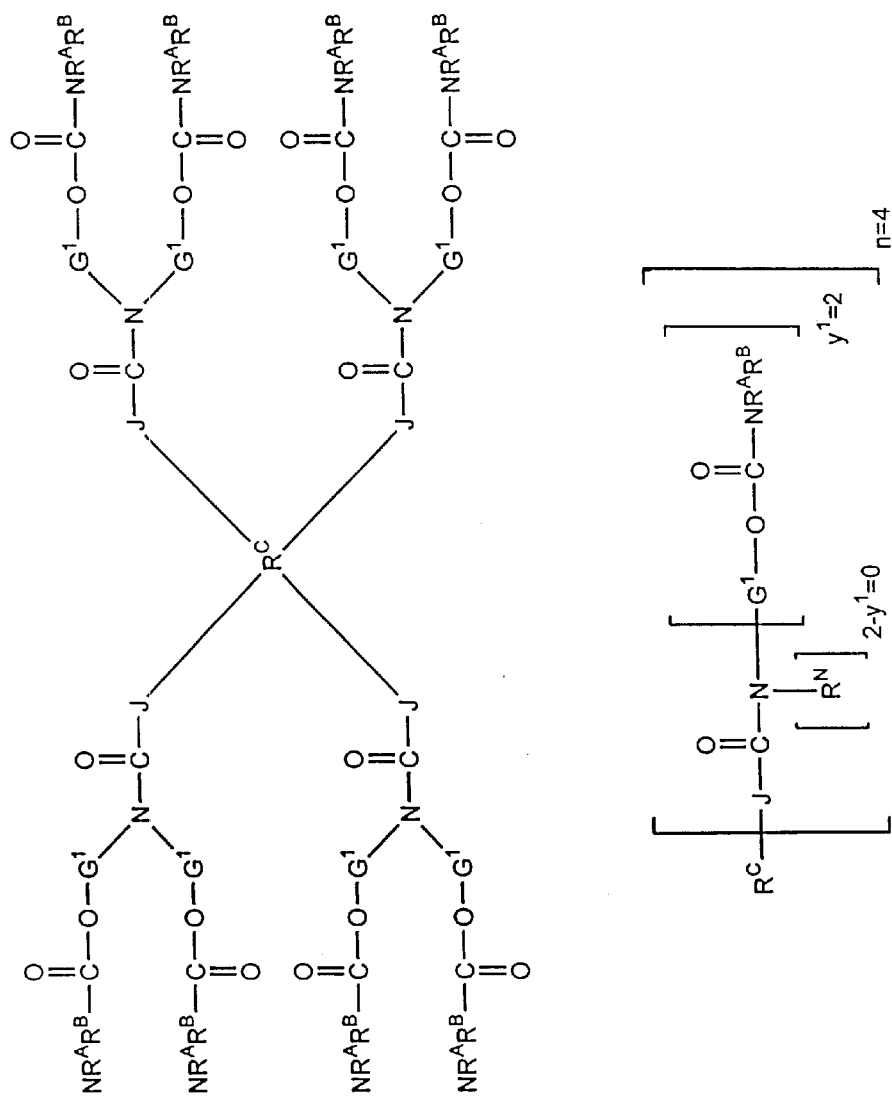
FIG. 7 shows certain valency platforms of the present invention, specifically, some of those having the structure of Formula I.

Examples of valency platforms having the structure of Formula I are shown in FIGS. 2, 3, and 7. In FIG. 2, the top structure has n=1 and $y^1$=1 and the bottom structure has n=2 and $y^1$=1. In FIG. 3, the top structure has n=1 and $y^1$=2 and the bottom structure has n=2 and $y^1$=2. In FIG. 7, the structure has n=4 and $y^1$=2. The number of terminal groups —$NR^AR^B$ is given by "n*$y^1$" When "n*$y^1$" is 4, the structure may conveniently be referred to as a "tetrameric" structure. When "n*y¹" is 8, the structure may conveniently be referred to as a "octameric" structure. When "n*y¹" is 16, the structure may conveniently be referred to as a "hexadecameric" structure.

Examples of compounds having the structure of Formula I where Z is —H include, but are not limited to, compounds 21, 24, 27a, 29, 32, and 38, described in the Examples below.

Examples of compounds having the structure of Formula I where Z is —C(=O)OR$^{CARB}$ include, but are not limited to, compounds 22, 25, 27, 30, 33, and 39 described in the Examples below.

Examples of compounds having the structure of Formula I where Z is —NR$^A$R$^B$ include, but are not limited to, compounds 23, 23a, 26, 26a, 31, 31a, 34, 34a, 40, 41, 42, and 51, described in the Examples below.

Formula II

Figure 5:
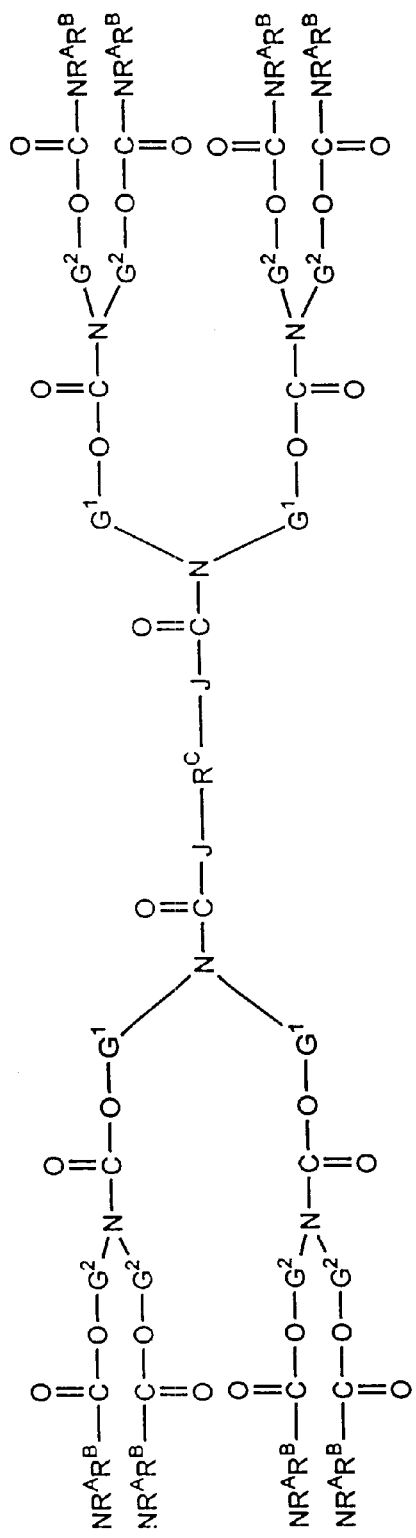
FIG. 5 shows certain valency platforms of the present invention, specifically, some of those having the structure of Formula II.
Figure 5:
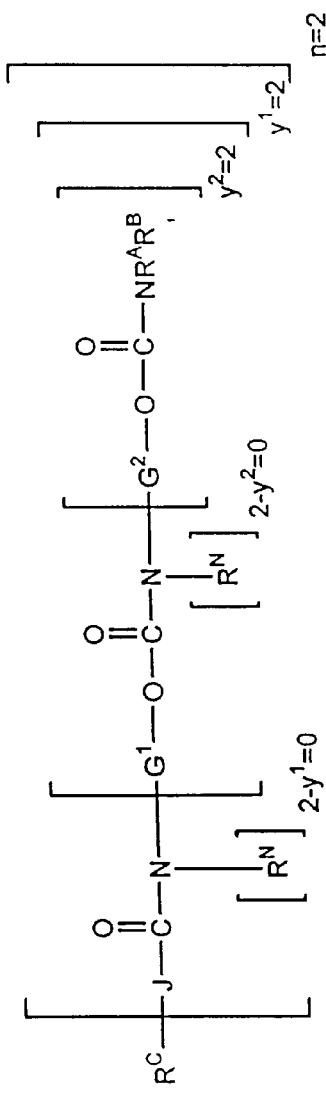

In one embodiment, the present invention pertains to a valency platform having the structure of Formula II, as shown in FIG. 1.

has n=1, y¹=2, and y²=2. In FIG. 5, the structure has n=2, y¹=2, and y²=2. The number of terminal groups —NR$^A$R$^B$ is given by "n*y¹*y²." When "n*y¹*y²" is 4, the structure may conveniently be referred to as a "tetrameric" structure. When "n*y¹*y²" is 8, the structure may conveniently be referred to as a "octameric" structure. When "n*y¹*y²" is 16, the structure may conveniently be referred to as a "hexadecameric" structure.

Examples of compounds having the structure of Formula II where Z is —H include, but are not limited to, compounds 35, 43a, and 49a, described in the Examples below.

Examples of compounds having the structure of Formula II where Z is —C(=O)OR$^{CARB}$ include, but are not limited to, compounds 35a, 43, and 50, described in the Examples below.

Examples of compounds having the structure of Formula II where Z is —NR$^A$R$^B$ include, but are not limited to, compounds 14, 15, 20, 20a, 28, 28a, 36, 36a, 44, 44a, and 45, described in the Examples below.

Formula III

In one embodiment, the present invention pertains to a valency platform having the structure of Formula III, as shown in FIG. 1.

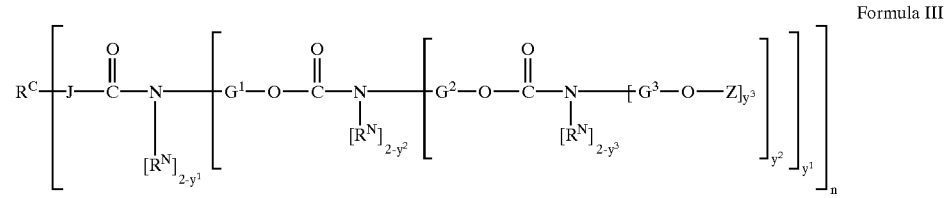

Formula III

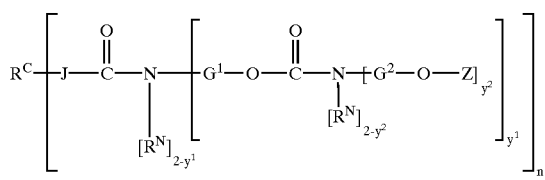

Formula II

In Formula II, n, R$^C$, J, R$^A$, R$^B$, y¹, R$^N$, G¹, and Z are as defined above for Formulae I. In Formula II, y² and G² are as defined above for y¹ and G¹, respectively.

Figure 4:
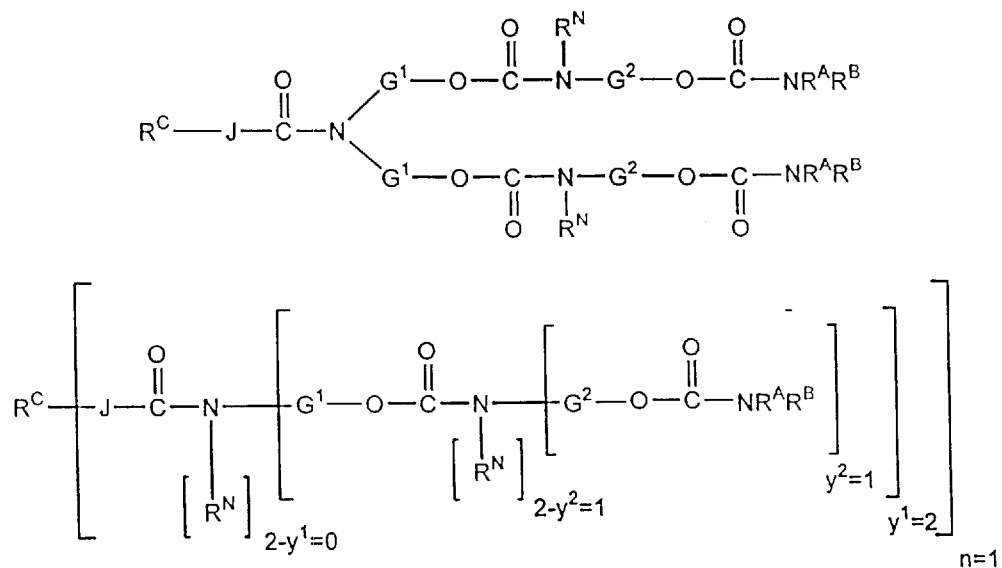
FIG. 4 shows certain valency platforms of the present invention, specifically, some of those having the structure of Formula II.
Figure 4:
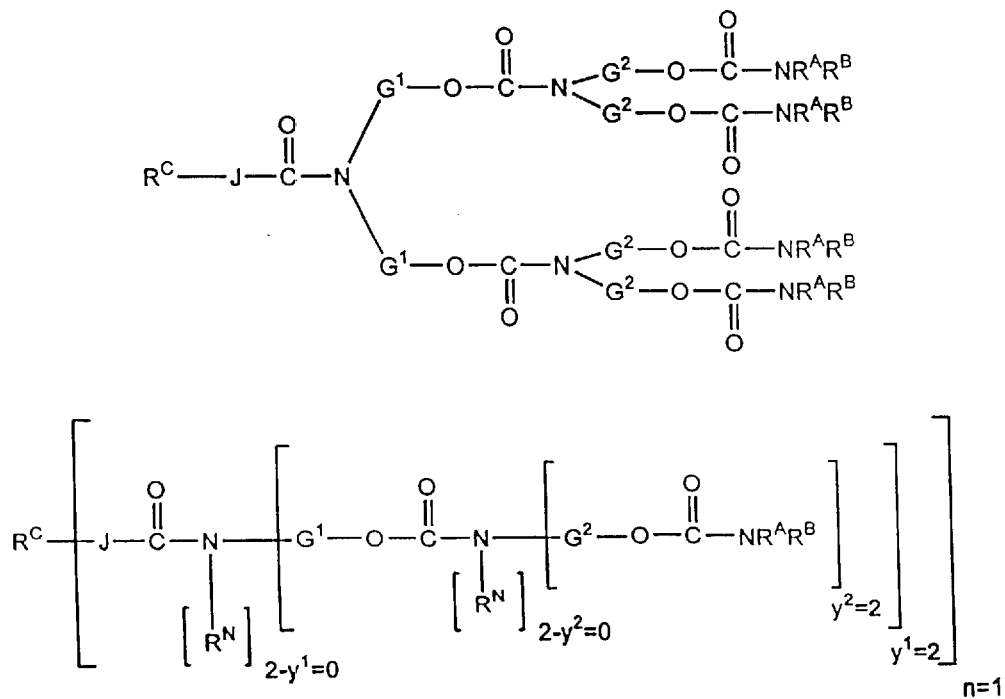

Examples of valency platforms having the structure of Formula II are shown in FIGS. 4 and 5. In FIG. 4, the top structure has n=1, y¹=2, and y²=1 and the bottom structure In Formula III, n, R$^C$, J, R$^A$, R$^B$, y¹, y², R$^N$, G¹, G², and Z are as defined above for Formulae I and II. In Formula III, y³ and G³ are as defined above for y¹ and G¹, respectively.

Figure 6:
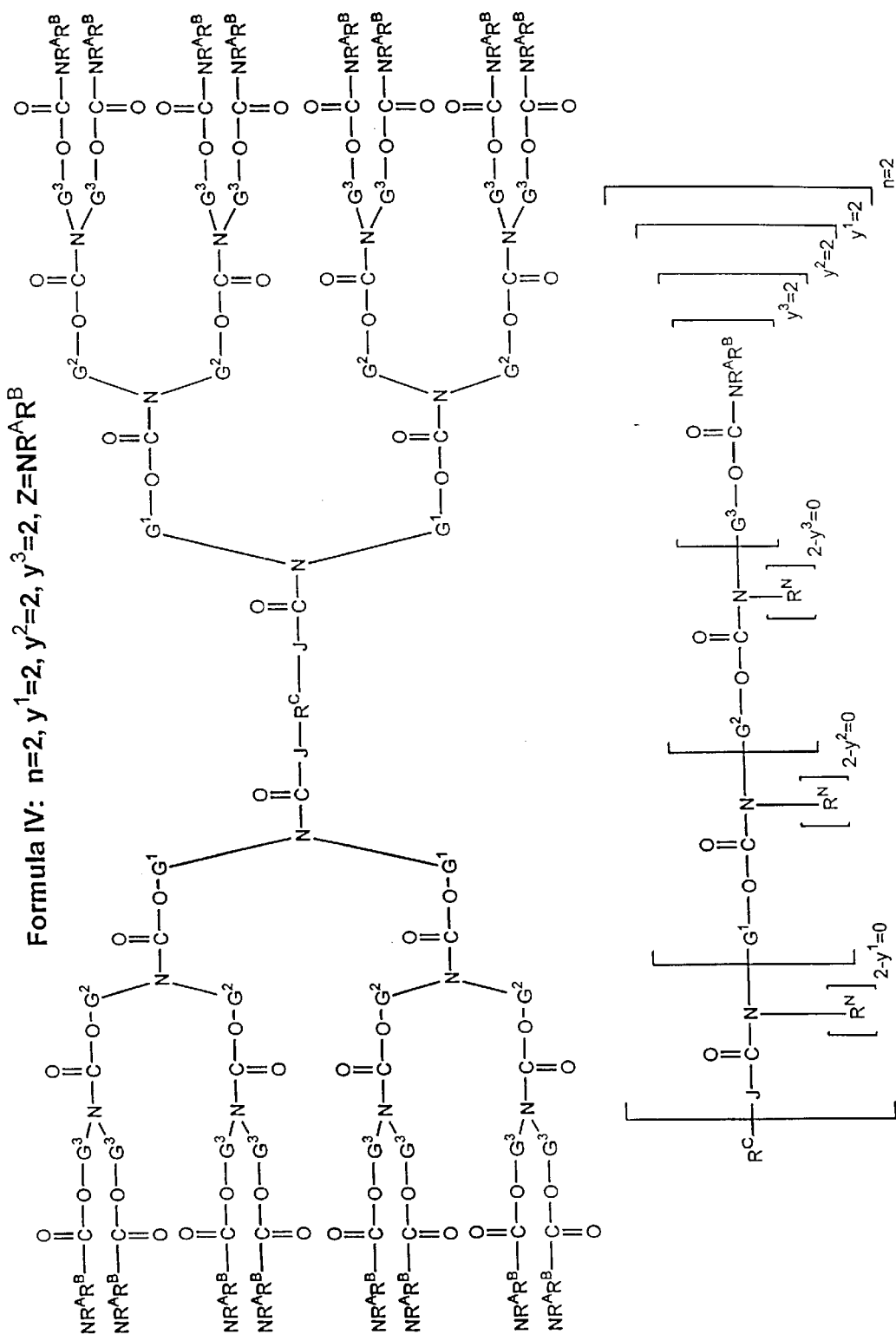
FIG. 6 shows certain valency platforms of the present invention, specifically, some of those having the structure of Formula III.

Examples of a valency platform having the structure of Formula III is shown in FIG. 6. This structure has n=2, y¹=2, y²=2, and y³=2. The number of terminal groups —NR$^A$R$^B$ is given by "n*y¹*y²*y³." When "n*y¹*y²*y³" is 4, the structure may conveniently be referred to as a "tetrameric" structure. When "n* y¹*y²*y³" is 8, the structure may conveniently be referred to as a "octameric" structure. When "n*y¹*y²*y³" is 16, the structure may conveniently be referred to as a "hexadecameric" structure.

Formulae IV, V, and VI

Figure 8:
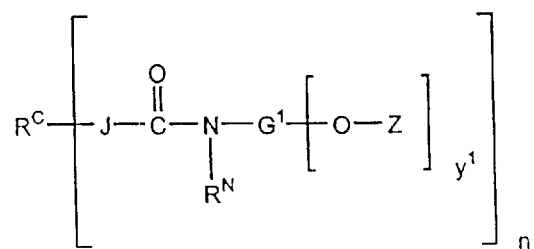
FIG. 8 shows certain valency platforms of the present invention, specifically, those having the structure of Formulae VI, V, and VI.
Figure 8:
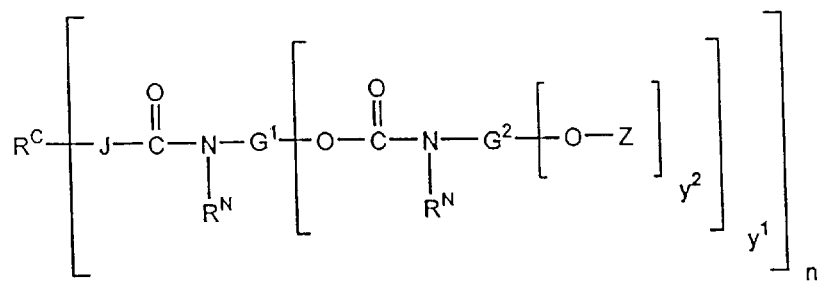
Figure 8:
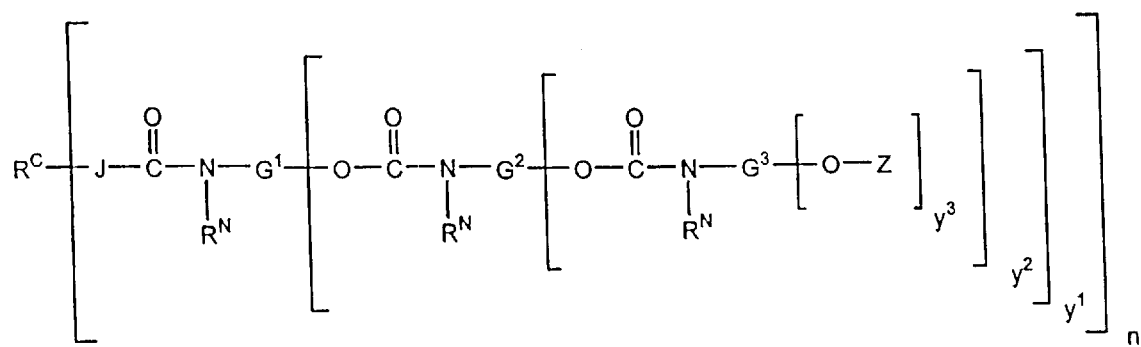
Figure 9:
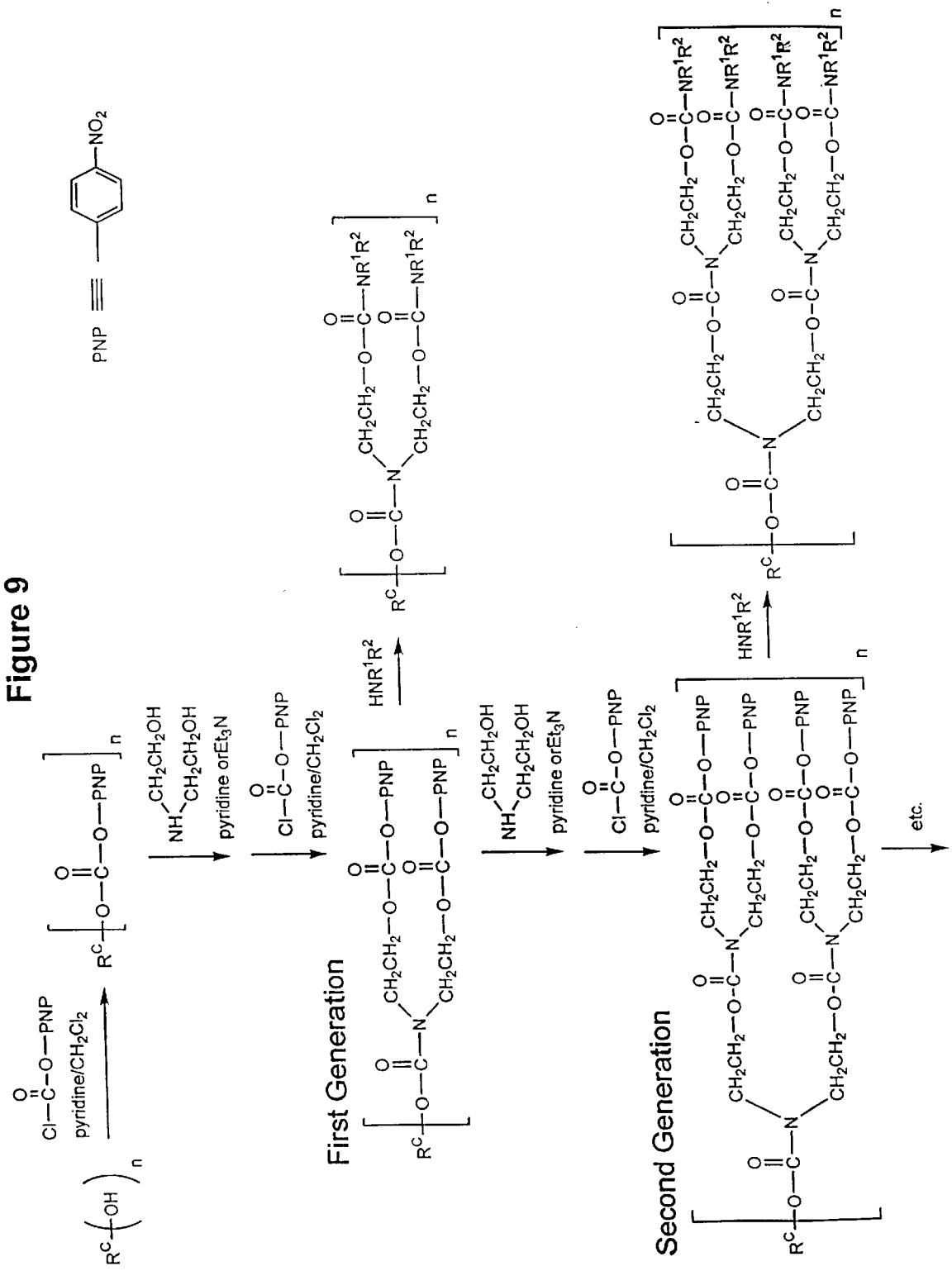
FIG. 9 shows a synthetic scheme for a simple example of "core propagation" to obtain valency platforms of the present invention.

In one embodiment, the present invention pertains to a valency platform having the structure of Formula IV, V, or VI, as shown in FIG. 8.

Formula IV

Formula V

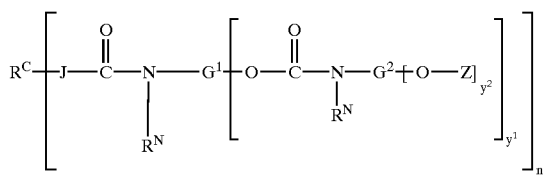

Formula VI

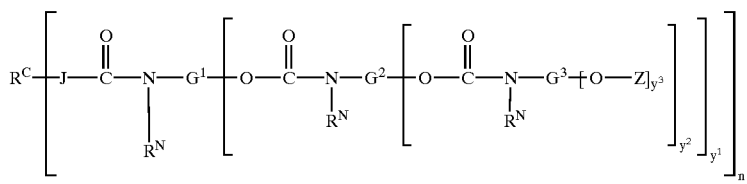

In these formulae, n, $R^C$, J, $R^A$, $R^B$, $R^N$, and Z are as defined above for Formulae I through III. Unlike the compounds of Formulae I through III, which may have branch points at nitrogen atoms, compounds of Formulae IV through VI may have branch points at a G group, for example, at $G^1$, $G^2$, or $G^3$, and there may be one, two, three, or more branches, for example, $y^1$, $y^2$, or $y^3$ branches.

For Formulae IV through VII, $G^1$, $G^2$, and $G^3$ are similar to $G^1$, $G^2$, and $G^3$ for Formulae I through III. In a preferred embodiments, these groups are trivalent, tetravalent or higher. In one embodiment, $G^1$, $G^2$, and $G^3$ are selected from the group consisting of:

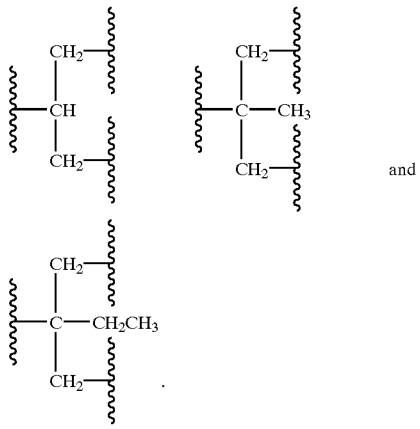

Also, for Formulae IV through VI, $y^1$, $y^2$, and $y^3$ are positive integers from 1 to about 10, more preferably from 1 to 5, more preferably from 1 to 4, more preferably from 1 to 3, more preferably from 1 to 2.

Examples of compounds having the structure of Formula IV where Z is —H include, but are not limited to, compound 46, described in the Examples below.

Examples of compounds having the structure of Formula IV where Z is —C(=O)OR$^{CARB}$ include, but are not limited to, compound 47, described in the Examples below.

Examples of compounds having the structure of Formula V where Z is —H include, but are not limited to, compound 47a, described in the Examples below.

Examples of compounds having the structure of Formula V where Z is —C(=O)OR$^{CARB}$ include, but are not limited to, compound 48, described in the Examples below.

Examples of compounds having the structure of Formula V where Z is —NR$^A$R$^B$ include, but are not limited to, compounds 48a, 48b, and 48c, described in the Examples below.

In general, the number of termini may be calculated as the product of n, $y^1$, $y^2$, $y^3$, etc., as discussed above. In one embodiment, this product is 2 or more. In one embodiment, this product is more than 2. In one embodiment, this product is more than 3. In one embodiment, this product is 4. In one embodiment, this product is 6. In one embodiment, this product is 8. In one embodiment, this product is 16. In one embodiment, this product is 32.

In some embodiments, the valency platform molecule may be described as "dendritic," owing to the presence of successive branch points. Dendritic valency platform molecules possess multiple termini, typically 4 or more termini. In one embodiment, the valency platform molecule is dendritic and has 4 termini, such as, for example, compounds 23a, 26a, 31a, 34a, 42a, described in the examples below. In one embodiment, the valency platform molecule is dendritic and has 8 termini, such as, for example, compounds 15, 20a, 28a, 36a, 45, 48c and 51, described in the examples below. In one embodiment, the valency platform molecule is dendritic and has 16 termini.

Note that Formulae I through VI are intended to encompass both "symmetric" and "non-symmetric" valency platforms. In one embodiment, the valency platform is symmetric. In one embodiment, the valency platform is non-symmetric. For example, each of the "n" groups which are pendant from the core group, RC, may be the same or may be independently different.

"Higher generation" valency platforms (e.g., 4th generation, 5th generation) are also contemplated, which have corresponding formulae. For example, 4th generation valency platforms would have $G^4$ and $y^4$, 5th generation valency platforms would further have $G^5$ and $y^5$, and so on for successive generations. Also, "hybrid" valency platforms are contemplated, which would include linkages of the sort found in Formulae I through III as well as linkages of the sort found in Formulae IV through VI.

B. Preparation of Valency Platforms

In one embodiment, the valency platforms of the present invention may be prepared from "core" compounds which comprise one or more (say, $j^0$) hydroxy groups (i.e., —OH). For example, the hydroxyl groups on the core are converted to active carbonate derivatives, such as activated carbonate esters (for example, a para-nitrophenylcarbonate ester) and subsequently reacted with a polyhydroxyamine compounds having $j^1$ hydroxy groups to provide a "first generation" carbamate with $j^1$ hydroxyl groups for each original hydroxyl group, for a total of $j^0*j^1$ hydroxyl groups. The resulting hydroxy groups may then also be converted to activated carbonate derivatives, such as activated carbonate esters and subsequently reacted with a polyhydroxyamine compound having $j^2$ hydroxy groups to provide a "second generation" carbamate with $j^2$ hydroxyl groups for each $j^1$ hydroxyl group, for a total of $j^0*j^1*j^2$ hydroxyl groups. In this way, a dendritic structure may be constructed. The process can be terminated at any "generation" by treating the terminal activated carbonate derivatives, such as activated carbonate esters, with an appropriately functionalized compound (for example, an mono-protected diamine) to provide whatever functionality is desired at the termini.

In one embodiment, the valency platforms of the present invention may be prepared from a "segmental approach" in which "segments" are independently synthesized and subsequently attached to a "core" group.

In another embodiment, an alternative, more efficient "core propagation" process has been developed in which a core group is modified in an iterative process to generate a dendritic structure. The core propagation approach involves fewer steps and is preferred over the segmental approach.

In another embodiment, the valency platforms of the present invention may be prepared using solid phase synthesis from a hydroxyl containing resin. Such an embodiment is illustrated in FIG. 20. A hydroxyl group attached to a solid phase by a cleavable linker provides a way of building a dendrimeric scaffold using solid phase synthesis. The ability to prepare scaffolds on the solid phase can be particularly useful for the rapid synthesis of dendrimeric platforms with minimal purification. Also, solid phase dendrimeric platforms can be used to generate combinatorial libraries of multivalent compounds.

In one preferred "core propagation" approach, the synthesis typically begins with an alcohol containing "core compound." In principle, any hydroxyl-containing compound can be used. Examples of alcohol containing "core compounds" having one hydroxyl group (i.e., —OH) include, but are not limited to:

methanol,

ethanol,

propanol,

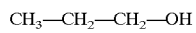

isopropanol,

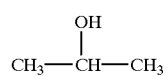

methoxypolyethylene glycol,

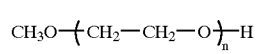

Other examples of alcohol containing "core compounds" having one hydroxyl group (i.e., —OH) include, but are not limited to, mono-hydroxylamines, such as those described below, for which the amino group may be in a protected form, for example, using a BOC or CBZ protecting group.

Examples of alcohol containing "core compounds" having two hydroxyl groups (i.e., —OH) include, but are not limited to:

ethylene glycol,

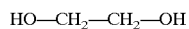

diethylene glycol (also referred to as DEG),

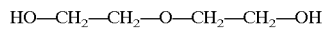

triethylene glycol (also referred to as TEG),

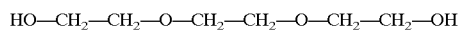

tetraethylene glycol,

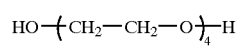

pentaethylene glycol,

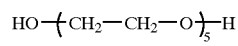

hexaethylene glycol,

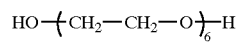

polyethylene glycol (also referred to as PEG), where n is typically from 1 to about 200,

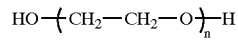

1,4-dihydroxymethylbenzene,

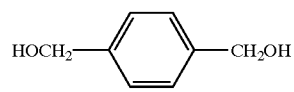

Other examples of alcohol containing "core compounds" having two hydroxyl groups (i.e., —OH) include, but are not limited to, primary or secondary amines having two hydroxyl groups, such as those described below. Again, the amino group may be in a protected form, for example, using a BOC or CBZ protecting group.

Examples of alcohol containing "core compounds" having three hydroxyl groups (i.e., —OH) include, but are not limited to:

phluoroglucinol (also known as 1,3,5-trihydroxybenzene),

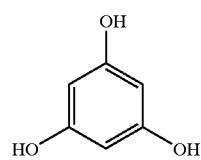

1,3,5-trihydroxymethylbenzene,

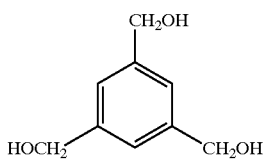

1,3,5-trihydroxycyclohexane,

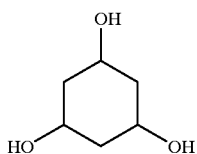

Other examples of alcohol containing "core compounds" having three or more hydroxyl groups (i.e., —OH) include, but are not limited to, primary or secondary amines having three hydroxyl groups, such as those described below. Again, the amino group may be in a protected form, for example, using a BOC or CBZ protecting group.

Examples of alcohol containing "core compounds" having four hydroxyl groups (i.e., —OH) include, but are not limited to:

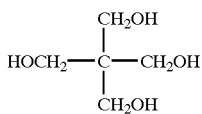

Further examples of alcohol containing "core compounds" include, but are not limited to, those which comprise a sulfhydryl group (i.e., —SH), which may be protected, for example, with a trityl protecting group (i.e., as —S—Tr, that is, —S—C(C₆H₅)₃) or as a disulfide (i.e., as —S—SR). Examples of core groups which have a protected sulfhydryl group include, but are not limited to, the following:

Tr—S—CH₂CH₂—OH
HO—CH₂CH₂—S—S—CH₂CH₂—OH

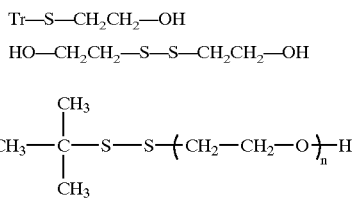

where n is from 1 to about 200, preferably from 1 to about 20.

In addition, hydroxyl groups on solid phase synthesis resins can be used as core groups to provide dendrimeric carbamate residues on solid phase which can be used to boost the valence of the resin or cleaved off the resin. For example, a Wang resin of the following form may be used:

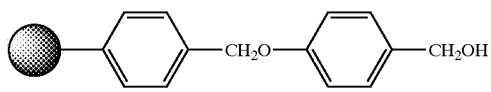

In one embodiment, a hydroxy containing core group may be prepared from a corresponding carboxylic acid compound or halocarbonyl compound:

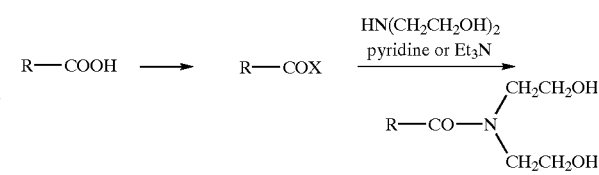

Core compounds which possess amino or sulfhydryl groups, which may be protected or unprotected, may be used to covalently attach the resulting valency platform molecule to other molecules of interest, via the core group rather than via the termini, using conjugation methods such as those described herein.

In one step, the hydroxyl groups of the alcohol containing core group are converted to active carbonate derivatives. The active carbonate derivative in one embodiment has the formula:

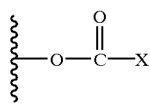

where X is a leaving group such as Cl, imidazole or thiolate.

The hydroxyl groups of the alcohol can be converted to active active carbonates by reaction of the hydroxyl groups of the alcohol containing core group with a phosgene equivalent. Phosgene equivalents with appropriate reactivity can be selected. The phosgene equivalent has, for example, the structure $X_1(CO)X_2$ where $X_1$ and $X_2$ are both leaving groups. $X_1$ and $X_2$ each independently can be chosen from typical leaving groups in acylation chemistry such as alkoxide, thiolate, halide, and imidazole. In one preferred embodiment, the phosgene equivalent is 4-nitrophenylchloroformate. In another embodiment, the phosgene equivalent is carbonyldiimidazole. Other exemplary phosgene equivalents include phosgene, N,N'-succinimidylcarbonate, succinimidyl 2,2,2-trichloroethylcarbonate, bis-4-nitrophenylcarbonate, triphosgene, 2,2,2-trichloroethylchloroformate, 4-nitrophenylchloroformate, phenylchloroformate, N-hydroxysuccinimidylchloroformate, trichloromethylchloroformate, ethylchlorothiolformate, di-(1-benzotriazolyl)carbonate, and 4-nitrophenylsuccinimidylcarbonate.

Figure 21:
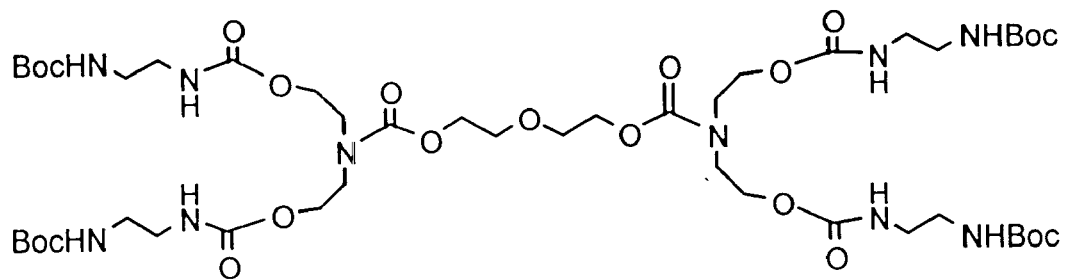
FIG. 21 shows the structure of examples of two carbamate compounds 39b and 39c.
Figure 21:
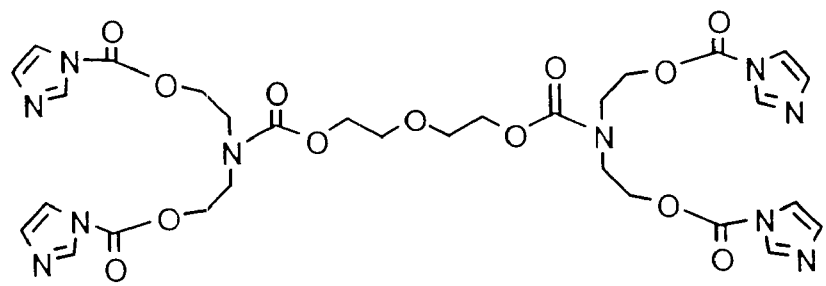

Thus, in one embodiment, to form an active carbonate derivative in the synthesis of the valency platform molecule, an alcohol is reacted with the phosgene equivalent to form the activated carbonate by displacing $X_1$. $X_1$ is chloride in one preferred embodiment. The active carbonate derivative is used to acylate an aminoalcohol on the nitrogen, forming the carbamate bond, then the phosgene again is added to convert the hydroxyl group to another active carbonate derivative. An example of an active carbonate derivative is compound 39c shown in FIG. 21.

In one embodiment, the active carbonate derivative is a carbonate ester. The terms "carbonate" and "carbonate ester" are used herein in the conventional sense and relate to species which comprise the following structure:

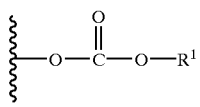

wherein $R^1$ denotes a carbonate group, such as an organic group having from 1 to 20 carbon atoms. The terms "activated carbonate" and "activated carbonate ester" are used herein to refer to carbonates for which $R^1$ is an activating group, and for which the moiety —O—$R^1$ forms a good leaving group. A particularly preferred class of activated carbonate esters include, but are not limited to para-nitrophenyl carbonate ester compounds of the formula:

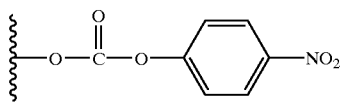

Such "PNP" activated carbonate esters may readily be formed from the corresponding alcohol, R—OH by reaction with PNP chloroformate in the presence of pyridine ($C_5H_5N$) in methylene chloride ($CH_2Cl_2$).

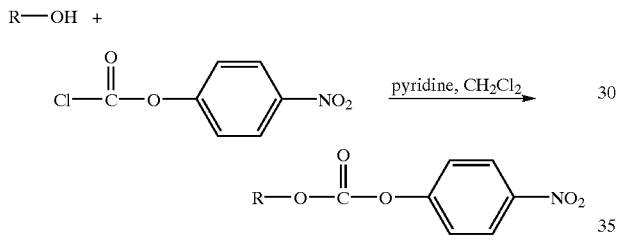

Examples of other activated carbonate groups include, but are not limited to, the following:

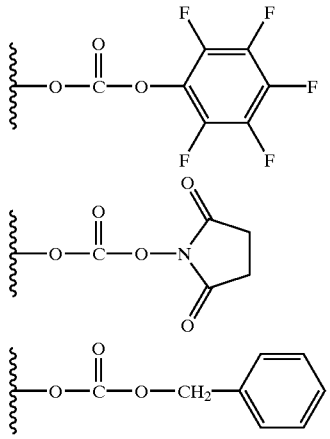

In another step, the activated carbonate ester is converted to the corresponding carbamate. The above PNP activated carbonate esters are readily converted to the corresponding carbamates by reaction with an amine. The dendritic structure may be extended by employing a primary or secondary amine having $j^1$ hydroxy groups. In this way, each original hydroxy group, which led to an activated carbonate ester group, then leads to $j^1$ hydroxy groups.

For example, the PNP activated carbonate ester may be reacted with a primary or secondary dihydroxyamine. Examples of primary and secondary amines having two hydroxyl groups include, but are not limited to:

diethanolamine,

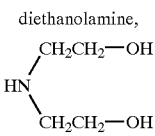

bis(diethyleneglycol)amine (compound 7),

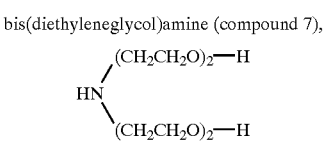

bis(triethyleneglycol)amine,

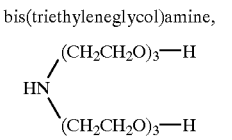

bis(tetraethylleneglycol)amine,

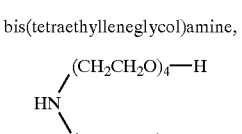

bis(pentaethyleneglycol)amine,

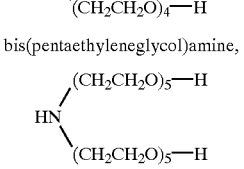

bis(hexaethyleneglycol)amine (compound 4),

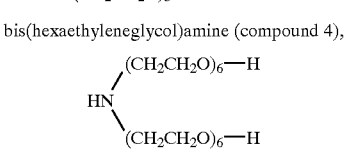

bis(polyethyleneglycol)amine (where n is from 1 to about 20),

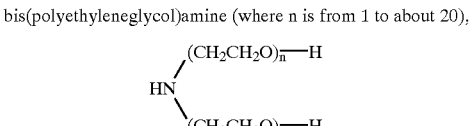

diisopropanolamine,

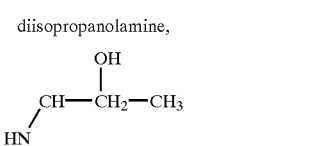

serinol (also known as 2-amino-1, 3-propanediol),

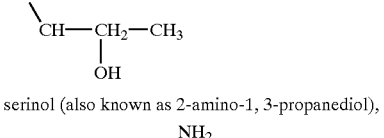

2-amino-2-methyl-1, 3-propanediol,

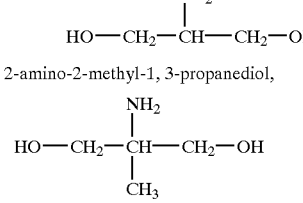

2-amino-2-ethyl-1, 3-propanediol,

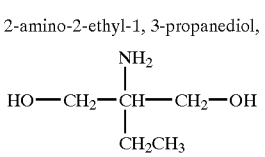

-continued tris(hydroxymethyl)aminomethane,

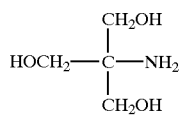

tris(hydroxyethyl)aminomethane,

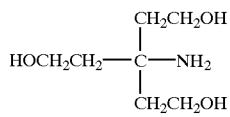

1-amino-1-deoxysorbitol (also referred to as glucamine),

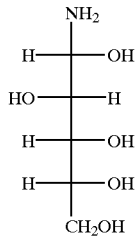

N-methyl-D-glucamine,

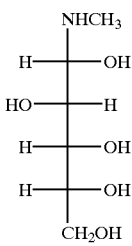

In one step, the activated carbonate ester is converted to the corresponding carbamate using a monohydroxyamine to maintain valency from one generation to the next yet impart unique properties such as arm length, steric bulk, solubility, or other physical properties. Examples of such monohydroxyamines include, but are not limited to:

3-pyrrolidinol,

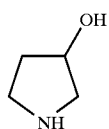

2-(hydroxymethyl)pyrrolidine,

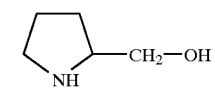

3-hydroxypiperidine (also referred to as 3-piperidinol),

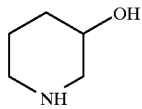

3-(hydroxymethyl)piperidine,

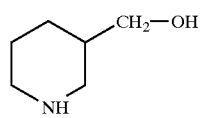

-continued 2-(hycroxymethyl)piperidine,

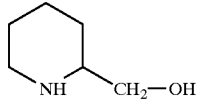

4-(2-hydroxyethyl)piperidine,

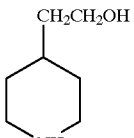

4-piperidinol,

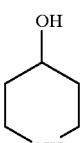

2, 2, 6, 6, -tetramethyl-4-piperidinol,

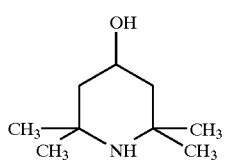

mono-amino-oligoethylene glycol (where n is from 1 to about 10),

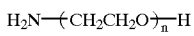

mono-amino-polyethylene glycol (where n is from 1 to about 200),

In one step, the activated carbonate ester is converted to the corresponding carbamate using a primary or secondary amine which acts as a "terminating" amine. In one embodiment, a mono-protected diamine is employed. In a preferred embodiment, the terminating amine is a mono-CBZ protected piperazine, since this compound provides a convenient secondary amine handle for adding functionality by acylation with other reactive groups such as haloacetyl, maleimidoyl, etc. depending on what is desired at the N-terminus. For example, reaction with mono-CBZ-protected piperazine in the presence of triethylamine $((CH_3CH_2)_3N)$ in methylene chloride $(CH_2Cl_2)$ yields the CBZ-protected piperazine carbamate, which can then be converted to a haloacetyl group:

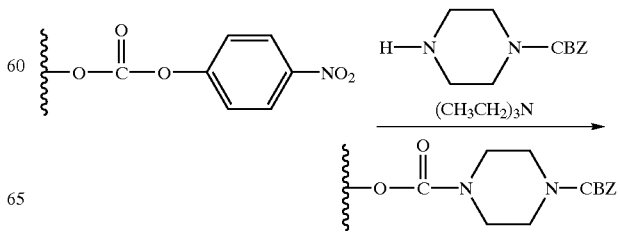

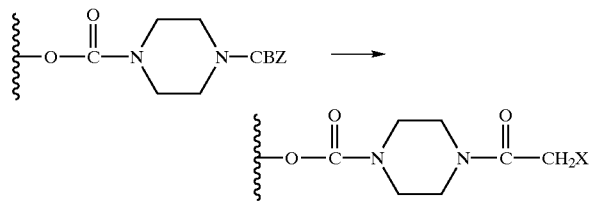

Ethylenediamine and other diamines can function similarly. Examples of preferred terminating amines include, but are not limited to those shown below, as well as monoprotected (e.g., mono-CBZ-protected) forms thereof:

ethylenediamine,

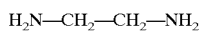

propylenediamine,

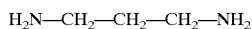

alkylenediamines (where n is an integer from 1 to about 20),

N,N'-dimethylethylenediamine,

α,ω-diaminopolyethyleneglycol (where n is an integer from 1 to about 200, preferably from 1 to about 20),

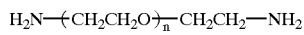

A particularly preferred terminating amines is mono-CBZ-protected piperazine:

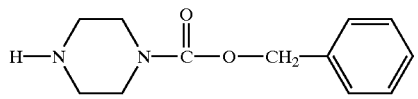

In principle any primary or secondary amine containing compound which contains a reactive conjugating group (such as those described above) or a biologically active molecule can be used to terminate the dendrimer and provide the terminal functionality that is desired. For example, amino alcohols would provide terminal hydroxyl groups, amino aldehydes would provide terminal aldehyde groups, amino acids would provide terminal carboxylic acids, and aminothiols would provide terminal thiols. Methods for the introduction of other reactive conjugating functional groups, such as those described above, as terminating groups are well known to those of skill in the art.

C. Valency Platform Conjugates, Methods of Preparation, and Uses Thereof

In one embodiment, valency platform molecules are provided which act as scaffolds to which one or more molecules may be covalently tethered to form a conjugate. Thus, in another aspect, the present invention pertains to valency platform conjugates.

In one embodiment, the valency platform is covalently linked to one or more biologically active molecules, to form a conjugate. The term "biologically active molecule" is used herein to refer to molecules which have biological activity, preferably in vivo. In one embodiment, the biologically active molecule is one which interacts specifically with receptor proteins.

In one embodiment, the valency platform is covalently linked to one or more oligonucleotides, to form a conjugate. In one embodiment, the valency platform is covalently linked to one or more peptides, to form a conjugate. In one embodiment, the valency platform is covalently linked to one or more polypeptides, to form a conjugate. In one embodiment, the valency platform is covalently linked to one or more proteins, to form a conjugate. In one embodiment, the valency platform is covalently linked to one or more antibodies, to form a conjugate. In one embodiment, the valency platform is covalently linked to one or more saccharides, to form a conjugate. In one embodiment, the valency platform is covalently linked to one or more polysaccharides, to form a conjugate. In one embodiment, the valency platform is covalently linked to one or more epitopes, to form a conjugate. In one embodiment, the valency platform is covalently linked to one or more mimotopes, to form a conjugate. In one embodiment, the valency platform is covalently linked to one or more drugs, to form a conjugate.

In one embodiment, the biological molecule is first modified to possess a functionalized linker arm, to facilitate conjugation. An example of such a functionalized linker arm is a polyethylene glycol disulfide, such as, for example:

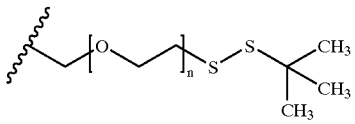

One advantage of the valency platforms of the present invention is the ability to introduce enhanced affinity of the tethered biologically active molecules for their binding partners. Another advantage of the valency platforms of the present invention is the ability to facilitate crosslinking of multiple ligands, as is useful in B cell tolerance. Another advantage of the valency platforms of the invention is the ability to include functionality on the "core" that can be independently modified to enable the preparation of conjugates which can be tailored for specific purposes.

Conjugates of the valency platform molecule and one or more biologically active molecules may be prepared using known chemical synthetic methods. As discussed above, the termini of the valency platform molecule (i.e., the $R^A$, $R^B$, and/or $R^{AB}$ of the group —$NR^AR^B$, as discussed above) preferably comprise a reactive conjugating functional group, and this reactive functional group may be used to couple the valency platform to the desired biologically active molecule.

In one embodiment, the reactive haloacetyl group may be used to couple the valency platform to a biologically active molecule which possesses one or more reactive conjugating functional groups which are reactive towards the haloacetyl group, and which react to yield a covalent linkage.

For example, if the biologically active molecule is a protein which has one or more free amino groups (i.e., —$NH_2$), the two groups may be used to form the conjugate:

31

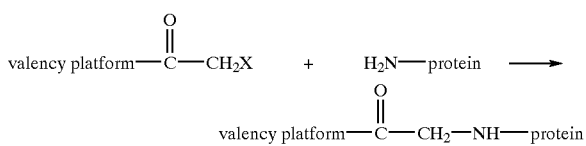

In another example, if the biologically active molecule is a protein which has one or more free thiol groups (i.e., —SH) or sulfide groups (i.e., —SR), the two groups may be used to form the conjugate:

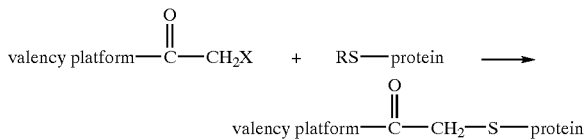

In another embodiment, a terminal maleimidoyl group may be used to couple the valency platform to a biologically active molecule which possesses one or more reactive conjugating functional groups which are reactive towards the maleimidoyl group, and which react to yield a covalent linkage.

For example, if the biologically active molecule is a protein which has one or more free thiol groups (i.e., —SH) or sulfide groups (i.e., —SR), the two groups may be used to form the conjugate:

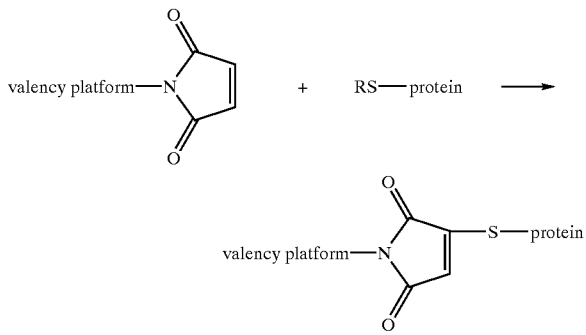

D. EXAMPLES

Several embodiments of the present invention are illustrated in the Examples below, which are offered by way of illustration and not by way of limitation.

Example 1

Examples of Synthesis of Amine Diols

Figure 10:
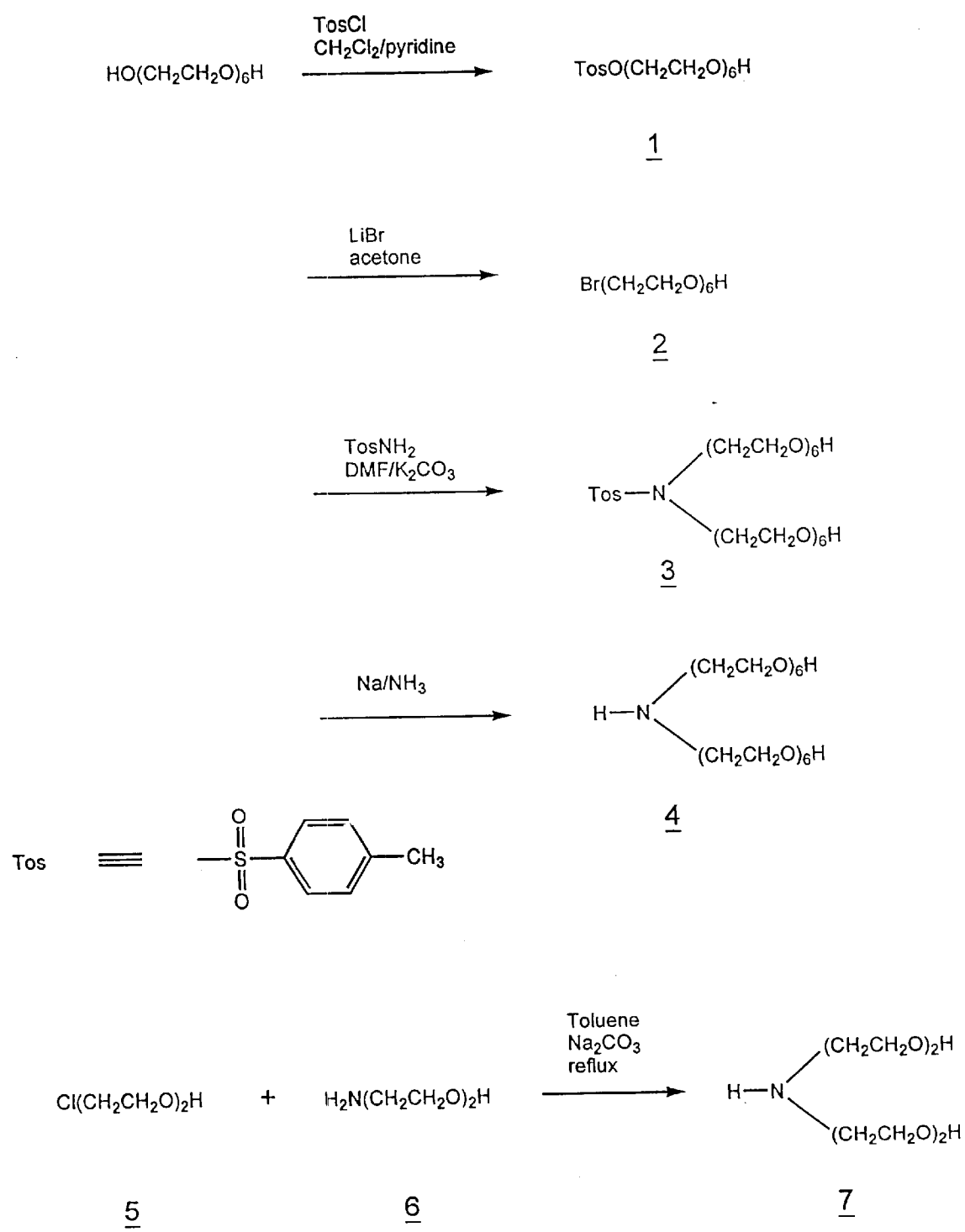
FIG. 10 shows synthetic schemes for the preparation of certain intermediates useful in the preparation of valency platforms of the present invention.

A chemical scheme for the preparation of HEGA (bis-hexaethyleneglycolamine) is shown in FIG. 10. One hydroxy terminus of hexaethylene glycol is first converted to a tosyl group (compound 1), which is then converted to a bromo group (compound 2). The resulting compound is then reacted with tosylamide to yield tosylated bis-hexaethyleneglycolamine (compound 3). The tosyl group is then removed to yield the desired bis-hexaethyleneglycolamine (compound 4).

A chemical scheme for the preparation of DEGA (bis-diethyleneglycolamine) is also shown in FIG. 10. Chloro-diethylene glycol (compound 5) is reacted with aminodiethylene glycol (compound 6) to yield the desired bis-diethyleneglycolamine (compound 7).

32

Compound 1

Hexaethyleneglycol mono-tosylate 25 g (88.5 mmol) of hexaethyleneglycol was stirred at 0° C. in 200 mL of $CH_2Cl_2$, and 14.3 mL of pyridine (177 mmol; 2 eq.) was added to the mixture followed by 17.4 g (88.5 mmol) of tosylchloride. The reaction mixture was stirred at room temperature for 24 hours and partitioned between 400 ml of 1N HCl and 200 ml of $CH_2Cl_2$. The organic layer was dried over $MgSO_4$, filtered, and concentrated to provide 31 g of a light yellow oil. Purification by silica gel chromatography ($CH_2Cl_2$/MeOH) provided 15.32 g (40%) of 1 as a light yellow oil: $^1$H NMR (CDCl$_3$) δ2.45 (s, 3H), 3.55–3.75 (m, 22H), 4.15 (t, 2H), 7.35 (d, 2H), 7.80 (d, 2H); HRMS (FAB) calculated for $C_{19}H_{33}O_9S$ (M+H): 437.1845. Found: 437.1834.

Compound 1

Hexaethyleneglycol mono-tosylate 50 g of HEG (177 mmol) was dissolved in 300 ml of $CH_2Cl_2$ and 7.2 ml (88 mmol) of pyridine was added at room temperature. 17.4 g (88 mmol) of tosylchloride was added to the mixture in four batches, each 2 hours apart. After the last addition, the mixture was stirred for 16 hours. The reaction mixture was concentrated, 150 mL of 0.1 M HCl was added, and the mixture was extracted twice with hexane to remove excess tosylchloride. The aqueous layer was washed with three portions of ether to remove di-tosylate. This was carefully monitored by TLC to avoid any removal of mono-tosylate. The aqueous layer was then extracted with portions of $CH_2Cl_2$. The combined organic layers were washed with 0.1M HCl, dried over $MgSO_4$, filtered, and concentrated to give 23.6 g (31%) of compound 1.

Compound 2

Hexaethyleneglycol mono-bromide

Compound 1 (18 g, 41.3 mmol) was dissolved in 120 mL of acetone and 10.8 g of LiBr (124 mmol) was added. The mixture was stirred at 60° C. for 2 hours, the reaction mixture was allowed to cool to room temperature, and 500 mL of $H_2O$ was added. The mixture was extracted with 2×500 mL of $CH_2Cl_2$. The combined organic layers were dried over $MgSO_4$, filtered, and concentrated to give 13.7 g (96%) of compound 2 as a light yellow oil: $^1$H NMR (CDCl$_3$) δ3.50 (t, 2H), 3.60–3.75 (m, 20H), 3.83 (t, 2H); HRMS (FAB) calculated for $C_{12}H_{26}BrO_6$ (M+H): 345.0913. Found: 345.0922.

Compound 3

N,N—bis-hexethyleneglycol-tosylamide

Compound 2 (3.5 g, 9.8 mmol) and 0.84 g (4.9 mmol) of tosylamide were dissolved in 35 mL of $CH_3CN$. Potassium carbonate (1.63 g (11.8 mmol), which had been dried in the 100° C. oven, was added, and the mixture was refluxed for 18 hours under $N_2$. The mixture was allowed to cool to room temperature, and 150 mL of $H_2O$ was added. The mixture was extracted with 3×150 mL of $CH_2Cl_2$. The combined organic layers were washed with $H_2O$, dried ($MgSO_4$), filtered, and concentrated to give 3.3 g of a light yellow oil. Purification by silica gel chromatography ($CH_2Cl_2$/MeOH) provided 2.7 g (79%) of compound 3 as a light yellow oil: $^1$H NMR (CDCl$_3$) δ2.45 (s, 3H), 3.35 (t, 4H), 3.55–3.8 (m, 44H), 7.27 (d, 2H), 7.69, (d, 2H); HRMS (FAB) calculated for $C_{31}H_{57}CsNO_{14}S$ (M+Cs): 832.2554. Found: 832.2584.

Compound 4

N,N—bis-hexethyleneglycol-amine

Compound 3 (2.74 g) was dissolved in 4 mL of dry THF and transferred to a three-neck flask equipped with a Dewar-condenser. This was stirred at −78° C. as 100 mL of $NH_3$ was condensed into the mixture. Approximately 1–2 g of Na was added to the mixture at −78° C. in small portions until the dark blue color persisted. The cooling bath was removed, and the mixture was then stirred at reflux for 30 minutes. Cooling at −78° C. was continued, and the reaction was carefully quenched with glacial acetic acid until all the blue color disappeared. The $NH_3$ was allowed to evaporate, and the white solid was dried under vacuum to yield compound 4. This material was used as is in subsequent steps assuming a 100% yield.

Compound 7

DEGA (bis-diethyleneglycolamine)

Compound 7 was prepared according to an existing literature procedure as shown below (Bondunov et al., J. Org. Chem. 1995, Vol. 60, pp.6097–6102). 33.8 g (321 mmol) of aminodiethyleneglycol (compound 6), 9.4 g (88.3 mmol) of $Na_2CO_3$, 200 mL of toluene, and 10.0 g (80.3 mmol) of chlorotriethyleneglycol (compound5), were refluxed with a Dean-Starke trap to remove water for 48 hours. The mixture was allowed to cool then filtered and concentrated. The resulting 45.8 g of material was vacuum distilled (bp 153–158° C., 0.1 Torr) to yield 12.0 g (78%) of compound 7.

Example 2

Synthesis of Octamer of HEGA/TEG Using Segmental Approach

Figure 11A:
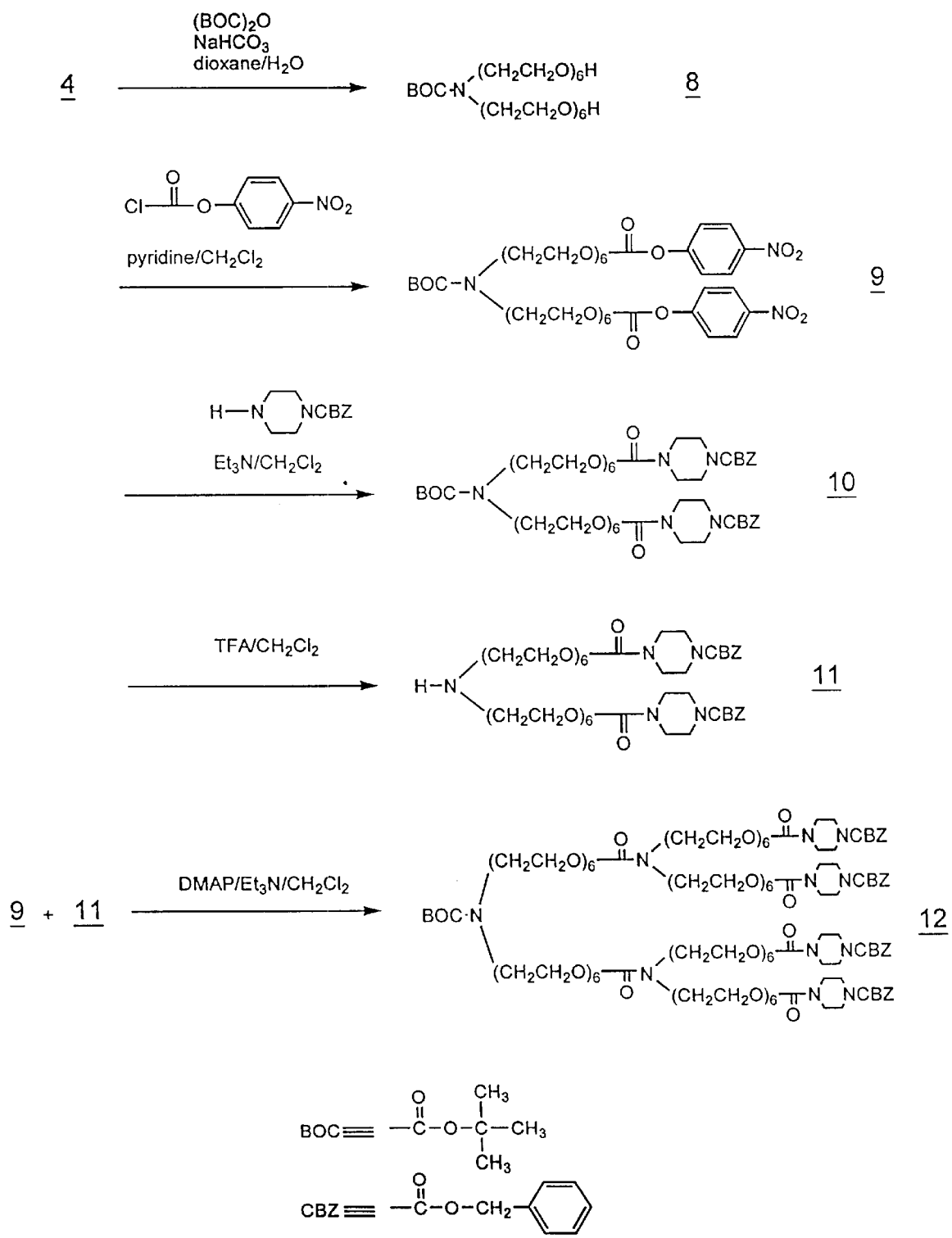
FIGS. 11A and 11B show synthetic schemes for the preparation of valency platform molecules of the present invention.
Figure 11B:
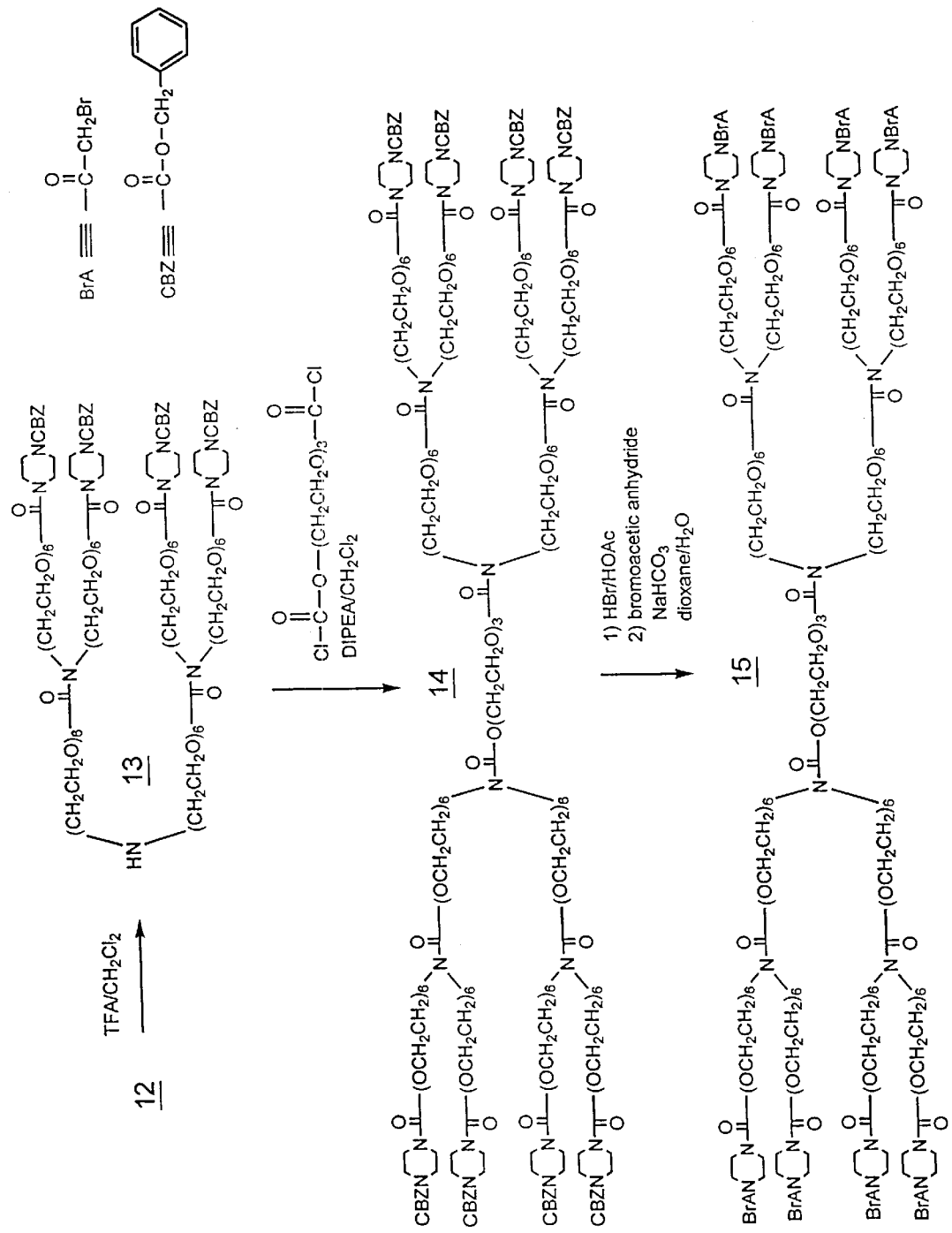

A chemical scheme for the preparation of an octamer of HEGA/TEG is shown in FIGS. 11A and 11B. Compound. The bis-hexaethyleneglycolamine (compound 4) was reacted with di-tert-butyldicarbonate to yield the N-BOC compound (compound 8), which was then reacted with para-nitrophenylchloroformate to yield the para-nitrophenylcarbonate compound (compound 2). The para-nitrophenylcarbonate (PNP) group was then converted to a carbamate group by reaction with mono-CBZ-protected piperazine, yielding compound 10. The BOC group was removed using trifluoroacetic acid to yield compound 11. Compounds 9 and 11 were then reacted together to form a "one-sided" dendritic compound (compound 12). Again, the BOC group was removed using trifluoroacetic acid to yield compound 13. Compound 13 was then reacted with triethyleneglycol bis chloroformate (from which the "core" is derived) to yield the "two-sided" dendritic compound (compound 14). The terminal CBZ-protected amino groups were then converted to the hydrobromide salt of amino group, and further reacted with bromoacetic anhydride to yield reactive bromoacetyl groups at each of the termini in compound 15.

Compound 8

N—BOC-N,N-bis-hexaethyleneglycol-amine

Compound 4 (797 mg, 1.46 mmol) was dissolved in 14 mL of $H_2O$, and the mixture was stirred at room temperature. To the mixture was added 465 mg (4.38 mmol) of $Na_2CO_3$. The pH was checked to make sure it was basic, and 319 mg (1.46 mmol) of di-tert-butyldicarbonate ($(BOC)_2O$) was dissolved in 7 mL of dioxane and the resulting solution was added to the reaction mixture. The mixture was stirred at room temperature for 6 h and partitioned between 100 ml of $H_2O$ and 3×100 mL of $CH_2Cl_2$. The combined organic layers were dried ($MgSO_4$), filtered, and concentrated to give 605 mg (64%) of compound 8 as a light yellow oil: $^1H$ NMR ($CDCl_3$) δ1.45 (s, 9H), 3.45 (m, 4H), 3.8–3.5 (m, 44H): MS (ESI) calculated for $C_{29}H_{59}NaNO_{14}$ (M+Na): 668. Found: 668.

Compound 9

Compound 8 (52 mg, 0.08 mmol) was dissolved in 3 mL of $CH_2Cl_2$ and 97 mg (0.483 mmol) of p-nitrophenylchloroformate was added to the mixture. The mixture was stirred at 0° C., 78 μL (0.966 mmol) of pyridine was added, and the mixture was then stirred at room temperature for 4 hours. The reaction mixture was cooled to 0° C., acidified with 1 N HCl, and partitioned between 10 mL of 1 N HCL and 3×10 mL of $CH_2Cl_2$. The combined organic layers were dried ($MgSO_4$), and concentrated to give 132 mg of an oil. Purification was accomplished by silica gel chromatography (98: 2 $CH_2Cl_2$/MeOH) to give 57 mg (74.0%) of compound 9 as an oil: $^1H$ NMR ($CDCl_3$) δ1.49 (s, 9H), 3.43 (m, 4H), 3.52–3.77 (m, 36H), 3.83 (m, 4H), 4.47 (m, 4H), 7.41 (d, 4H), 8.32 (d, 4H); MS (ESI) calculated for $C_{43}H_{65}NaN_3O_{22}$ (M+Na): 998. Found: 998.

Compound 10

Compound 9 (2.72 g, 2.79 mmol) was dissolved in 10 mL of $CH_2Cl_2$ and the mixture was stirred at 0° C. To the mixture was added 1.16 ml (8.36 mmol) of $Et_3N$ followed by 1.842 g (8.36 mmol) of mono-CBZ-piperazine dissolved in 10 mL of $CH_2Cl_2$. The mixture was stirred at room temperature for 18 hours, cooled to 0° C., and acidified with 1 N HCl. The mixture was partitioned between 150 mL of 1 N HCl and 3×150 mL of $CH_2Cl_2$. The combined organic layers were washed with saturated $NaHCO_3$ solution, dried ($MgSO_4$) and concentrated to give 3.64 g of a yellow oil. Purification by silica gel chromatography (97/3 $CH_2Cl_2$/MeOH) gave 3.1 g (98%) of compound 10 as a light yellow oil: $^1H$ NMR ($CDCl_3$) δ1.45 (s, 9H), 3.40–3.55 (m, 12H), 3.55–3.68 (m, 36H), 3.71 (m, 4H), 4.37 (m, 4H), 5.17 (s, 4H), 7.35 (brd s, 10H); MS (ESI) calculated for $C_{55}H_{87}NaN_5O_{20}$ (M+Na): 1060. Found: 1060.

Compound 11

Compound 10 (3.54 g, 3.11 mmol) was dissolved in 15 mL of $CH_2Cl_2$ and 15 mL of trifluoroacetic acid (TFA) was added to the mixture. The mixture was stirred at room temperature for 4 hours and concentrated. The residue was re-dissolved in 10 mL of $CH_2Cl_2$ and neutralized by shaking with a saturated solution of $NaHCO_3$ at 0° C.The mixture was then partitioned between 100 mL of saturated $NaHCO_3$ solution and 4×100 mL of $CH_2Cl_2$. The combined organic layers were dried ($MgSO_4$), filtered, and concentrated to give 3.16 g of compound 11 (98%) as a yellow oil: $^1H$ NMR ($CDCl_3$) δ2.88 (t, 4H), 3.50 (brd s, 16H), 3.56–3.69 (m, 36H), 3.71 (m, 4H), 4.28 (m, 4H), 5.15 (s, 4H), 7.38 (brd s, 10H); MS (ESI) calculated for $C_{50}H_{80}N_5O_{18}$ (M+H): 1037. Found: 1038.

Compound 12

Compound 9 (647 mg, 0.663 mmol) and 2.065 g (1.989 mmol) of compound 11 were dissolved in 3 mL of $CH_2Cl_2$, and 462 μL (3.315 mmol) of Et$_3$N and 40 mg (0.331 mmol) of DMAP (4-dimethylaminopyridine) was added to the mixture. The reaction mixture was stirred at room temperature overnight and cooled to 0° C. To the mixture was added 5 mL of H$_2$O, and the mixture was acidified with 1 N HCl and partitioned between 50 mL of H$_2$O and 3×50 mL of CH$_2$Cl$_2$. The combined organic layers were dried (MgSO$_4$) and concentrated to give 2.77 g (72.1 %) of a yellow oil. Purification by silica gel chromatography (CH$_2$Cl$_2$/MeOH) gave 1.307 g (72%) of compound 12 as a yellow oil: $^1$H NMR (CDCl$_3$) δ1.46 (s, 9H), 3.49 (brd s, 32H), 3.52–3.67 (m, 92H), 3.69 (m, 8H), 4.22 (m, 12H), 5.15 (s, 8H), 7.35 (brd s, 20H).

Compound 13

Compound 12 (1.3 g, 0.47 mmol) of the starting material was dissolved in 10 mL of CH$_2$Cl$_2$ and 10 mL of TFA (trifluoroacetic acid) was added. The mixture was stirred at room temperature for 4 hours, concentrated, and re-dissolved in 10 mL of CH$_2$Cl$_2$. The mixture was neutralized shaking with a saturated solution of NaHCO$_3$ at 0° C.The mixture was partitioned between 25 mL of saturated NaHCO$_3$ solution and 4×25 mL of CH$_2$Cl$_2$. The combined organic layers were dried (MgSO$_4$) and concentrated to give 1.23 g (98%) of compound 13 as a yellow oil: $^1$H NMR (CDCl$_3$) δ3.48 (brd s, 32H), 3.53–3.67 (m, 92H), 3.71 (m, 8H), 4.22 (m, 12H), 5.15 (s, 8H), 7.38 (brd s, 20H).

Compound 14

Compound 13 (600 mg, 0.224 mmol) was dissolved in 1.5 mL of CH$_2$Cl$_2$ and the mixture was stirred at 0° C. To the mixture was added 65 μL (0.373 mmol) of DIPEA followed by the slow addition of a solution of 20.5 mg (0.075 mmol) of triethyleneglycol bis-chloroformate dissolved in 0.5 mL of CH$_2$Cl$_2$. After 3 hours the reaction mixture was cooled to 0° C. and acidified with 1 N HCl. The mixture was partitioned between 25 ml of 1 N HCl and 2×25 ml of CH$_2$Cl$_2$. The combined organic layers were dried (MgSO$_4$) and concentrated to give 566 mg of a light yellow oil. Purification by silica gel chromatography (95/5 CH$_2$Cl$_2$/MeOH) gave 145 mg of compound 14 (35%) as a light yellow oil: $^1$H NMR (CDCl$_3$) δ3.51 (brd s, 64H), 3.54–3.77 (m, 272H), 4.23 (m, 28H), 5.17 (s, 16H), 7.36 (brd s, 40H); MS (ESI) calculated for C$_{260}$H$_{421}$N$_{22}$O$_{,06}$ (M+H): 5549. Found: 5549.

Compound 15

Compound 14 (143 mg, 0.026 mmol) was treated with 3 mL of 30% HBr/AcOH for 30 min. The resulting HBr salt was precipitated with ether. The solids were collected by centrifugation and washed three times with ether. The resulting HBr salt was dried in the desiccator overnight and dissolved in 1.2 ml of H$_2$O. The mixture was stirred at 0° C., and 97 mg (1.16 mmol) of sodium bicarbonate was added. A solution of 107 mg (0.412 mmol) of bromoacetic anhydride in 1.2 mL of dioxane was added, the mixture was stirred at 0° C. for 15–20 min. To the mixture was added 10 mL of H$_2$O, and the mixture was slowly acidified with 1 M H$_2$SO$_4$ to a pH of 4. The aqueous layer was extracted with 2×10 mL of EtOAc which was discarded. The aqueous layer was then extracted with 6×10 mL of 8/2 CH$_2$Cl$_2$/MeOH. The combined organic layers were dried (MgSO$_4$), filtered and concentrated to give 117 mg of an oil. Preparative HPLC (C18, gradient, 35–55% B, A =0.1% TFA/H$_2$O and B=0.1% TFA/CH$_3$CN) to give 27 mg (19%) of compound 15 as a colorless oil: $^1$H NMR (CDCl$_3$) 3.46–3.75 (m, 336H), 3.90 (m, 16H), 4.21–4.33 (m, 28H); MS (ESI) calculated for C$_{212}$H$_{381}$Br$_8$N$_{22}$O$_{98}$ (M+H): 5435. Found: 5448.

Example 3

Synthesis of Octamer of DEGA/TEG Using Segmental Approach

Figure 12A:
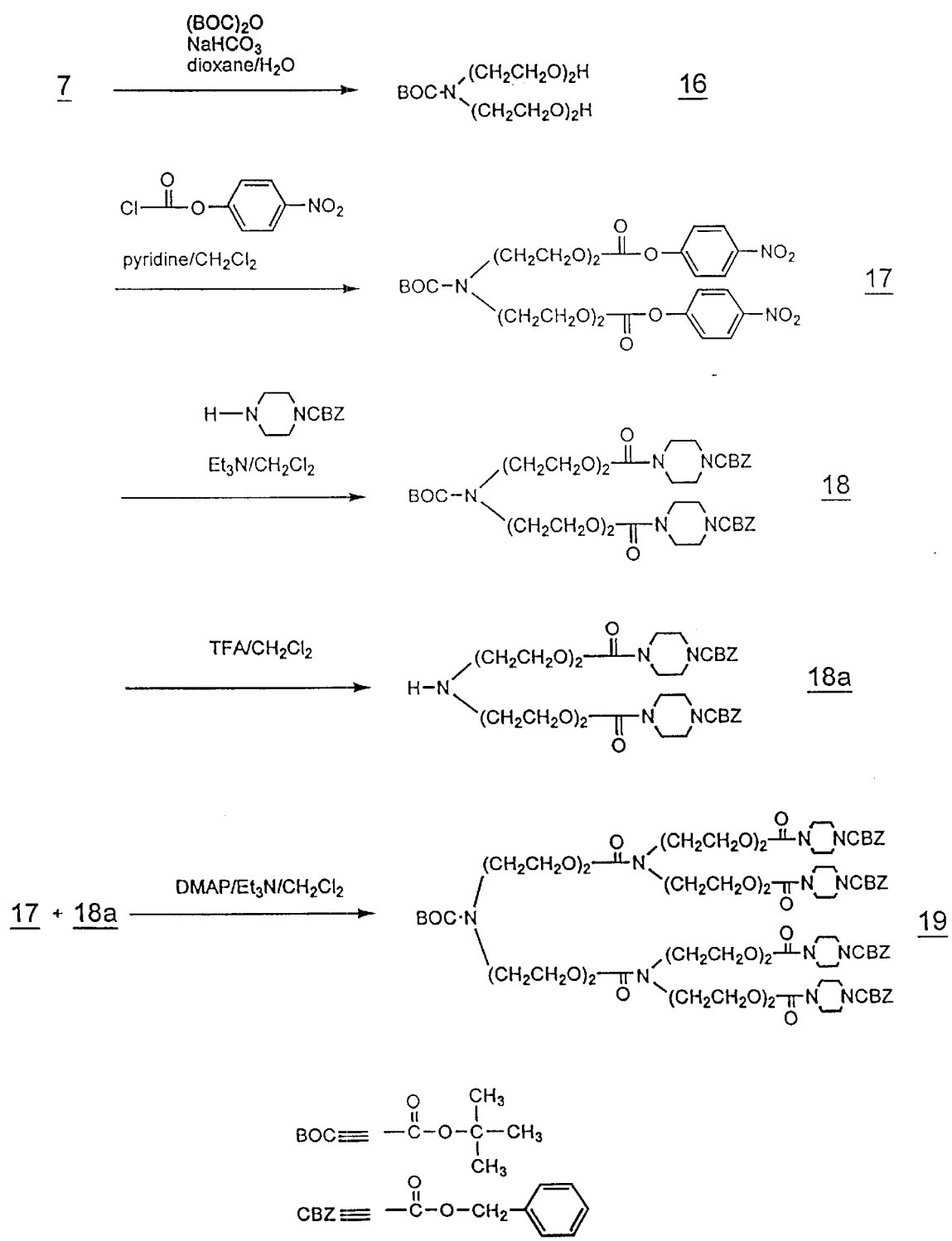
FIGS. 12A and 12B show synthetic schemes for the preparation of valency platform molecules of the present invention.
Figure 12B:
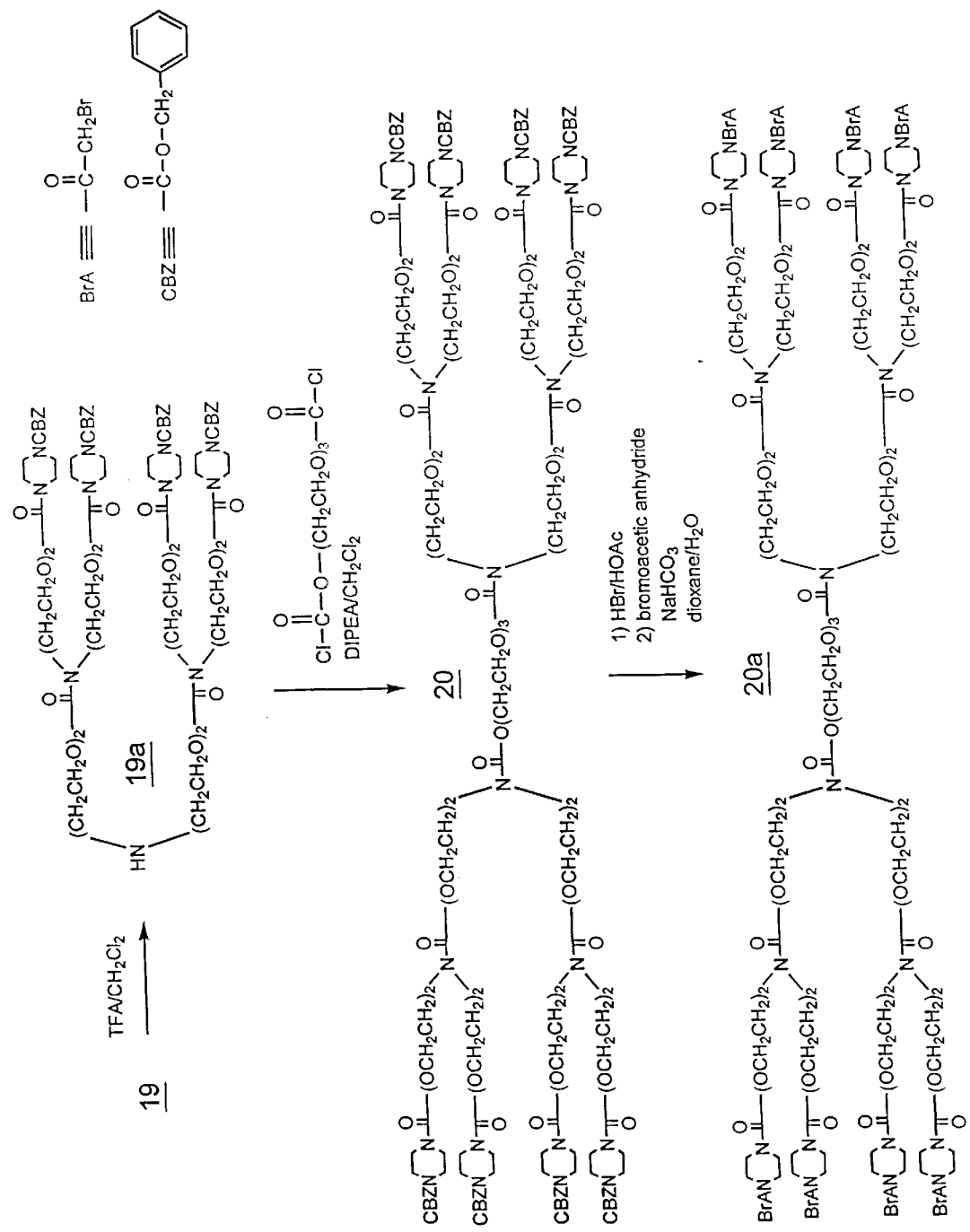

A chemical scheme for the preparation of an octamer of DEGA/TEG is shown in FIGS. 12A and 12B. The bis-diethyleneglycolamine (compound 7) was reacted with di-tert-butyldicarbonate to yield the N—BOC compound (compound 16), which was then reacted with para-nitrophenylchloroformate to yield the para-nitrophenylcarbonate compound (compound 17). The para-nitrophenylcarbonate (PNP) group was then converted to a carbamate group by reaction with mono-CBZ-protected piperazine, yielding compound 18. The BOC group was removed using trifluoroacetic acid to yield compound 18a. Compounds 17 and 18a were then reacted together to form a "one-sided" dendritic compound (compound 19). Again, the BOC group was removed using trifluoroacetic acid to yield compound 19a. Compound 19a was then reacted with triethyleneglycol bis chloroformate (from which the "core" is derived) to yield the "two-sided" dendritic compound (compound 20). The terminal CBZ-protected amino groups were then converted to the hydrobromide salt of amino group, and further reacted with bromoacetic anhydride to yield reactive bromoacetyl groups at each of the termini in compound 20a.

Compound 16

N—BOC—N,N-bis-diethyleneglycol-amine

To a solution of 600 mg ( 3.10 mmol) of bis-diethyleneglycolamine (compound 7) in 9.9 mL of 10% aqueous Na$_2$CO$_3$ was added slowly a solution of 678 mg (3.10 mmol) of di-tert-butyldicarbonate in 5 mL of dioxane. The mixture was stirred at room temperature for 5 hours, and 25 mL of water was added. The mixture was shaken with Et$_2$O, the Et$_2$O layer was discarded, and the mixture was extracted with three 25 mL portions of CH$_2$Cl$_2$. The CH$_2$Cl$_2$ extracts were combined, dried (MgSO$_4$), filtered and concentrated to give 717 mg (79%) of compound 16 as a viscous oil: $^1$H NMR (CDCl$_3$) δ1.48 (s, 9H), 3.45 (brd s, 4H), 3.60 (t, 4H), 3.65 (brd s, 4H), 3.69 (brd s, 4H).

Compound 17

To a solution of 200 mg (0.68 mmol) of compound 16 and 822 mg g (4.08 mmol) of 4-nitrophenylchloroformate in 30 mL of CH$_2$Cl$_2$ was added 0.66 mL (8.16 mmol) of pyridine at 0° C.The mixture was stirred at room temperature for 1.5 hours then cooled back to 0° C., and the mixture was acidified with 1 N HCl and partitioned between 50 mL of 1 N HCl and three 50 mL portions of CH$_2$Cl$_2$. The combined CH$_2$Cl$_2$ extracts were dried (MgSO$_4$), filtered and concentrated to give 1.21 g of yellow oil. The mixture was partially purified by silica gel chromatography (CH$_2$Cl$_2$/MeOH) to give 581 mg of partially purified compound 17 which still contained 4-nitrophenol: MS (ESI) calculated for C$_{27}$H$_{33}$NaN$_3$O$_4$ (M+Na): 646. Found: 646. This material was used directly in the next step.

Compound 18

To a solution of 421 mg of partially purified compound 17 (0.68 mmol theoretical) and 282 μL (2.02 mmol) of Et$_3$N in 4 mL of CH$_2$Cl$_2$ at 0° C. was added a solution of 446 m mmol) of mono-CBZ-piperazine in 4 mL of CH$_2$Cl$_2$. The mixture was stirred at room temperature for 1.5 hours, cooled back to 0° C., acidified with 1 N HCl, and partitioned between 50 mL of 1 N HCl and 3×50 mL of CH$_2$Cl$_2$. The combined CH$_2$Cl$_2$ layers were washed with saturated NaHCO$_3$ solution, dried (MgSO$_4$), filtered, and concentrated to give 500 mg of viscous residue. Purification by silica gel chromatography (CH$_2$Cl$_2$/MeOH) gave 265 mg (50%) of compound 18 as a viscous oil: $^1$H NMR (CDCl$_3$) δ1.45 (s, 9H), 3.40–3.70 (m, 28H), 4.28 (t, 4H), 5.16 (s, 4H), 7.37 (brd s, 10H); MS (ESI) calculated for C$_{39}$H$_{55}$NaN$_5$O$_{12}$ (M+Na): 808. Found: 809.

Compound 19

Compound 18 (77 mg, 0.098 mmol) was dissolved in 1.5 mL of CH$_2$Cl$_2$ and 1.5 mL of TFA was added. The mixture was stirred for 6 hours and concentrated. The residue was dissolved in 10 mL of CH$_2$Cl$_2$ and the resulting solution was stirred at 0° C. while 15 mL of saturated NaHCO$_3$ solution was added. The aqueous layer was extracted with 4×10 mL of CH$_2$Cl$_2$, and the combined organic layers were dried (MgSO$_4$), filtered, and concentrated to give 62 mg (92%) of free amine, compound 18a: $^1$H NMR (CDCl$_3$) δ2.90 (t, 4H), 3.46 (brd s, 16H), 3.66 (m, 8H), 4.25 (t, 4H), 5.16 (s, 4H), 7.36 (brd s, 10H). To a solution of compound 17 in CH$_2$Cl$_2$ is added the free amine, compound 18a (3 eq.) and pyridine. The mixture is stirred at room temperature until the reaction appears done by TLC. The product is isolated by extractive workup and purification by silica gel chromatography to give compound 19.

Compound 20

Compound 19 is dissolved in 1/1 CH$_2$Cl$_2$/TFA, and stirred at room temperature for 1 hour. The mixture is concentrated under vacuum to provide an amine intermediate, compound 19a. Two equivalents of the intermediate amine is reacted with triethyleneglycol bis-chloroformate in CH$_2$Cl$_2$ and pyridine. The product is isolated by extractive workup and purification by silica gel chromatography to give compound 20.

Compound 20a

In a process similar to that described above for compound 15, compound 20 is treated with 30% HBr/AcOH for 30 min. The resulting HBr salt is precipitated with ether. The solids are collected by centrifugation and washed with ether. The resulting HBr salt is dried in the desiccator overnight and dissolved in H$_2$O. The mixture was stirred at 0° C. and sodium bicarbonate added. A solution of bromoacetic anhydride in dioxane is added, and the mixture stirred at 0° C. for 15–20 min. To the mixture is added H$_2$O, and the mixture is slowly acidified with 1 M H$_2$SO$_4$ to a pH of 4. The aqueous layer is extracted with EtOAc which was discarded. The aqueous layer is then extracted with 8/2 CH$_2$Cl$_2$/MeOH. The combined organic layers are dried (MgSO$_4$), filtered and concentrated to give compound 20a.

Example 4

Synthesis of Tetramer of DEGA/TEG Using Core Propagation Approach

Figure 13:
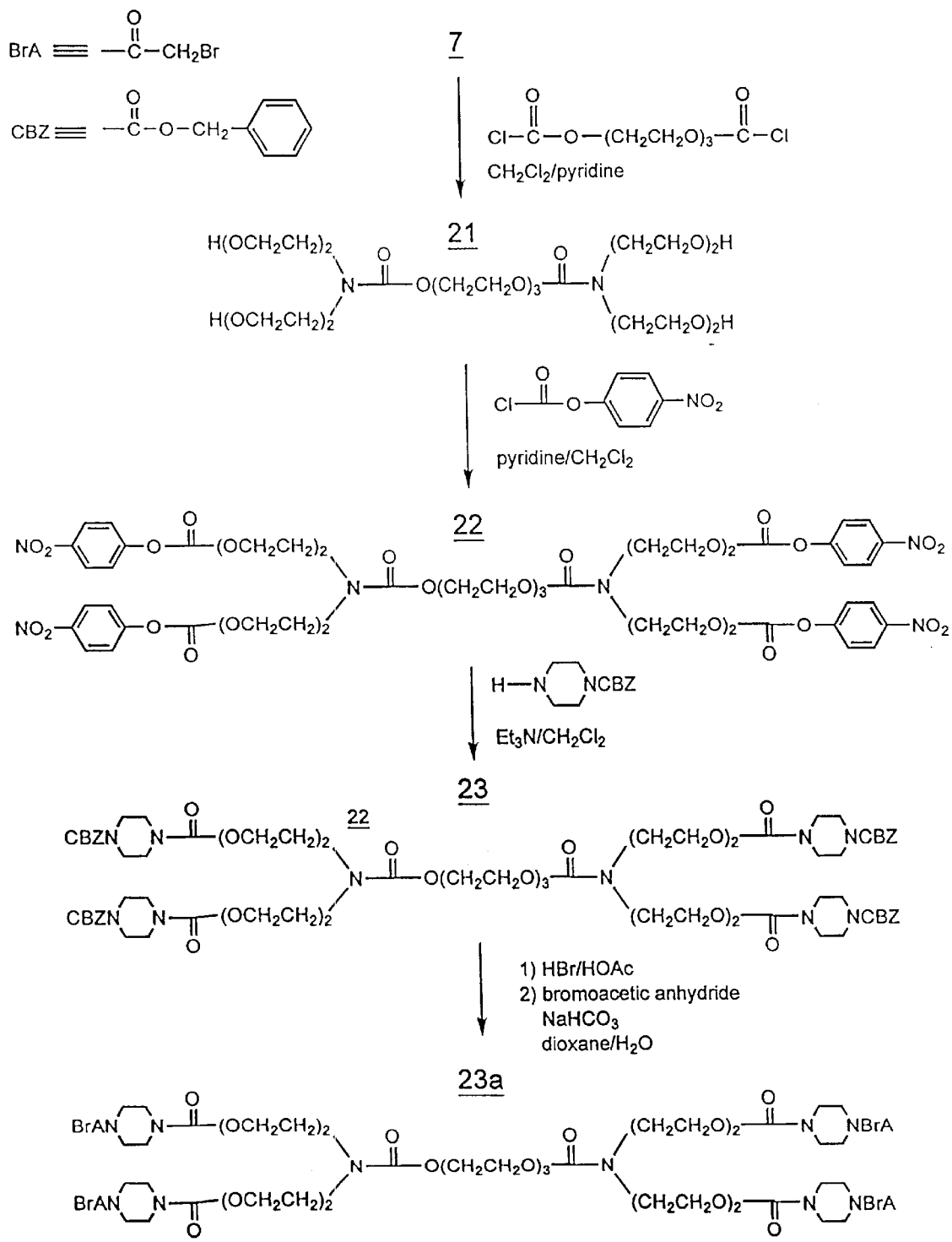
FIG. 13 shows a synthetic schemes for the preparation of valency platform molecules of the present invention.

A chemical scheme for the preparation of an tetramer of DEGA/TEG is shown in FIG. 13. The bis-diethyleneglycolamine (compound 7) was reacted triethyleneglycol bis chloroformate (from which the "core" is derived) to yield the tetrahydroxy compound, compound 21. Compound 21 was then reacted with para-nitrophenylchloroformate to yield the tetrapara-nitrophenylcarbonate compound (compound 22). The para-nitrophenylcarbonate (PNP) group was then converted to a carbamate group by reaction with mono-CBZ-protected piperazine, yielding compound 23. The terminal CBZ-protected amino groups were then converted to the hydrobromide salt of amino group, and further reacted with bromoacetic anhydride to yield reactive bromoacetyl groups at each of the termini in compound 23a.

Compound 21

To a solution of 1.94 g (10.0 mmol) of compound 7 and 1.75 mL (1.30 g, 10.0 mmol) of Et$_3$N at 0° C. a solution of 980 μL (1.31 g, 4.78 mmol) of triethyleneglycol bis-chloroformate in 35 mL of CH$_2$Cl$_2$. The mixture was stirred for 3 hours at room temperature and concentrated to give 4.84 g of crude compound 21 which was used as is in the next step: $^1$H NMR (CDCl$_3$) δ3.10 (m, 4H), 3.45–3.78 (m, 32H), 4.24 (m, 4H).

Compound 22

Pyridine (9.3 mL, 114.7 mmol) was added to a stirred solution of 4.84 g of crude compound 21 (4.78 mmol theoretical) and 7.71 g (38.24 mmol) of 4-nitrophenylchloroformate at 0° C., and the mixture was stirred for 4 hours at room temperature. The mixture was cooled to 0° C. and acidified with 1 N HCl. The mixture was partitioned between 250 mL of 1 N HCl and 2×250 mL of CH$_2$Cl$_2$. The organic layers were combined, dried (MgSO$_4$), filtered and concentrated to give 9.81 g of crude product. Purification by silica gel chromatography (CH$_2$Cl$_2$/MeOH) gave 4.40 g (74%) of compound 22 as a sticky viscous oil: $^1$H NMR (CDCl$_3$) δ3.56 (m, 8H), 3.61–3.72 (m, 16H), 3.76 (m, 8H), 4.23 (t, 4H), 4.44 (t, 8H), 8.28, (d, 8H); HRMS (FAB) calculated for C$_{52}$H$_{60}$CsN$_6$O$_{30}$ (M+Cs): 1381.2408. Found: 1381.2476.

Compound 23

A solution of 106 mg (0.48 mmol) of mono-CBZ-piperazine in 0.5 mL of CH$_2$Cl$_2$ was added to a stirred solution of 100 mg (0.08 mmol) of compound 22 and 67 μL (0.48 mmol) of Et$_3$N at 0° C. The mixture was stirred for 18 hours at room temperature, cooled to 0° C., and acidified with 1 N HCl. The mixture was partitioned between 5 mL of 1 N HCl and 3×5 mL of CH$_2$Cl$_2$. The organic layers were combined, washed with saturated NaHCO$_3$ solution, dried (MgSO$_4$), filtered, and concentrated to give 119 mg of yellow oil. Purification by silica gel chromatography (CH$_2$Cl$_2$/MeOH) gave 81 mg (64%) of compound 23 as a viscous oil: $^1$H NMR (CDCl$_3$) δ3.48 (brd s, 40H), 3.52–3.74 (m, 24H), 4.24 (t, 12H), 5.14 (s, 8H), 7.35 (brd s, 20H); HRMS (FAB) calculated for C$_{76}$H$_{104}$CsN$_6$O$_{30}$ (M+Cs): 1705.6178. Found: 1705.6269.

Compound 23a

In a process similar to that described above for compound 15, compound 23 is treated with 30% HBr/AcOH for 30 min. The resulting HBr salt is precipitated with ether. The solids are collected by centrifugation and washed with ether. The resulting HBr salt is dried in the desiccator overnight and dissolved in H$_2$O. The mixture was stirred at 0° C. and sodium bicarbonate added. A solution of bromoacetic anhydride in dioxane is added, and the mixture stirred at 0° C. for 15–20 min. To the mixture is added H$_2$O, and the mixture is slowly acidified with 1 M H$_2$SO$_4$ to a pH of 4. The aqueous layer is extracted with EtOAc which was discarded. The aqueous layer is then extracted with 8/2 CH$_2$Cl$_2$/MeOH. The combined organic layers are dried (MgSO$_4$), filtered and concentrated to give compound 23a.

Figure 14A:
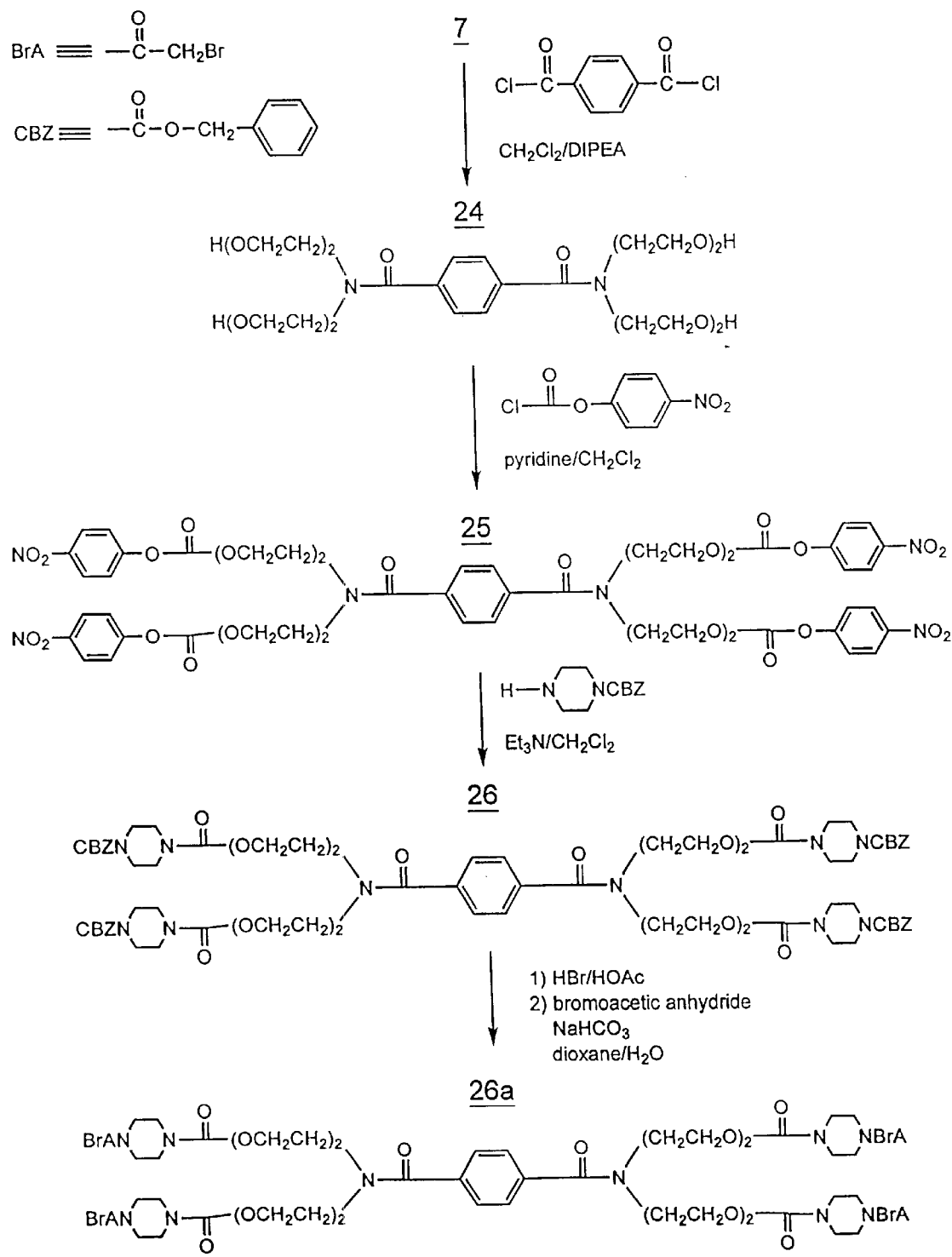
FIGS. 14A and 14B show synthetic schemes for the preparation of valency platform molecules of the present invention.

Example 5
Synthesis of Tetramer of DEGA/PTH Using Core Propagation Approach A chemical scheme for the preparation of an tetramer of DEGA/PTH is shown in FIG. 14A. The bis-diethyleneglycolamine (compound 7) was reacted with terephthaloyl chloride (from which the "core" is derived) to yield the tetrahydroxy compound, compound 24. Compound 24 was then reacted with para-nitrophenylchloroformate to yield the tetra para-nitrophenylcarbonate compound (compound 25). The para-nitrophenylcarbonate (PNP) group was then converted to a carbamate group by reaction with mono-CBZ-protected piperazine, yielding compound 26. The terminal CBZ-protected amino groups were then converted to the hydrobromide salt of amino group, and further reacted with bromoacetic anhydride to yield reactive bromoacetyl groups at each of the termini in compound 26a.

Compound 24

A solution of 300 mg (1.48 mmol) of terephthaloyl chloride in 9 mL of CH$_2$Cl$_2$ was slowly added to a 0° C. solution of 600 mg (3.10 mmol) of 7 and 540 µL (3.10 mmol) of diisopropylethylamine in 12 mL of CH$_2$Cl$_2$, and the mixture was stirred under nitrogen atmosphere for 3 hours at room temperature. The mixture was concentrated under vacuum to give 1.53 g of a crude mixture which contained 24.

Compound 25

The 1.53 g of crude 24 and 2.38 g (1 1.81 mmol) of 4-nitrophenylchloroformate were dissolved in 30 mL of pyridine, and the resulting solution was stirred at 0° C. while 1.91 mL (23.62 mmol) of pyridine was added. The mixture was stirred at room temperature for 4 hours, cooled to 0° C., and acidified with 1 N HCL. The mixture was partitioned between 75 mL of 1 N HCl and 2×75 mL of CH$_2$Cl$_2$. The organic layers were combined, washed with saturated NaHCO$_3$ solution, dried (MgSO$_4$), filtered, and concentrated to give 2.75 g of an oil. Purification by silica gel chromatography (CH$_2$Cl$_2$/MeOH) gave 1.33 g (76%) of 25 as a viscous oil: $^1$H NMR (CDCl$_3$) δ3.52 (brd s, 8H), 3.65 (brd s, 4H), 3.81 (brd s, 12H), 4.41 (m 8H), 7.38 (m, 8H), 7.47 (s, 4H), 8.27 (m, 8H); HRMS (FAB) calculated for C$_{52}$H$_{53}$N$_6$O$_{26}$ (M+H): 1177.3010. Found: 1177.3062.

Compound 26

A solution of 113 mg (0.51 mmol) of mono-CBZ-piperazine in 0.5 mL of CH$_2$Cl$_2$ was added to a stirred solution of 100 mg (0.085 mmol) of compound 25 and 71 µL (0.51 mmol) of Et$_3$N at 0° C. The mixture was stirred for 18 hours at room temperature, cooled to 0° C., and acidified with 1 N HCl. The mixture was partitioned between 5 mL of 1 N HCl and 3×5 mL of CH$_2$Cl$_2$. The organic layers were combined, washed with saturated NaHCO$_3$ solution, dried (MgSO$_4$), filtered, and concentrated to give 125 mg of yellow oil. Purification by silica gel chromatography (CH$_2$Cl$_2$/MeOH) gave 59 mg (46%) of 26 as a viscous oil: $^1$H NMR (CDCl$_3$) δ3.45 (brd s, 40H), 3.55 (m, 4H), 3.72 (m, 4H), 3.78 (s, 8H), 4.24 (m, 8H), 5.13 (s,8H), 7.34 (brd s, 20H), 7.42 (s, 4H); HRMS (FAB) calculated for C$_{76}$H$_{96}$CsN$_{10}$O$_{22}$ (M+Cs): 1633.5755. Found: 1633.5846.

Compound 26a

In a process similar to that described above for compound 15, compound 26 is treated with 30% HBr/AcOH for 30 min. The resulting HBr salt is precipitated with ether. The solids are collected by centrifugation and washed with ether. The resulting HBr salt is dried in the desiccator overnight and dissolved in H$_2$O. The mixture was stirred at 0° C. and sodium bicarbonate added. A solution of bromoacetic anhydride in dioxane is added, and the mixture stirred at 0° C. for 15–20 min. To the mixture is added H$_2$O, and the mixture is slowly acidified with 1 M H$_2$SO$_4$ to a pH of 4. The aqueous layer is extracted with EtOAc which was discarded. The aqueous layer is then extracted with 8/2 CH$_2$Cl$_2$/MeOH. The combined organic layers are dried (MgSO$_4$), filtered and concentrated to give compound 26a.

Figure 14B:
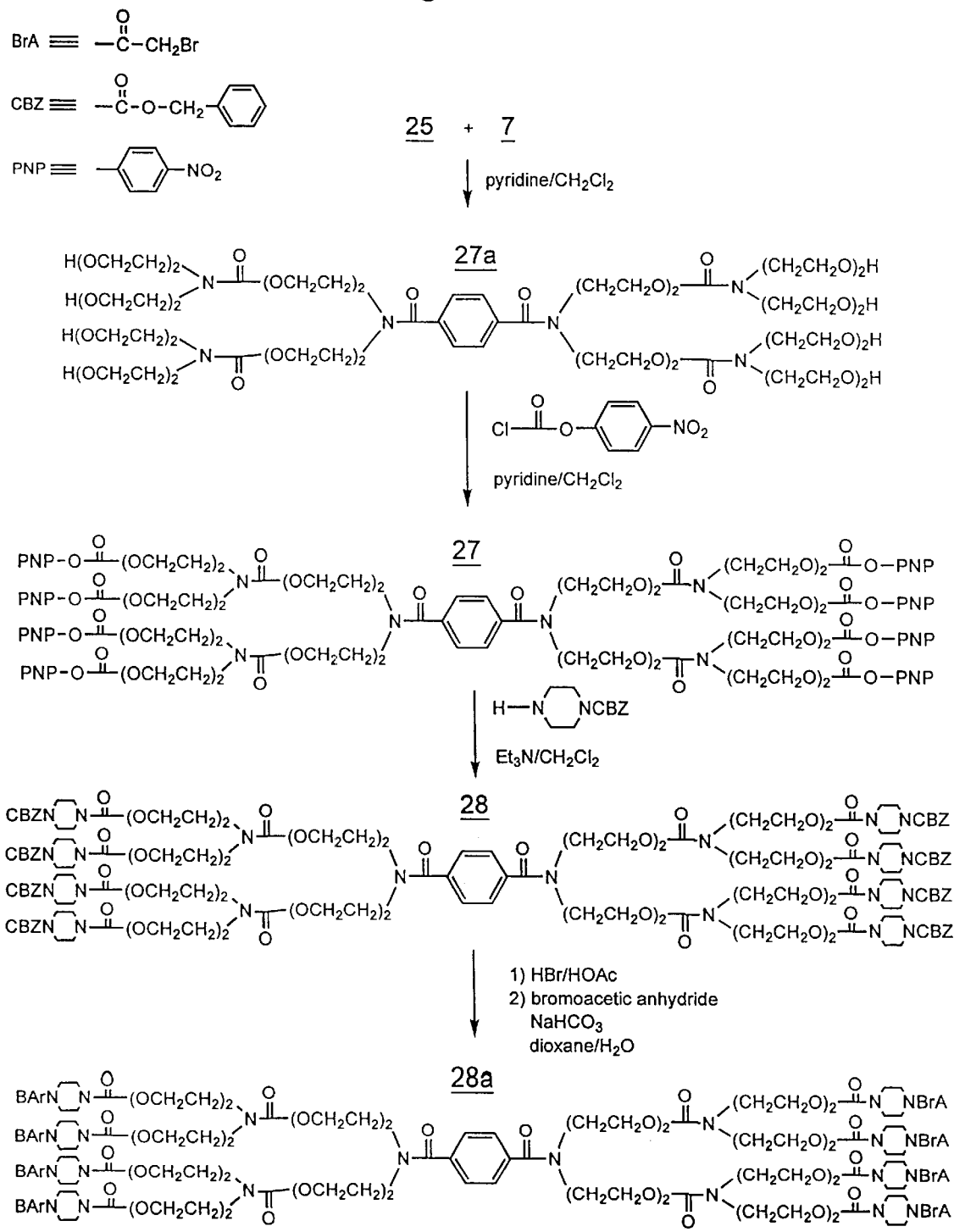

Example 6
Synthesis of Octamer of DEGA/PTH Using Core Propagation Approach A chemical scheme for the preparation of an octamer of DEGA/PTH is shown in FIG. 14B. The bis-diethyleneglycolamine (compound 7) was reacted with the tetra para-nitrophenylcarbonate compound (compound 25) to yield the octahydroxy compound, compound 27a. Compound 27a was then reacted with para-nitrophenylchloroformate to yield the octapara-nitrophenylcarbonate compound (compound 27). The para-nitrophenylcarbonate (PNP) group was then converted to a carbamate group by reaction with mono-CBZ-protected piperazine, yielding compound 28. The terminal CBZ-protected amino groups were then converted to the hydrobromide salt of amino group, and further reacted with bromoacetic anhydride to yield reactive bromoacetyl groups at each of the termini in compound 28a.

Compound 27a

A solution of 98 mg (0.51 mmol) of compound 7 in 0.5 mL of CH$_2$°Cl$_2$ was added to a stirred solution of 100 mg (0.085 mmol) of compound 25 and 71 µL (0.51 mmol) of Et$_3$N at 0° C., and the mixture was stirred for 18 hours. The mixture was concentrated to give 250 mg of crude product, compound 27a.

Compound 27

Crude compound 27a (250 mg) was dissolved in 4 mL of CH$_2$°Cl$_2$. The mixture was cooled to 0° C., and 275 mg (1.36 mmol) of 4-nitrophenylchloroformate was added followed by 220 µL (2.74 mmol) of pyridine. The mixture was stirred at room temperature for 7 hours, cooled to 0° C., and acidified with 1 N HCl. The mixture was partitioned between 5 mL of 1 N HCl and 2×15 mL of CH$_2$Cl$_2$. The organic layers were combined, washed with saturated NaHCO$_3$ solution, dried (MgSO$_4$), filtered, and concentrated to give 393 mg of an oil. Purification by silica gel chromatography (CH$_2$Cl$_2$/MeOH) gave 123 mg (53%) of compound 27 as a viscous oil: $^1$H NMR (CDCl$_3$) δ3.63–3.86 (m, 72H), 4.46 (t, 24H), 7.26 (s, 4H), 7.35 (m, 16H), 8.24 (m, 16H).

Compound 28

A solution of 6 eq. of mono-CBZ-piperazine in CH$_2$Cl$_2$ is added to a stirred solution of compound 27 and 6 eq. of Et$_3$N at 0° C.The mixture is stirred for 18 hours at room temperature, cooled to 0° C., and acidified with 1 N HCl. The mixture is partitioned between 1 N HCl and CH$_2$Cl$_2$. The organic layers are combined, washed with saturated NaHCO$_3$ solution, dried (MgSO$_4$), filtered, and concentrated to give crude product which can be purified by silica gel chromatography to give compound 28.

Compound 28a

In a process similar to that described above for compound 15, compound 28 is treated with 30% HBr/AcOH for 30 min. The resulting HBr salt is precipitated with ether. The solids are collected by centrifugation and washed with ether. The resulting HBr salt is dried in the desiccator overnight and dissolved in $H_2O$. The mixture was stirred at 0° C. and sodium bicarbonate added. A solution of bromoacetic anhydride in dioxane is added, and the mixture stirred at 0° C. for 15–20 min. To the mixture is added $H_2O$, and the mixture is slowly acidified with 1 M $H_2SO_4$ to a pH of 4. The aqueous layer is extracted with EtOAc which was discarded. The aqueous layer is then extracted with 8/2 $CH_2Cl_2$/MeOH. The combined organic layers are dried ($MgSO_4$), filtered and concentrated to give compound 28a.

Example 7

Synthesis of Tetramer of HEGA/TEG Using Core Propagation Approach

Figure 15:
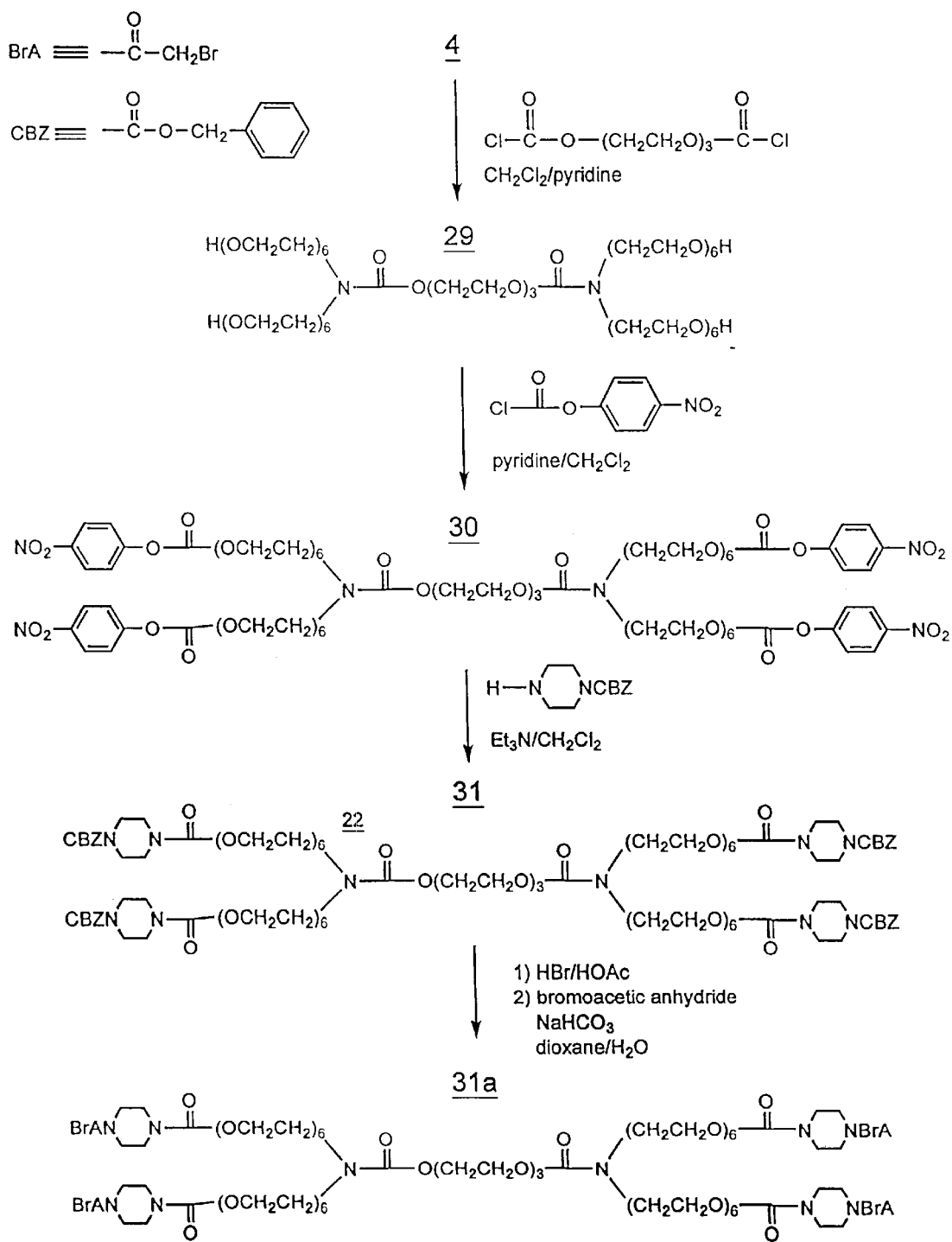
FIG. 15 shows a synthetic schemes for the preparation of valency platform molecules of the present invention.

A chemical scheme for the preparation of an tetramer of HEGA/TEG is shown in FIG. 15. The bis-hexaethyleneglycolamine (compound 7) was reacted triethyleneglycol bis chloroformate (from which the "core" is derived) to yield the tetrahydroxy compound, compound 29. Compound 29 was then reacted with para-nitrophenylchloroformate to yield the tetraparanitrophenylcarbonate compound (compound 30). The para-nitrophenylcarbonate (PNP) group was then converted to a carbamate group by reaction with mono-CBZ-protected piperazine, yielding compound 31. The terminal CBZ-protected amino groups were then converted to the hydrobromide salt of amino group, and further reacted with bromoacetic anhydride to yield reactive bromoacetyl groups at each of the termini in compound 31a.

Compound 29

To a solution of 2.1 eq. of compound 4 and 2.1 eq. of $Et_3N$ at 0° C. is added a solution of 1 eq. of triethyleneglycol bis-chloroformate in $CH_2Cl_2$. The mixture is stirred at room temperature until complete by TLC and concentrated to give crude compound 29 which is used as is in the next step.

Compound 30

Pyridine (12 eq.) is added to a stirred solution of crude compound 29 and 6 eq. of 4-nitrophenylchloroformate at 0° C., and the mixture is stirred at room temperature until the reaction is complete as evidenced by TLC. The mixture is cooled to 0° C., and acidified with 1 N HCl. The mixture is partitioned between 1 N HCl and $CH_2Cl_2$. The organic layers are combined, dried ($MgSO_4$), filtered and concentrated to give crude product. Compound 30 is purified by silica gel chromatography.

Compound 31

A solution of 6 eq. of mono-CBZ-piperazine in $CH_2Cl_2$ is added to a stirred solution of compound 30 and 6 eq. of $Et_3N$ at 0° C. The mixture is stirred for at room temperature until the reaction is complete as evidenced by TLC, cooled to 0° C., and acidified with 1 N HCl. The mixture is partitioned between 1 N HCl and $CH_2Cl_2$. The organic layers are combined, washed with saturated $NaHCO_3$ solution, dried ($MgSO_4$), filtered, and concentrated to give crude compound 31 which is purified by silica gel chromatography.

Compound 31a

In a process similar to that described above for compound 15, compound 31 is treated with 30% HBr/AcOH for 30 min. The resulting HBr salt is precipitated with ether. The solids are collected by centrifugation and washed with ether. The resulting HBr salt is dried in the desiccator overnight and dissolved in $H_2O$. The mixture was stirred at 0° C. and sodium bicarbonate added. A solution of bromoacetic anhydride in dioxane is added, and the mixture stirred at 0° C. for 15–20 min. To the mixture is added $H_2O$, and the mixture is slowly acidified with 1 M $H_2SO_4$ to a pH of 4. The aqueous layer is extracted with EtOAc which was discarded. The aqueous layer is then extracted with 8/2 $CH_2Cl_2$/MeOH. The combined organic layers are dried ($MgSO_4$), filtered and concentrated to give compound 31a.

Example 8

Synthesis of Tetramer of DEA/PTH Using Core Propagation Approach

Figure 16A:
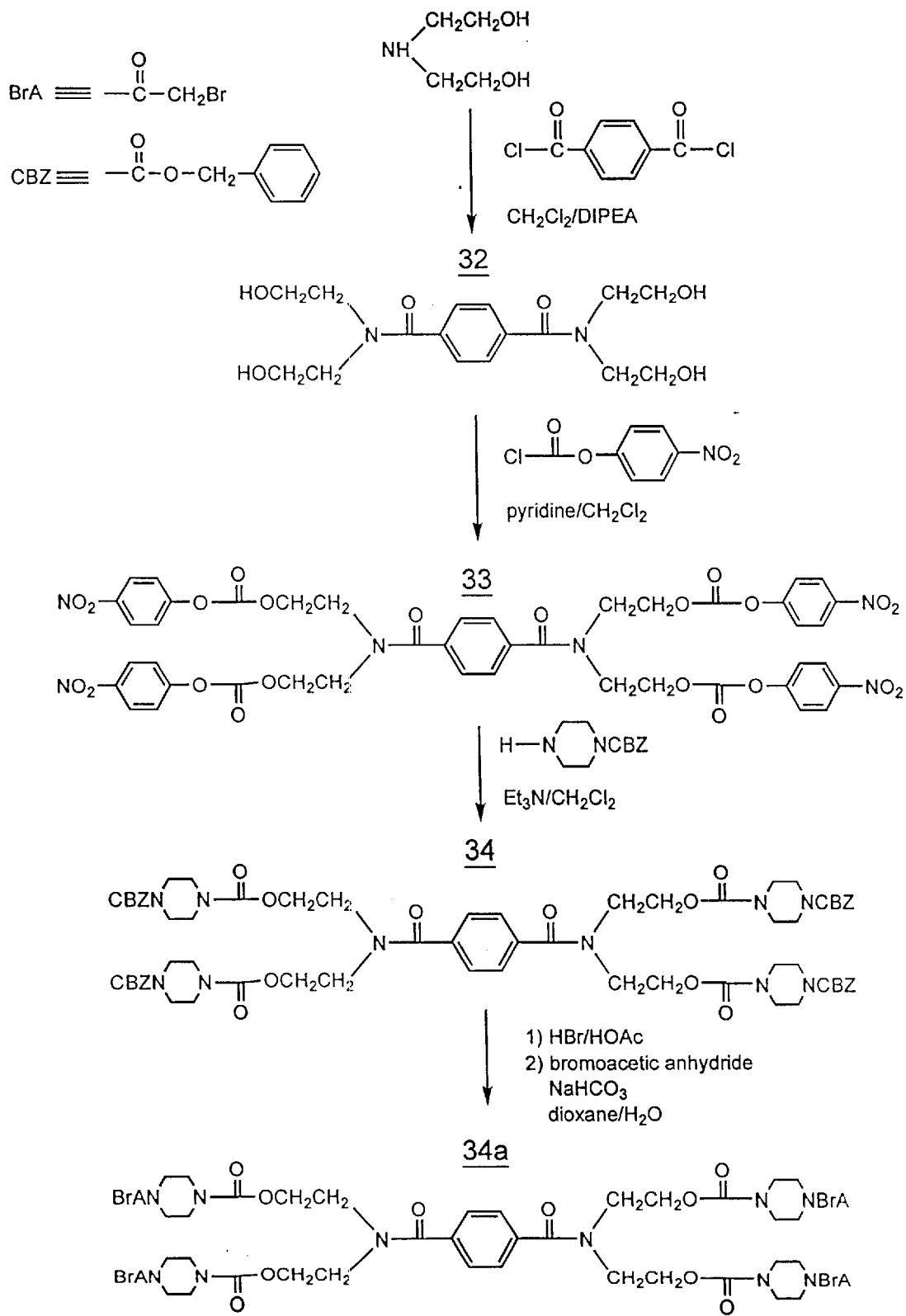
FIGS. 16A and 16B show synthetic schemes for the preparation of valency platform molecules of the present invention.

A chemical scheme for the preparation of an tetramer of DEGA/PTH is shown in FIG. 16A. Diethanolamine was reacted with terephthaloyl chloride (from which the "core" is derived) to yield the tetrahydroxy compound, compound 32. Compound 32 was then reacted with para-nitrophenylchloroformate to yield the tetra para-nitrophenylcarbonate compound (compound 33). The para-nitrophenylcarbonate (PNP) group was then converted to a carbamate group by reaction with mono-CBZ-protected piperazine, yielding compound 34. The terminal CBZ-protected amino groups were then converted to the hydrobromide salt of amino group, and further reacted with bromoacetic anhydride to yield reactive bromoacetyl groups at each of the termini in compound 34a.

Compound 32

A solution of 2.0 g (9.85 mmol) of terephthaloyl chloride in 25 mL of THF was added slowly to a 0° C. solution of 2.17 g (20.7 mmol) of diethanolamine and 3.6 mL (20.7 mmol) of diisopropylethylamine in 50 mL of THF. The mixture was stirred at room temperature for 3 hours and concentrated under vacuum to give 6.7 g of crude compound 32. A small amount was purified for characterization purposes by preparative HPLC (1" C 18 column, gradient 0–15% B, A=0.1% TFA/$H_2O$ and B=0.1% TFA/$CH_3CN$): $^1H$ NMR ($D_2O$) $\delta$3.52 (m, 4H), 3.59 (m, 4H), 3.72 (m, 4H), 3.89 (m, 4H), 7.51 (s, 4H); MS (ESI) calculated for $C_{16}H_{25}N_2O_6$(M+H): 341. Found: 341.

Compound 33

Pyridine (11.4 mL, 141.2 mmol) was slowly added to a stirred solution of 6.01 g (8.8 mmol theoretical) of crude compound 32 and 14.2 g (70.6 mmol) of 4-nitrophenylchloroformate in 88 mL of THF. The mixture was stirred at room temperature for 18 hours and acidified with 1 N HCl. The mixture was partitioned between 300 mL of 1 N HCl and 2×300 mL of $CH_2Cl_2$. The combined organic layers were washed with saturated $NaHCO_3$ solution, dried ($MgSO_4$), filtered, and concentrated to give 14.0 g of sticky orange oil. Purification by silica gel chromatography ($CH_2Cl_2$/MeOH) provided 3.34 g (38%) of compound 33 as a crystalline solid: mp 77–85° C.; $^1H$ NMR ($CDCl_3$) $\delta$3.76 (brd, 4H), 4.01 (brd, 4H), 4.38 (brd, 4H), 4.64 (brd, 4H), 7.36 (brd, 8H), 7.53 (s, 4H), 8.28 (m, 8H); $^{13}C$ NMR ($CDCl_3$) $\delta$45.0, 48.5, 65.9, 66.6, 121.8, 125.0, 125.4, 126.1, 127.2, 137.1, 145.6, 152.4, 155.2, 171.9; HRMS (FAB) calculated for $C_{44}H_{36}CsN_6O_{22}$ (M+Cs): 1133.0937. Found: 1133.0988.

Compound 34

A solution of 132 mg (0.6 mmol) of mono-CBZ-piperazine in 0.5 mL of $CH_2Cl_2$ was added to a 0° C.

solution of 100 mg (0.1 mmol) of compound 33 and 84 μL (0.6 mmol) of Et$_3$N in 0.5 mL of CH$_2$Cl$_2$. The reaction mixture was stirred for 18 hours at room temperature, cooled to 0° C., and acidified with 1 N HCl. The mixture was partitioned between 5 mL of 1 N HCl and 3×5 mL of CH$_2$Cl$_2$. The combined organic layers were washed with saturated NaHCO$_3$ solution, dried (MgSO$_4$), filtered, and concentrated to give 123 mg of white solid. Purification by silica gel chromatography (CH$_2$Cl$_2$/MeOH) provided 86 mg (65%) of compound 34 as a crystalline solid: mp 64–67° C.; 1H NMR (CDCl$_3$) δ3.35–3.63 (m, 36H), 3.86 (brd, 4H), 4.13 (brd, 4H), 4.41 (brd, 4H), 5.14 (s, 8H), 7.38 (brd s, 20H), 7.43 (s, 4H); $^{13}$C NMR (CDCl$_3$) δ43.5, 45.1, 48.4, 62.6, 67.4, 126.9, 128.0, 128.2, 128.5, 136.3, 137.4, 155.1, 171.4; HRMS (FAB) calculated for C$_{68}$H$_{80}$CsN$_{10}$O$_{18}$ (M+Cs): 1457.4706. Found: 1457.4781.

Compound 34a

In a process similar to that described above for compound 15, compound 34 is treated with 30% HBr/AcOH for 30 min. The resulting HBr salt is precipitated with ether. The solids are collected by centrifugation and washed with ether. The resulting HBr salt is dried in the desiccator overnight and dissolved in H$_2$O. The mixture was stirred at 0° C. and sodium bicarbonate added. A solution of bromoacetic anhydride in dioxane is added, and the mixture stirred at 0° C. for 15–20 min. To the mixture is added H$_2$O, and the mixture is slowly acidified with 1 M H$_2$SO$_4$ to a pH of 4. The aqueous layer is extracted with EtOAc which was discarded. The aqueous layer is then extracted with 8/2 CH$_2$Cl$_2$/MeOH. The combined organic layers are dried (MgSO$_4$), filtered and concentrated to give compound 34a.

Example 9

Synthesis of Octamer of DEA/PTH Using Core Propagation Approach

Figure 16B:
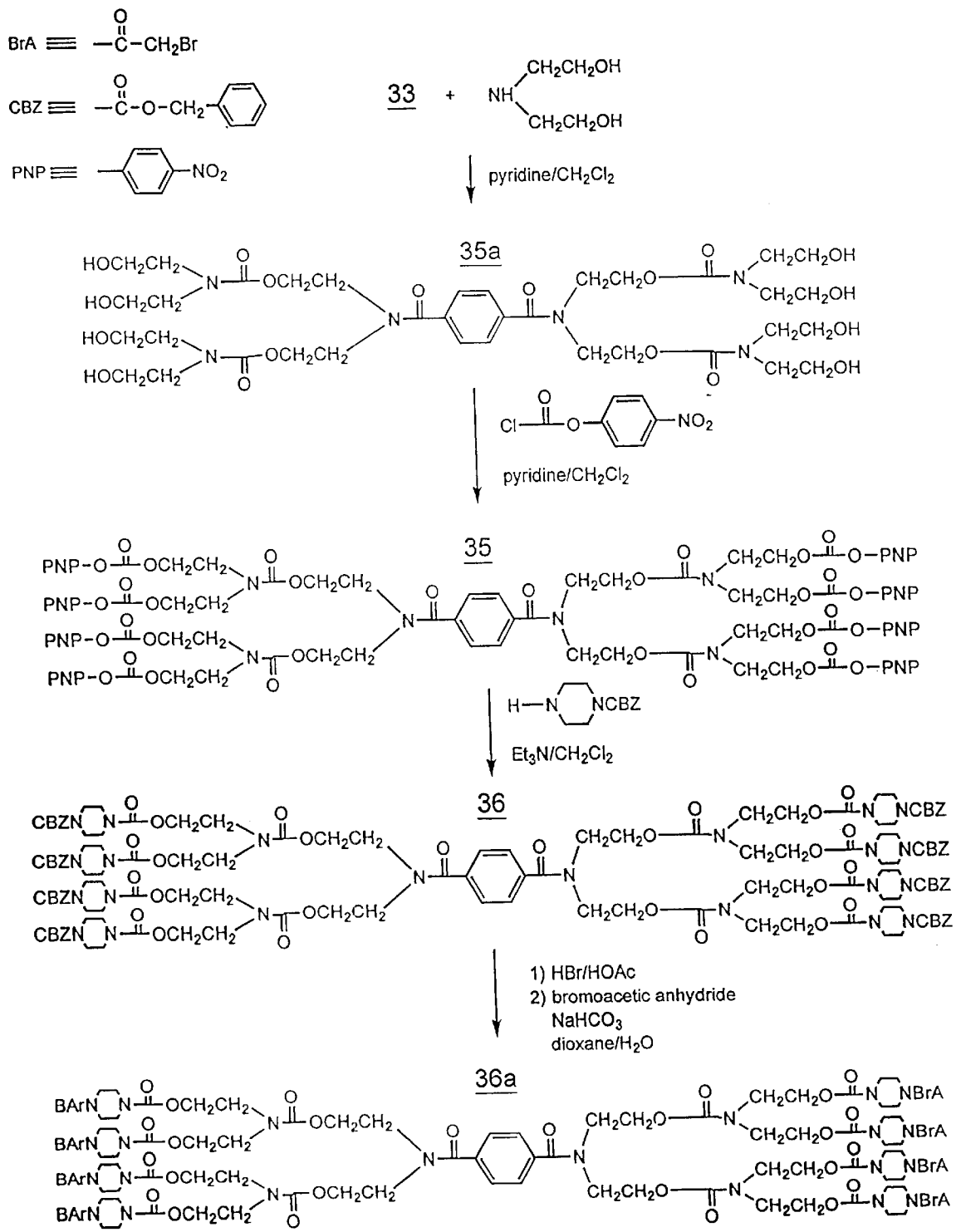

A chemical scheme for the preparation of an octamer of DEA/PTH is shown in FIG. 16B. Diethanolamine was reacted with the tetrapara-nitrophenylcarbonate compound (compound 33) to yield the octahydroxy compound, compound 35a. Compound 35a was then reacted with para-nitrophenylchloroformate to yield the octa para-nitrophenylcarbonate compound (compound 35). The para-nitrophenylcarbonate (PNP) group was then converted to a carbamate group by reaction with mono-CBZ-protected piperazine, yielding compound 36. The terminal CBZ-protected amino groups were then converted to the hydrobromide salt of amino group, and further reacted with bromoacetic anhydride to yield reactive bromoacetyl groups at each of the termini in compound 36a.

Compound 35a

A solution of 100 mg (0.1 mmol) of compound 33 in 450 μL of pyridine was slowly added to a 0° C. solution of 63 mg (0.6 mmol) of diethanolamine in 150 μL of pyridine. The mixture was stirred for 3 hours at room temperature and cooled back to 0° C., to yield crude compound 35a, which was used in the next step.

Compound 35

A solution of 443 mg (2.2 mmol) of 4-nitrophenylchloroformate was added to the reaction mixture above, and the mixture was stirred for 18 hours at room temperature. The mixture was then cooled to 0° C., and acidified with 1 N HCl, and partitioned between 15 mL of 1 N HCl and 2×15 mL of CH$_2$Cl$_2$. The combined organic layers were dried (MgSO$_4$), filtered, and concentrated to give 462 mg of white sticky solid. Purification by silica gel chromatography (CH$_2$Cl$_2$/MeOH) provided 141 mg (65%) of compound 35 as a crystalline solid: mp 75–80° C.; $^1$H NMR (CDCl3) δ3.52–3.81 (m, 20H), 3.89 (m, 4H), 4.12 (m, 4H), 4.36–4.59 (m, 20H), 7.42 (m, 20H), 8.30 (m, 16H).

Compound 36

A solution of 61 mg (0.276 mmol) of mono-CBZ-piperazine in 200 μL of CH$_2$Cl$_2$ was added to a 0° C. solution of 50 mg (0.023 mmol) of compound 35 and 39 μL (0.276 mmol) of Et$_3$N in 200 μL of CH$_2$Cl$_2$. The reaction mixture was stirred for 7 hours at room temperature, cooled to 0° C., and acidified with 1 N HCl. The mixture was partitioned between 10 mL of 1 N HCl and 3×10 mL of CH$_2$Cl$_2$. The combined organic layers were dried (MgSO$_4$), filtered, and concentrated to give 85 mg of yellow solid. Purification by silica gel chromatography (CH$_2$Cl$_2$/MeOH) provided 33 mg (51%) of compound 36 as a sticky low melting solid: $^1$H NMR (CDCl$_3$) δ3.37–3.72 (m, 84H), 3.84 (m, 4H), 4.03–4.29 (m, 20H), 4.35 (m, 4H), 5.14 (s, 16H), 7.35 (brd s, 40H), 7.44 (s, 4H); MS (MALDI) calculated for C$_{140}$H$_{172}$NaN$_{22}$O$_{42}$ (M+Na): 2856. Found: 2857.

Compound 36a

In a process similar to that described above for compound 15, compound 36 is treated with 30% HBr/AcOH for 30 min. The resulting HBr salt is precipitated with ether. The solids are collected by centrifugation and washed with ether. The resulting HBr salt is dried in the desiccator overnight and dissolved in H$_2$O. The mixture was stirred at 0° C. and sodium bicarbonate added. A solution of bromoacetic anhydride in dioxane is added, and the mixture stirred at 0° C. for 15–20 min. To the mixture is added H$_2$O, and the mixture is slowly acidified with 1 M H$_2$SO$_4$ to a pH of 4. The aqueous layer is extracted with EtOAc which was discarded. The aqueous layer is then extracted with 8/2 CH$_2$Cl$_2$/MeOH. The combined organic layers are dried (MgSO$_4$), filtered and concentrated to give compound 36a.

Example 10

Synthesis of Tetramer of DEA/DEG Using Core Propagation Approach

Figure 17A:
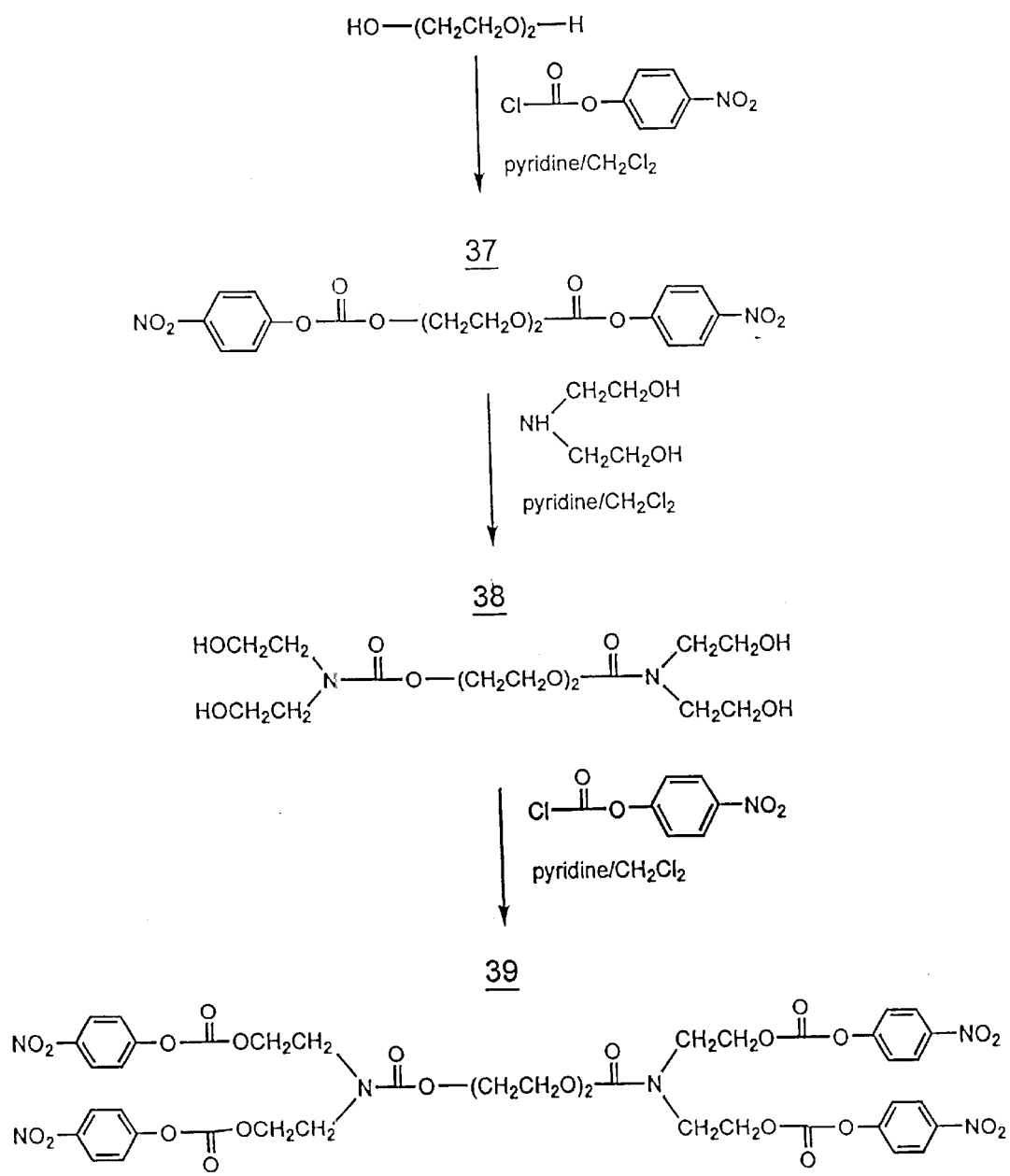
FIGS. 17A, 17B, 17C, and 17D show synthetic schemes for the preparation of valency platform molecules of the present invention.
Figure 17B:
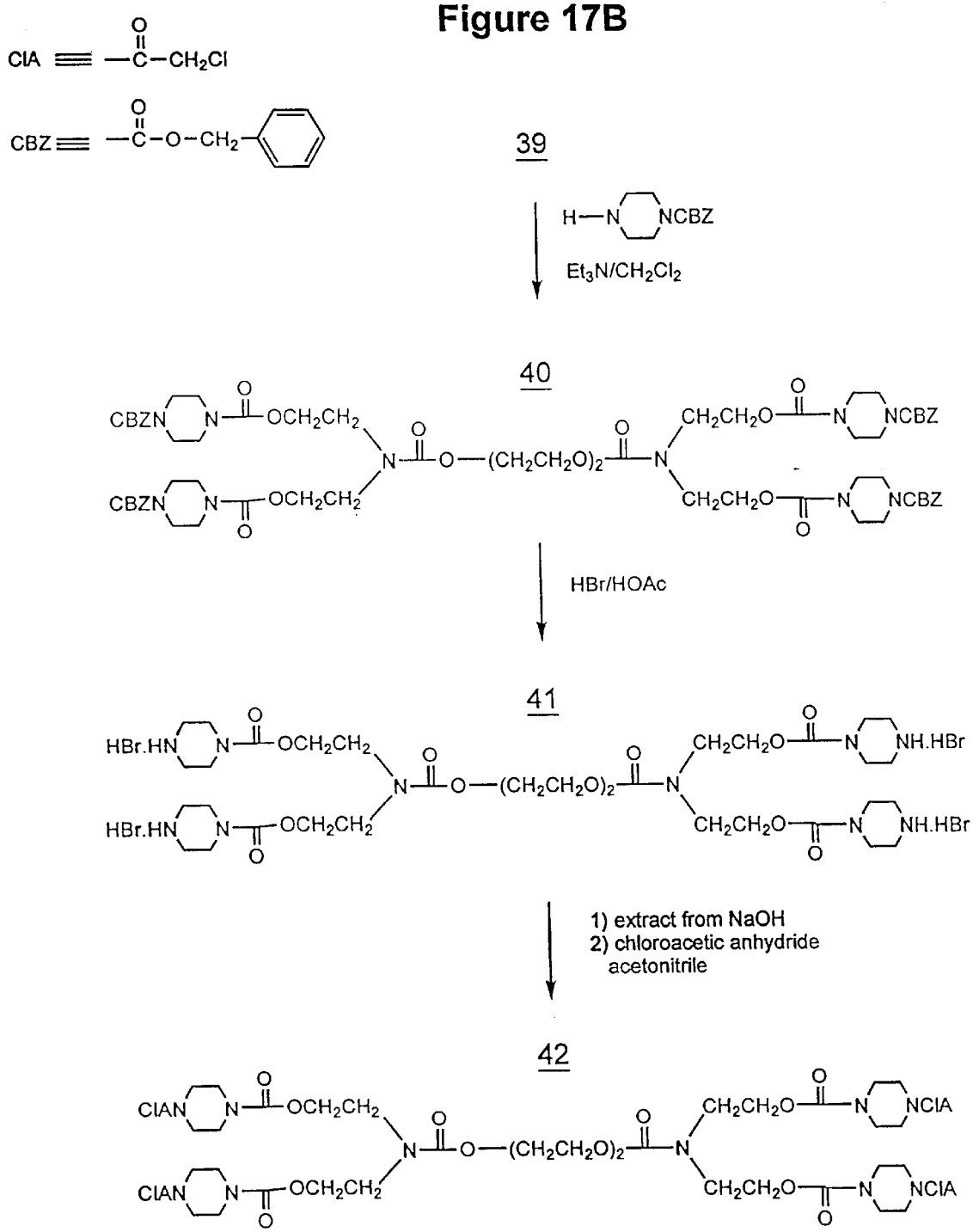

A chemical scheme for the preparation of an tetramer of DEA/DEG is shown in FIGS. 17A and 17B. Diethyleneglycol (from which the "core" is derived) was reacted with para-nitrophenylchloroformate to yield the di para-nitrophenylcarbonate compound (compound 37). Compound 37 was then reacted with diethanolamine to form the tetrahydroxy compound, compound 38. Compound 38 was then reacted with para-nitrophenylchloroformate to yield the tetrapara-nitrophenylcarbonate compound (compound 39). The para-nitrophenylcarbonate (PNP) group was then converted to a carbamate group by reaction with mono-CBZ-protected piperazine, yielding compound 40. The terminal CBZ-protected amino groups were then converted to the hydrobromide salt of amino group (compound 41), and further reacted with bromoacetic anhydride to yield reactive bromoacetyl groups at each of the termini in compound 42.

Compound 37

Diethyleneglycol bis-4-nitrophenylcarbonate

Pyridine (30.5 mL, 377 mmol) was slowly added to a 0° C. solution of 5.0 g (47.11 mmol) of diethylene glycol and 23.74 g (118 mmol) of 4-nitrophenylchloroformate in 500 mL of THF. The cooling bath was removed, and the mixture was stirred for 18 hours at room temperature. The mixture was cooled back to 0° C., acidified with 6 N HCl, and partitioned between 400 mL of 1 N HCl and 2×400 mL of $CH_2Cl_2$. The combined organic layers were dried ($MgSO_4$), filtered, and concentrated to give 24.3 g of a white solid. Crystallization from hexanes/EtOAc gave 16.0 g (78%) of compound 37 as a white powder: mp 110° C.; $^1$H NMR ($CDCl_3$) δ3.89 (t, 4H), 4.50 (t, 4H), 7.40 (d, 4H), 8.26 (d, 4H).

Compound 38

A solution of 2.5 g (5.73 mmol) of compound 37 in 17 mL of pyridine was added to a 0° C. solution of 1.8 g (17.2 mmol) of diethanolamine in 3 mL of pyridine. The cooling bath was removed, and the mixture was stirred for 5 hours at room temperature to yield compound 38, which was not isolated but was used as is in the next step.

Compound 39

The mixture from the previous step was cooled back to 0° C., 40 mL of $CH_2Cl_2$ was added followed by a solution of 11.55 g (57.3 mmol) of 4-nitrophenylchloroformate in 60 mL of $CH_2Cl_2$, and the mixture was stirred for 20 hours at room temperature. The mixture was cooled back to 0° C., acidified with 1 N HCl, and partitioned between 300 mL of 1 N HCl and 2×200 mL of $CH_2Cl_2$. The combined organic layers were dried ($MgSO_4$), filtered, and concentrated to give 13.6 g of yellow solid. Purification by silica gel chromatography ($CH_2Cl_2$/MeOH and EtOAc/hexanes) provided 4.91 g (83%) of compound 39 as a sticky amorphous solid: $^1$H NMR ($CDCl_3$) δ3.72 (m, 12H), 4.31 (t, 4H), 4.48 (m, 8H), 7.40 (m, 8H), 7.40 (m, 8H), 8.29 (m, 8H).

Compound 40

A solution of 128 mg (0.58 mmol) of mono-CBZ-piperazine in 1.0 mL of $CH_2Cl_2$ was added to a 0° C. solution of 100 mg (0.10 mmol) of compound 39 and 82 μL (0.58 mmol) of $Et_3N$ in 1.0 mL of $CH_2Cl_2$. The reaction mixture was stirred for 18 hours at room temperature, cooled to 0° C., and acidified with 1 N HCl. The mixture was partitioned between 10 mL of 1 N HCl and 3×10 mL of $CH_2Cl_2$. The combined organic layers were washed with saturated $NaHCO_3$ solution, dried ($MgSO_4$), filtered, and concentrated to give 162 mg of yellow oil. Purification by silica gel chromatography (EtOAc/hexanes followed by $CH_2Cl_2$/MeOH) provided 125 mg (95%) of compound 40 as a glassy amorphous solid: $^1$H NMR ($CDCl_3$) δ3.36–3.59 (m, 40H), 3.68 (t, 4H), 4.22 (m, 12H), 5.16, (s, 8H), 7.36 (brd s, 20H); MS (ESI) calculated for $C_{66}H_{24}NaN_{10})_{21}$ (M+Na): 1376. Found: 1376.

Compound 41

Compound 40 (150 mg, 0.11 mmol) was dissolved in 3 mL of 30% HBr/HOAc. The mixture was stirred for 30 minutes at room temperature, and the HBr salt was precipitated by addition of $Et_2O$. The precipitate, compound 41, was washed twice with $Et_2O$ and dried under vacuum.

Compound 42

The precipitate, compound 41, was dissolved in 20 mL of $H_2O$. The mixture was brought to pH 12 by addition of 10 N NaOH and extracted with six 20 mL portions of 4/1 $CH_2Cl_2$/MeOH. The combined organic layers were dried ($MgSO_4$), filtered, and concentrated to provide the free amine. The free amine was dissolved in 8 mL of $CH_3CN$, 1.5 mL of MeOH was added to improve solubility, and the solution was stirred at 0° C. while a solution of 114 mg (0.66 mmol) of chloroacetic anhydride in 2 mL of $CH_3CN$ was added. The mixture was stirred at room temperature for 2.5 hours and concentrated to give 107 mg of an oil. Purification by preparative HPLC (1" C18 column, gradient 25–45% B, A=0.1% TFA/$H_2O$ and B=0.1% TFA/$CH_3CN$) provided 44 mg of compound 42 as a viscous oil: $^1$H NMR ($CDCl_3$) δ3.41–3.80 (m, 44H), 4.12 (s, 8H), 4.24 (m, 12H); MS (ESI) calculated for $C_{42}H_{65}Cl_4N_{10}O_{17}$(M+H): 1121. Found: 1121.

Example 11

Synthesis of Octamer of DEA/DEG Using Core Propagation Approach

Figure 17C:
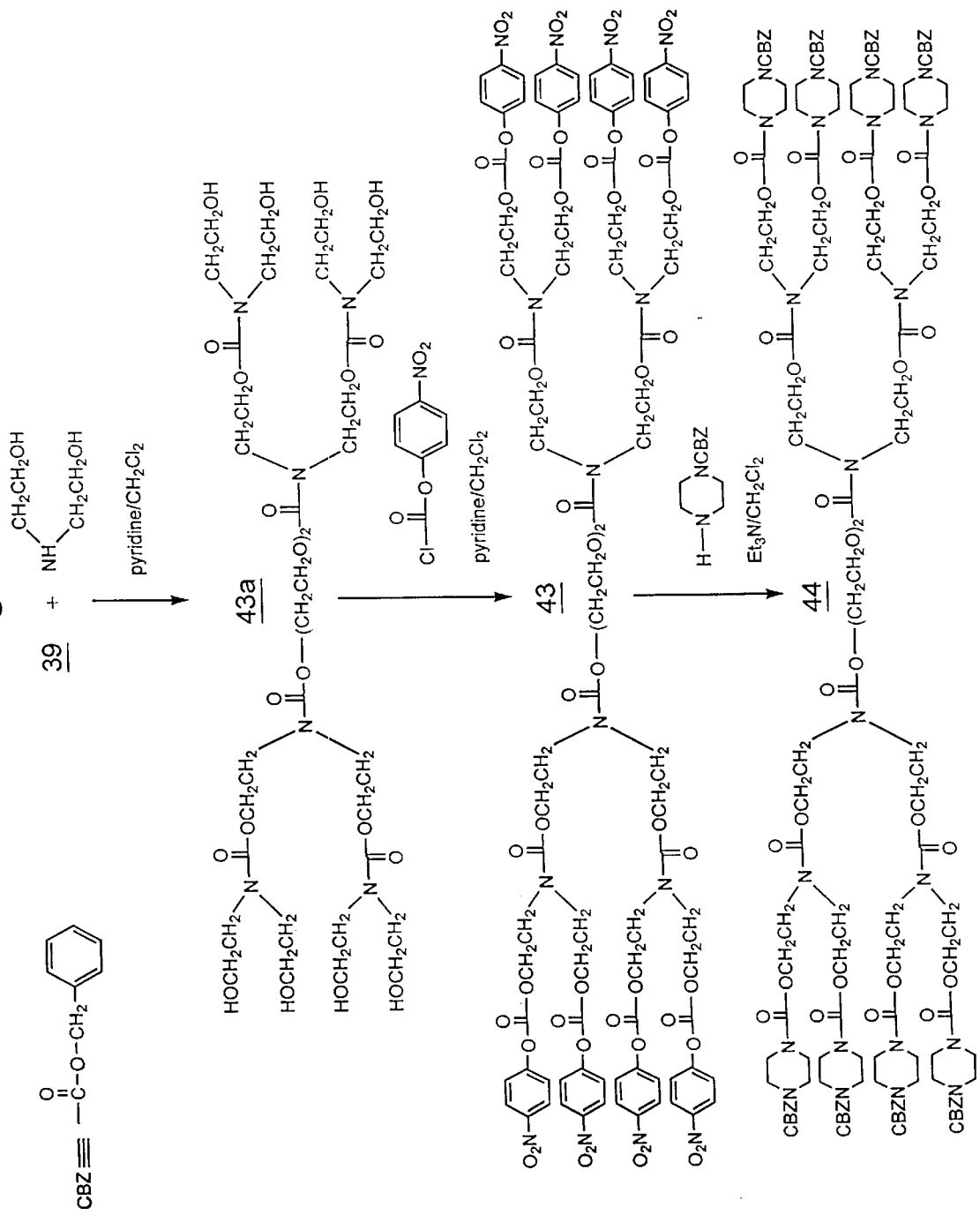
Figure 17D:
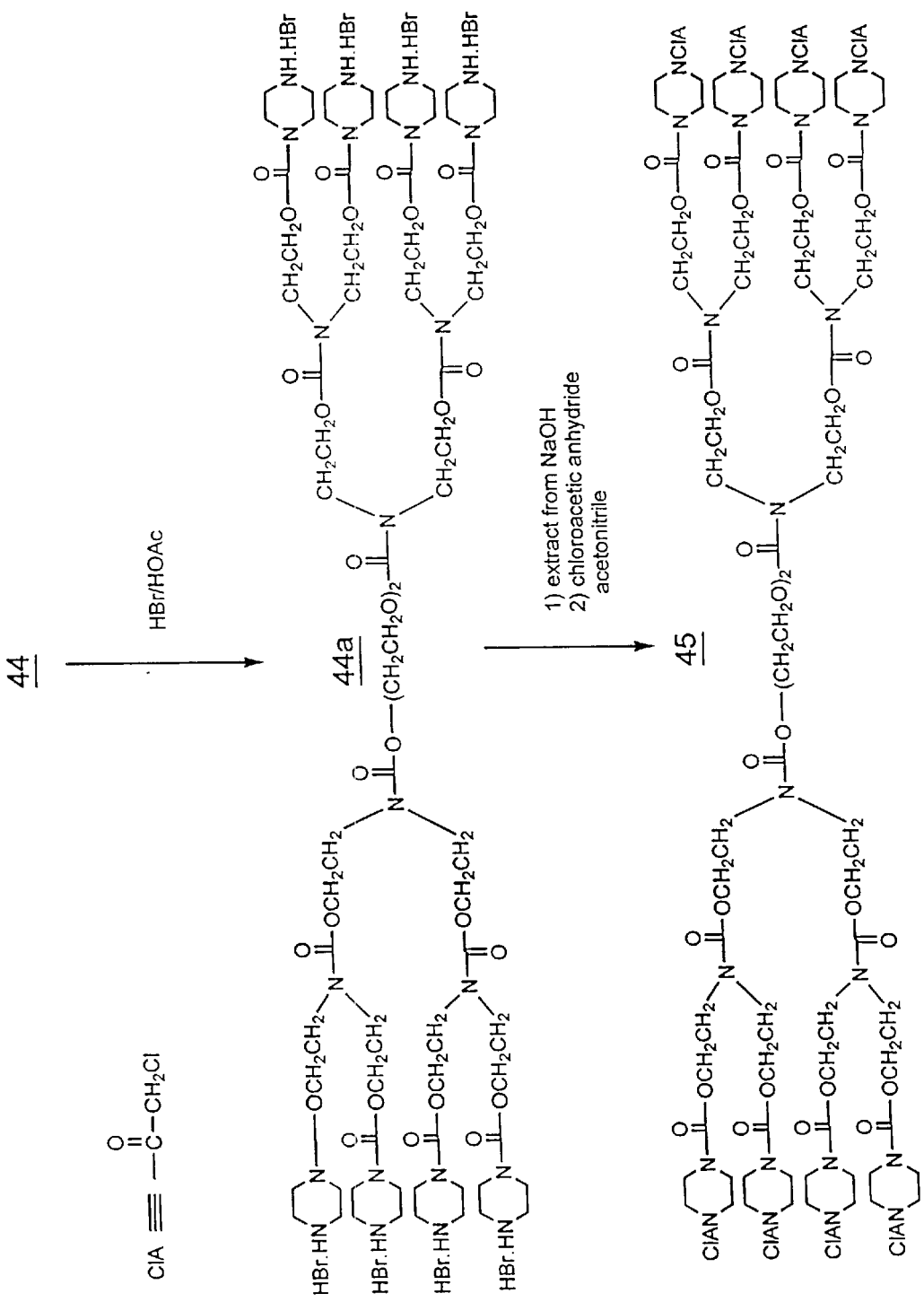

A chemical scheme for the preparation of an octamer of DEA/DEG is shown in FIGS. 17C and 17D. The tetraparanitrophenylcarbonate compound, compound 39, was reacted with diethanolamine to form the octahydroxy compound, compound 43a. Compound 43a was then reacted with para-nitrophenylchloroformate to yield the octa para-nitrophenylcarbonate compound (compound 43). The para-nitrophenylcarbonate (PNP) group was then converted to a carbamate group by reaction with mono-CBZ-protected piperazine, yielding compound 44. The terminal CBZ-protected amino groups were then converted to the hydrobromide salt of amino group (compound 44a), and further reacted with bromoacetic anhydride to yield reactive bromoacetyl groups at each of the termini in compound 45.

Compound 43a

A solution of 100 mg (0.097 mmol) of compound 39 in 450 μL of pyridine was added to a 0° C. solution of 61 mg (0.583 mmol) of diethanolamine in 150 μL of pyridine. The cooling bath was removed, and the mixture was stirred for 20 hours at room temperature, to yield the crude compound 43a, which was used as is in the next step.

Compound 43

The mixture from the previous step was cooled back to 0° C., and a solution of 431 mg (2.138 mmol) of 4-nitrophenylchloroformate in 4 mL of THF followed by 2 mL of $CH_2Cl_2$ to improve solubility. The mixture was stirred for 18 hours at room temperature, cooled back to 0° C., acidified with 1 N HCl, and partitioned between 20 mL of 1 N HCl and 2×20 mL of $CH_2Cl_2$. The combined organic layers were dried ($MgSO_4$), filtered, and concentrated to give 505 mg of yellow solid. Purification by silica gel chromatography (EtOAc/hexanes) provided 146 mg (68%) of compound 43 as a crystalline solid: mp 67–69° C.; $^1$H NMR ($CDCl_3$) δ3.50–3.80 (m, 28H), 4.22 (m, 12H), 4.43 (m, 16H), 7.40 (m, 16H), 8.30 (m, 16H).

Compound 44

A solution of 476 mg (2.16 mmol) of mono-CBZ-piperazine in 2.0 mL of $CH_2Cl_2$ was added to a 0° C. solution of 400 mg (0.18 mmol) of compound 43 and 300 μL (2.16 mmol) of $Et_3N$ in 2.0 mL of $CH_2Cl_2$. The reaction mixture was stirred for 18 hours at room temperature, cooled to 0° C., and acidified with 1 N HCl. The mixture was partitioned between 40 mL of 1 N HCl and 3×40 mL of $CH_2Cl_2$. The combined organic layers were washed with 3×40 mL of saturated $NaHCO_3$ solution, dried ($MgSO_4$), filtered, and concentrated to give 483 mg (97%) of compound 44 as a sticky white solid which was pure enough for use in the next step: $^1$H NMR (CDCl$_3$) δ3.36–3.60 (m, 88H), 3.66 (t, 4H), 4.21 (brd, 28H), 5.15, (s, 16), 7.36 (brd s, 40H).

Compound 44a

Compound 44 (150 mg, 0.054 mmol) was dissolved in 2 mL of 30% HBr/HOAc. The mixture was stirred for 30 minutes at room temperature, and the HBr salt was precipitated by addition of Et$_2$O. The precipitate was washed twice with Et$_2$O, and dried under vacuum.

Compound 45

The precipitate, compound 44a, was dissolved in 20 mL of H$_2$O. The mixture was brought to pH 12 by addition of 10 N NaOH and extracted with six 20 mL portions of 4/1 CH$_2$Cl$_2$/MeOH. The combined organic layers were dried (MgSO$_4$), filtered, and concentrated to provide the free amine. The free amine was dissolved in 4 mL of CH$_3$CN, 0.5 mL of MeOH was added to improve solubility, and the solution was stirred at 0° C. while a solution of 112 mg (0.65 mmol) of chloroacetic anhydride in 1 mL of CH$_3$CN was added. The mixture was stirred at room temperature for 2 hours and concentrated to give 111 mg of an oil. Purification by preparative HPLC (1" C18 column, gradient 35–55% B, A=0.1% TFA/H$_2$O and B=0.1% TFA/CH$_3$CN) provided 20 mg (15%) of compound 45 as a viscous oil: $^1$H NMR (CDCl$_3$) δ3.40–3.78 (m, 92H), 4.15 (S, 16H), 4.28, (m, 28H).

Example 12

Synthesis of Tetramer and Octamer of ADP/DEG Using Core Propagation Approach

Figure 18A:
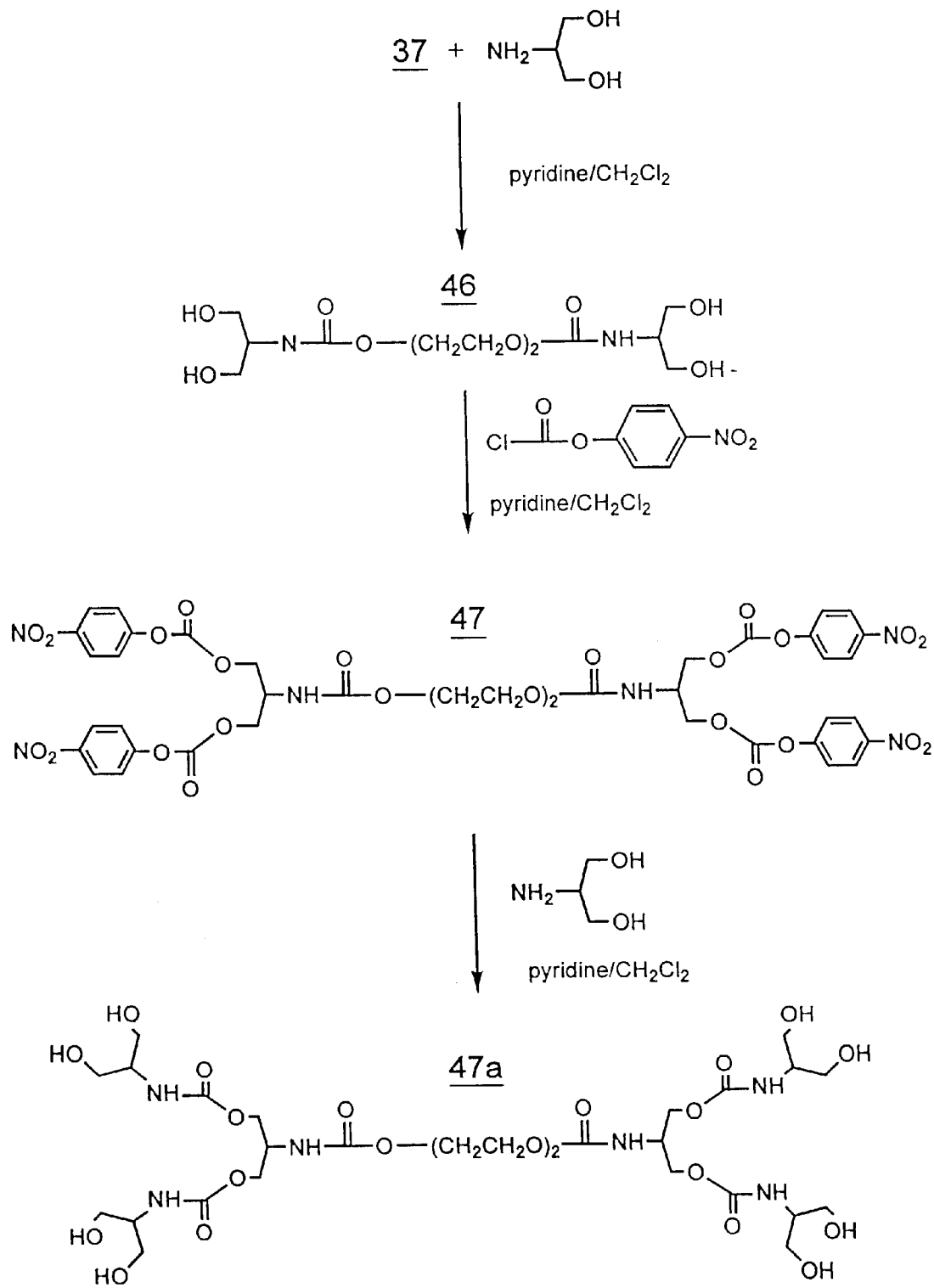
FIGS. 18A and 18B show synthetic schemes for the preparation of valency platform molecules of the present invention.
Figure 18B:
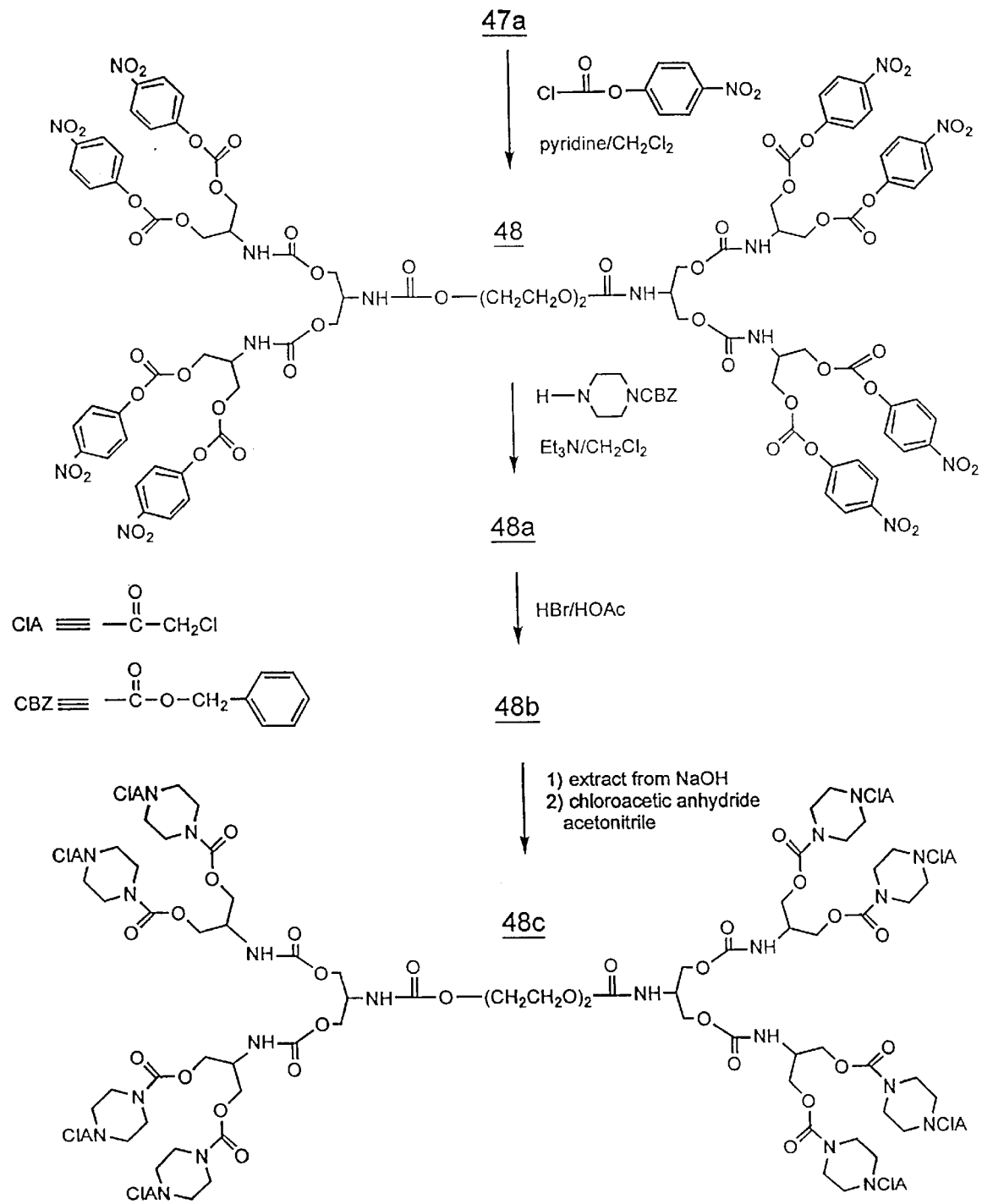

A chemical scheme for the preparation of an octamer of ADP/DEG is shown in FIGS. 18A and 18B. The di-para-nitrophenylcarbonate derivative of diethyleneglycol, compound 37 (from which the "core" is derived) was reacted with 2-amino-1,3-propanediol to yield the tetrahydroxy compound, compound 46. Compound 46 was reacted with para-nitrophenylchloroformate to yield the tetra para-nitrophenylcarbonate compound (compound 47). Compound 47 was then reacted with 2-amino-1,3-propanediol to yield the octahydroxy compound, compound 47a. Compound 47a was then reacted with para-nitrophenylchloroformate to yield the octa para-nitrophenylcarbonate compound (compound 48). The para-nitrophenylcarbonate (PNP) group was then converted to a carbamate group by reaction with mono-CBZ-protected piperazine, yielding compound 48a. The terminal CBZ-protected amino groups were then converted to the hydrobromide salt of amino group (compound 48b), and further reacted with chloroacetic anhydride to yield reactive chloroacetyl groups at each of the termini in compound 48c.

Compound 46

A solution of compound 37 in pyridine is added to a 0° C. solution of 3 eq. of 2-amino-1,3-propanediol in pyridine. The cooling bath is removed, and the mixture is stirred for 5 hours at room temperature. Compound 46 can be isolated if desired, however, it is generally more convenient to isolate after forming the 4-nitrophenylcarbonate ester.

Compound 47

The mixture above is cooled back to 0° C., a solution of 10 eq. of 4-nitrophenylchloroformate in 60 mL of CH$_2$Cl$_2$ is added, and the mixture is stirred for 20 hours at room temperature. The mixture is cooled back to 0° C., acidified with 1 N HCl, and is partitioned between 1 N HCl and CH$_2$Cl$_2$. The combined organic layers are dried (MgSO$_4$), filtered, and concentrated. Purification by silica gel chromatography provides compound 47.

Compound 47a

A solution of compound 47 in pyridine is added to a 0° C. solution of 6 eq. of 2-amino-1,3-propanediol in pyridine. The cooling bath is removed, and the mixture is stirred for 20 hours at room temperature to yield compound 47a, which is used in the next step.

Compound 48

The mixture above is cooled back to 0° C., and a solution of 4-nitrophenylchloroformate is added. The mixture is stirred for 18 hours at room temperature, cooled back to 0° C., acidified with 1 N HCl, and partitioned between 1 N HCl and CH$_2$Cl$_2$. The combined organic layers are dried (MgSO$_4$), filtered, and concentrated. Purification by silica gel chromatography provides compound 48.

Compound 48a

In a manner similar to that for compound 44 above, a solution of mono-CBZ-piperazine in CH$_2$Cl$_2$ is added to a 0° C. solution of compound 43 and Et$_3$N in CH$_2$Cl$_2$. The reaction mixture was stirred for 18 hours at room temperature, cooled to 0° C., and acidified with 1 N HCl. The mixture was partitioned between 1 N HCl and CH$_2$Cl$_2$. The combined organic layers are washed with saturated NaHCO$_3$ solution, dried (MgSO$_4$), filtered, and concentrated to give compound 48a, for use in the next step.

Compound 48b

In a manner similar to that for compound 44a above, compound 48a is dissolved in 30% HBr/HOAc. The mixture is stirred for 30 minutes at room temperature, and the HBr salt precipitated by addition of Et$_2$O. The precipitate is washed with Et$_2$O, and dried under vacuum.

Compound 48c

In a manner similar to that for compound 45 above, the precipitate, compound 48b, is dissolved in H$_2$O. The mixture is brought to pH 12 by addition of 10 N NaOH and extracted with 4/1 CH$_2$Cl$_2$/MeOH. The combined organic layers are dried (MgSO$_4$), filtered, and concentrated to provide the free amine. The free amine is dissolved in CH$_3$CN, MeOH is added to improve solubility, and the solution is stirred at 0° C. while a solution of chloroacetic anhydride in CH$_3$CN is added. The mixture was stirred at room temperature for 2 hours and concentrated to give crude compound 48c, which is purified by preparative HPLC.

Example 13

Synthesis of Octamer of DEA/PE Using Core Propagation Approach

Figure 19:
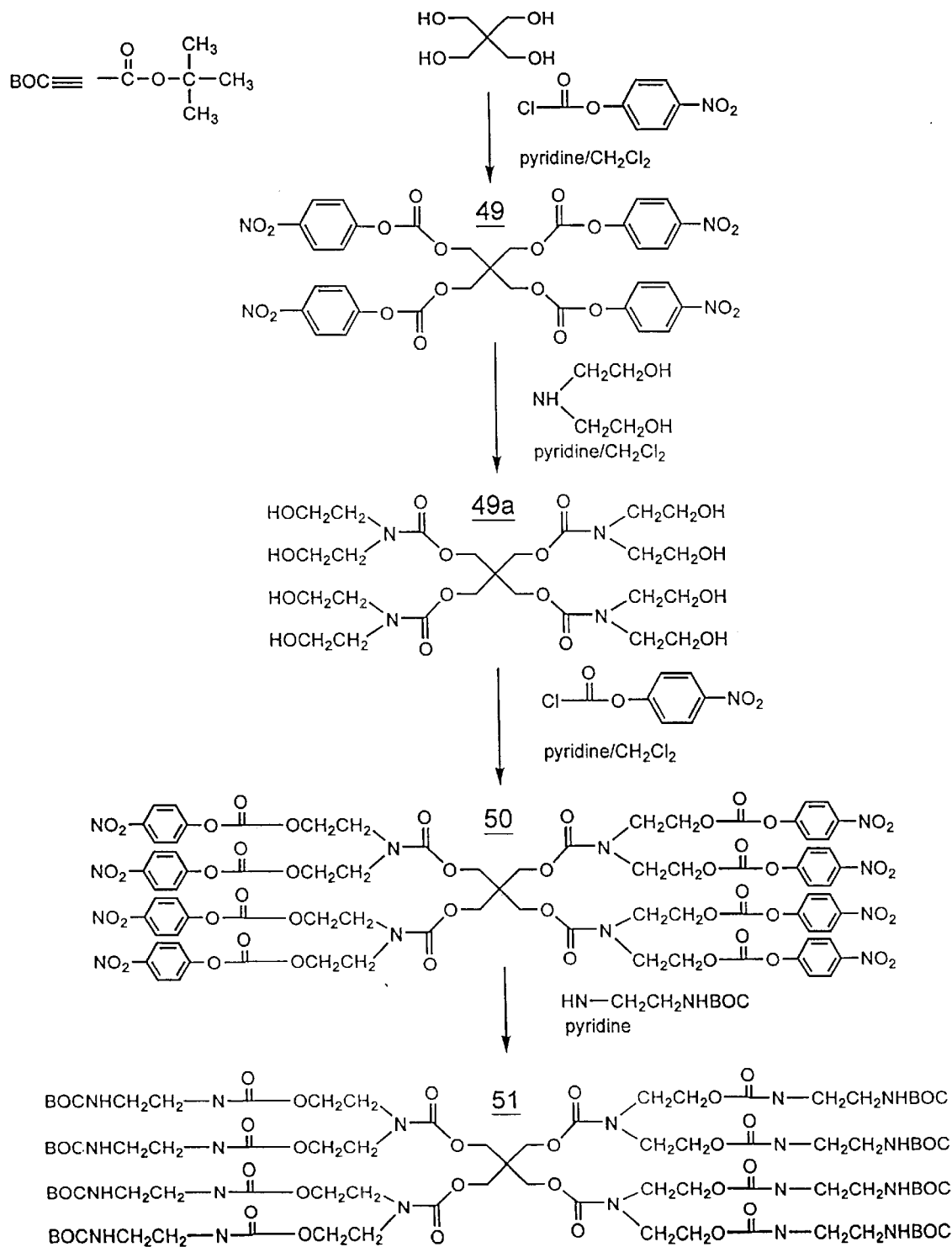
FIG. 19 shows a synthetic schemes for the preparation of valency platform molecules of the present invention.

A chemical scheme for the preparation of an octamer of DEA/PE is shown in FIG. 19. Pentaerythritol (from which the "core" is derived) was reacted with para-nitrophenylchloroformate to yield the tetrapara-nitrophenylcarbonate compound (compound 49). Compound 49 was then reacted with diethanolamine to form the octahydroxy compound, compound 49a. Compound 49a was then reacted with para-nitrophenylchloroformate to yield the octa para-nitrophenylcarbonate compound (compound 50). The para-nitrophenylcarbonate (PNP) group was then converted to a carbamate group by reaction with mono-N-BOC-ethylenediamine, yielding compound 51.

Compound 49

Pentaerythritol tetrakis-4-nitrophenylcarbonate

Pyridine (950 µL, 11.74 mmol) was slowly added to a 0° C. solution of 100 mg (0.734 mmol) of pentaerythritol and 1.18 g (5.88 mmol) of 4-nitrophenylchloroformate in 10 mL of $CH_2Cl_2$. The cooling bath was removed, and the mixture was stirred for 24 hours at room temperature. The mixture was cooled back to 0° C., acidified with 1 N HCl, and partitioned between 50 mL of 1 N HCl and 2×50 mL of $CH_2Cl_2$. The combined organic layers were dried ($MgSO_4$), filtered, and concentrated to give 1.123 g of a white solid. Purification by silica gel chromatography (EtOAc/hexanes followed by $CH_2Cl_2$/MeOH) provided 128 mg (22%) of compound 49 as a white crystalline solid: mp 175° C.;: $^1H$ NMR ($CDCl_3$) δ4.61 (s, 8H), 7.40, (m, 8H), 8.30 (m, 8H).

Compound 49a

To solution of 120 mg (0.150 mmol) of compound 49 in 1.6 mL of pyridine at 0° C. was added 87 µL (95 mg, 0.90 mmol) of diethanolamine. The cooling bath was removed, and the mixture was stirred for 7 hours at room temperature, and cooled back to 0° C., to yield compound 49a, which was used as is in the next step.

Compound 50

A solution of 756 mg (3.75 mmol) of 4-nitrophenylchloroformate in 3 mL of $CH_2Cl_2$ was added the mixture above. The mixture was stirred for 18 hours at room temperature, cooled back to 0° C., acidified with 1 N HCl, and partitioned between 20 mL of 1 N HCl and 2×20 mL of $CH_2Cl_2$. The combined organic layers were dried ($MgSO_4$), filtered, and concentrated to give 819 mg of sticky yellow solid. Purification by silica gel chromatography (EtOAc/hexanes and $CH_2Cl_2$/MeOH) provided 134 mg (47%) of compound 50 as a sticky viscous oil with some impurities: $^1H$ NMR ($CDCl_3$) δ3.69 (m, 16H), 4.31 (s, 8H), 4.41 (m, 16H), 7.39 (m, 16H), 8.25 (m, 16H).

Compound 51

A solution of compound 50 is treated with 10 eq. of mono-N-BOC-ethylenediamine in pyridine and $CH_2Cl_2$. The mixture is stirred at room temperature until complete as evidenced by TLC, and partitioned between 1 N HCl and $CH_2Cl_2$. The combined organic layers is dried ($MgSO_4$), filtered, and concentrated to give crude product. Purification by silica gel chromatography (EtOAc/hexanes and $CH_2Cl_2$/MeOH) provides compound 51.

Example 14

Solid Phase Synthesis of Tetramer of DEA/DEG Using Segmental Approach

Figure 20A:
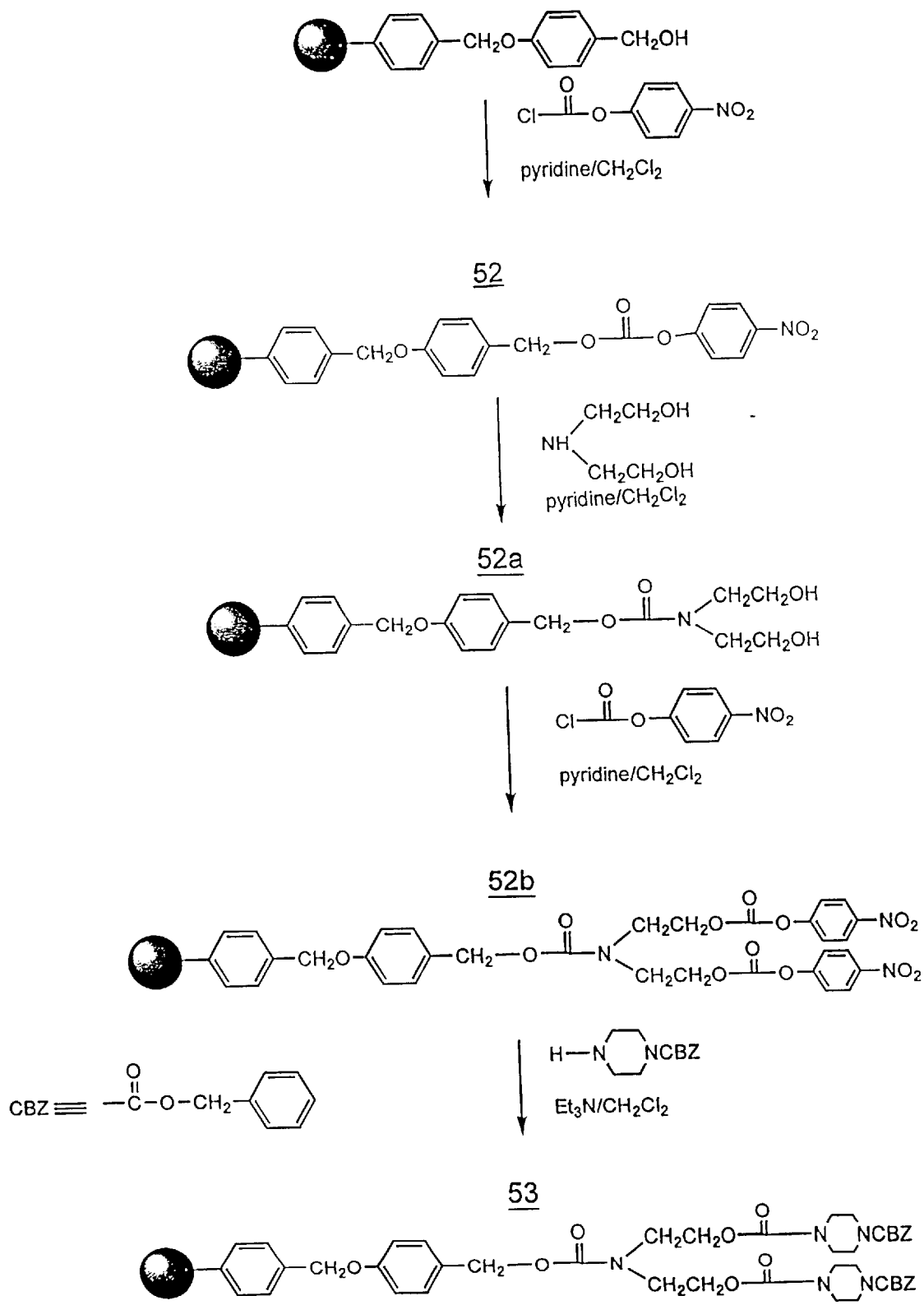
FIGS. 20A and 20B show synthetic schemes for the preparation of valency platform molecules of the present invention.
Figure 20B:
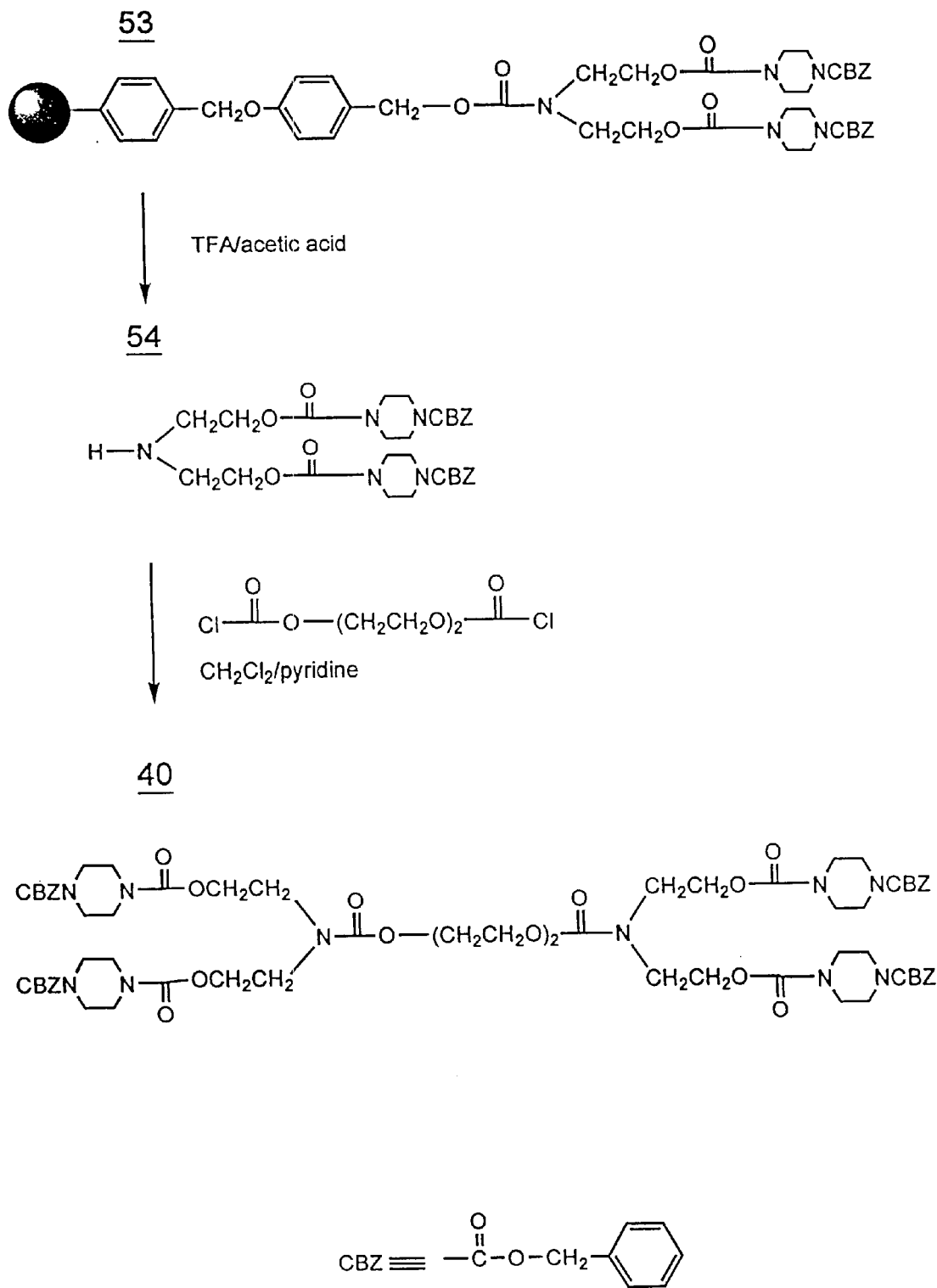

A chemical scheme for the solid phase synthesis of a tetramer of octamer of DEA/DEG is shown in FIGS. 20A and 20B. Wang resin, having terminal hydroxy groups, was reacted with para-nitrophenylchloroformate to yield the para-nitrophenylcarbonate compound (compound 52). Compound 52 was then reacted with diethanolamine to form the dihydroxy compound, compound 52a. Compound 52a was then reacted with para-nitrophenylchloroformate to yield the di para-nitrophenylcarbonate compound (compound 52b). The para-nitrophenylcarbonate (PNP) group was then converted to a carbamate group by reaction with mono-CBZ-protected piperazine, yielding compound 53. The CBZ-protected compound was then cleaved from the resin, and reacted with diethyleneglycol bis chloroformate (from which the "core" is derived), to yield the tetra-CBZ-protected amino compound, compound 40. The terminal CBZ-protected amino groups may be converted to the hydrobromide salt of amino group, and further reacted with chloroacetic anhydride to yield reactive chloroacetyl groups at each of the termini.

Compound 52

Wang resin (25 mg, subst. 0.58 mmol/g, 0.0145 mmol) was washed with $CH_2Cl_2$. The resin was suspended in 580 µL of $CH_2Cl_2$, and 15 mg (0.145 mmol) of 4-nitrophenylchloroformate was added followed by 97 µL of pyridine. After gentle agitation of the mixture for 4 hours, the resin was washed with $CH_2Cl_2$ and dried, to yield compound 52.

Compound 52a

The resin was then suspended in 410 µL of $CH_2Cl_2$, and 71 mg (0.673 mmol) of diethanolamine (410 µL of a solution of 82.5 mg of diethanolamine dissolved in 493 µL of pyridine). After gentle agitation of the mixture for 16 hours, the resin was washed with $CH_2Cl_2$ and dried, to yield compound 52a.

Compound 52b

To the resin was added 580 µL of $CH_2Cl_2$, and to the mixture was added 15.2 mg (0.145 mmol) of 4-nitrophenylchloroformate followed by 97 µL of pyridine. After gentle agitation of the mixture for 4 hours, the resin was washed with $CH_2Cl_2$ and dried, to yield compound 52b.

Compound 53

To the resin was added 410 µL of $CH_2Cl_2$, and to the mixture was added 130 µL of mono-CBZ-piperazine followed by 410 µL of pyridine. After gentle agitation of the mixture for 18 hours, the resin was washed with $CH_2Cl_2$ and dried, to yield compound 53.

Compound 54

To the resin was added 1 mL of 10% TFA in $CH_2Cl_2$, the mixture was agitated for 10 min, and the mixture was filtered. The TFA treatment was repeated twice, and the combined filtrates were combined and concentrated to give 3 mg (35%) of compound 54; $^1H$ NMR ($CDCl_3$) δ3.13 (m, 4H), 3.48 (m, 8H), 3.80 (m, 4H), 4.50 (m, 1H), 5.18 (s, 4H), 7.37 (brd s, 10H); MS (ESI) calculated for $C_{30}H_{40}N_5O_8$ (M+H): 598. Found: 598.

Compound 40

To a solution of 2.1 eq. of compound 54 and 2.1 eq. of $Et_3N$ in $CH_2Cl_2$ at 0° C. is added a solution of 1 eq. of diethyleneglycol bis-chloroformate in $CH_2Cl_2$. The mixture is stirred for at room temperature and concentrated to give crude compound 40 which can be purified by silica gel chromatography.

Example 15

Compound 39b

To a solution of 3.17 g (3.08 mmol) of compound 39 in 35 mL of $CH_2Cl_2$ at 0° C. was added 2.6 mL of $Et_3N$ followed by a solution of 3.26 g (18.49 mmol) of mono—N—Boc-ethylenediamine (also referred to as tert-butyl N-(2-aminoethyl)carbamate, Aldrich Chemical Co.) in 30 mL of $CH_2Cl_2$. The mixture was stirred at room temperature for 18 hours, cooled to 0°, and acidified with 1 N HCl The mixture was then partitioned between 150 mL of 1 N HCl and three 100 mL portions of $CH_2Cl_2$. The organic layers were combined and washed with three portions of saturated sodium bicarbonate solution, dried ($MgSO_4$), filtered and concentrated to provide 3.17 g of yellow solid. Purification by silica gel chromatography (step gradient 98/2 to 95/5 to 90/10 $CH_2Cl_2$/MeOH) provided 2.76 g (80%) of compound 39b as a white solid. $^1H$ NMR ($CDCl_3$) δ1.45 (s, 36H), 3.23 (s, 16H), 3.50 (m, 8H), 3.72 (t, 4H), 4.19 (m, 8H), 4.26 (t, 4H), 5.38 (brd s, 4H), 5.80 (brd s, 2H), 6.00 (brd s, 2H); mass spectrum (ES) m/z calculated for $C_{46}H_{84}N_{10}O_{21}$ (M+Na): 1135. Found: 1135.

Compound 39c

A solution of 1 g (9.42 mmol) of diethylene glycol in 20 mL of EtOAc was added to a solution of 3.82 g (23.5 mmol) of carbonyldiimidazole in 80 mL EtOAc and the resulting mixture was stirred for 2 hours at room temperature. The mixture was concentrated to an oily solid, and the product was purified by silica gel chromatography (97/2 $CH_2Cl_2$/MeOH) to give 2.04 g (73%) of the bis-imidazolide of diethylene glycol as a white solid: $^1H$ NMR ($CDCl_3$) δ3.87 (t, 4H), 4.58 (t, 4H), 7.08 (s, 2H), 7.41 (s, 2H), 8.16 (s, 2H). A solution of 50 mg (0.17 mmol) of the bis-imidazolide of diethylene glycol in 1 mL of $CH_2Cl_2$ was added to a solution of 54 mg (0.51) mmol) of diethanolamine and 82 μL (80.6 mg, 1.02 mmol) of pyridine in 0.5 mL of $CH_2Cl_2$. The mixture was stirred at room temperature for four hours, and to the mixture was added a solution of 248 mg (1.53 mmol) of carbonyldiimidazole in 5 mL of $CH_2Cl_2$. The mixture was stirred at room temperature for 1.5 hours and concentrated to an oily solid. Purification by silica gel chromatography (98/2 $CH_2Cl_2$/MeOH) provided 103 mg (82%) of the multivalent activated carbonate derivative compound 39c, including minor impurities. The resulting oil crystallized when placed in the freezer: $^1H$ NMR ($CDCl_3$) δ3.71 (m, 12H), 4.32 (m, 4H), 4.59 (t, 8H), 7.10 (s, 4H), 7.43 (s, 4H), 8.18 (s, 4H); mass spectrum (ES) m/z (relative intensity) 380 (100), 443 (18), 512 (26), no parent ion observed.

What is claimed is:

1. A compound having the structure of one of the following formulae:

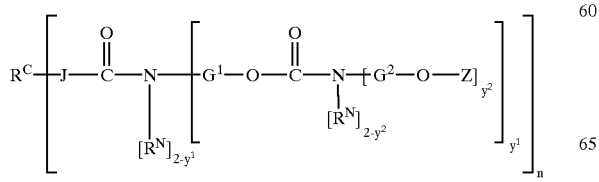

Formula II

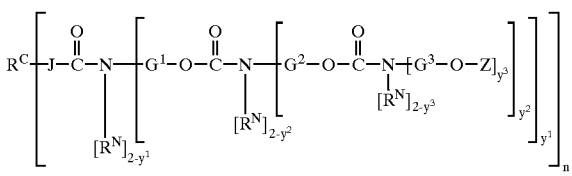

Formula III wherein:
n is a positive integer from 1 to 10;
$y^1$, $y^2$, and $y^3$ are independently 1 or 2;
J independently denotes either an oxygen atom or a covalent bond;
$R^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
  organic groups consisting only of carbon, oxygen, sulfur, and hydrogen atoms, and having from 1 to 20 carbon atoms;
each $G^1$, $G^2$, and $G^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms;
each $R^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms;
  heteroaromatic groups having from 3 to 20 carbon atoms;
each Z is independently selected from the group consisting of:
  —H
  —C(=O)O$R^{CARB}$
  —C(=O)$R^{ESTER}$
  —C(=O)N$R^AR^B$
wherein:
  each $R^{CARB}$ is organic groups comprising from 1 to about 20 carbon atoms;
  each $R^{ESTER}$ is organic groups comprising from 1 to about 20 carbon atoms;
  each group —N$R^AR^B$ is independently selected from the group consisting of:
    —$NH_2$
    —NH$R^A$
    —N$R^AR^B$
    —N$R^{AB}$
  wherein each monovalent $R^A$ and $R^B$ and each divalent $R^{AB}$ is independently an organic group comprising from 1 to 20 carbon atoms, and further comprising a reactive conjugating functional group;

wherein the compound has at least three carbamate linkages and at least two branches.

2. A compound according to claim 1, wherein said compound has the structure of Formula II.

3. A compound according to claim 1, wherein said compound has the structure of Formula III.

4. A compound according to claim 1, wherein n is a positive integer from 2 to 4.

5. A compound according to claim 1, wherein $y^1$, $y^2$, and $y^3$ are each 2.

6. A compound according to claim 1, wherein J is an oxygen atom.

7. A compound according to claim 1, wherein J is a covalent bond.

8. A compound according to claim 1, wherein $R^C$ is selected from the group consisting of hydrocarbyl groups having from 1 to 20 carbon atoms.

9. A compound according to claim 1, wherein $R^C$ is selected from the group consisting of:

—CH$_2$— ; —CH$_2$CH$_2$— ;

—CH$_2$CH$_2$CH$_2$— ; —CH$_2$—C(CH$_2$)(CH$_2$)—CH$_2$— ; and

[para-phenylene].

10. A compound according to claim 1, wherein $R^C$ is selected from the group consisting of organic groups consisting only of carbon, oxygen, and hydrogen atoms, and having from 1 to 20 carbon atoms.

11. A compound according to claim 1, wherein $R^C$ is:

$$-(CH_2-CH_2-O)_{p-1}-CH_2-CH_2-$$

wherein p is a positive integer from 2 to 20.

12. A compound according to claim 1, wherein each $G^1$, $G^2$, and $G^3$ is independently selected from the group consisting of hydrocarbyl groups having from 1 to 20 carbon atoms.

13. A compound according to claim 1, wherein each $G^1$, $G^2$, and $G^3$ is —(CH$_2$)$_q$— wherein q is a positive integer from 1 to 20.

14. A compound according to any one of claims 1, wherein each $G^1$, $G^2$, and $G^3$ is independently selected from the group consisting of organic groups consisting only of carbon, oxygen, and hydrogen atoms, and having from 1 to 20 carbon atoms.

15. A compound according to claim 1, wherein each $G^1$, $G^2$, and $G^3$ is:

$$-(CH_2-CH_2-O)_{p-1}-CH_2-CH_2-$$

wherein p is a positive integer from 2 to 20.

16. A compound according to claim 1, wherein each $R^N$ is independently selected from the group consisting of —H, —CH$_3$, and —CH$_2$CH$_3$.

17. A compound according to claim 1, wherein each Z is —NR$^A$R$^B$ and is independently selected from the group consisting of:

—N(piperazine)N—H

—N(piperazine)N—C(=O)—O—CH$_2$—[phenyl]

—N(piperazine)NH.HBr

—N(piperazine)N—C(=O)—CH$_2$—X

—NH—(CH$_2$)$_n$—NH$_2$

—NH—CH$_2$CH$_2$—NH—C(=O)—O—C(CH$_3$)$_3$ and

—NH—(CH$_2$CH$_2$O)$_n$—CH$_2$CH$_2$—NH$_2$.

18. A compound having the structure of one of the following formulae:

Formula V $$R^C\left[J-\overset{O}{\underset{}{C}}-\underset{R^N}{N}-G^1-\left[O-\overset{O}{\underset{}{C}}-\underset{R^N}{N}-G^2-[O-Z]_{y^2}\right]_{y^1}\right]_n$$

Formula VI $$R^C\left[J-\overset{O}{\underset{}{C}}-\underset{R^N}{N}-G^1-\left[O-\overset{O}{\underset{}{C}}-\underset{R^N}{N}-G^2-\left[O-\overset{O}{\underset{}{C}}-\underset{R^N}{N}-G^3-[O-Z]_{y^3}\right]_{y^2}\right]_{y^1}\right]_n$$

wherein:
  n is a positive integer from 1 to 10;
  $y^1$, $y^2$, and $y^3$ are independently a positive integer from 1 to 10;
  J independently denotes either an oxygen atom or a covalent bond;
  $R^C$ is selected from the group consisting of:
    hydrocarbyl groups having from 1 to 20 carbon atoms;
    organic groups consisting only of carbon, oxygen, and hydrogen atoms, and having from 1 to 20 carbon atoms;
    organic groups consisting only of carbon, oxygen, nitrogen, and hydrogen atoms, and having from 1 to 20 carbon atoms;
    organic groups consisting only of carbon, oxygen, sulfur, and hydrogen atoms, and having from 1 to 20 carbon atoms;
  each $G^1$, $G^2$, and $G^3$ is independently selected from the group consisting of:
    hydrocarbyl groups having from 1 to 20 carbon atoms;
    organic groups consisting only of carbon, oxygen, and hydrogen atoms, and having from 1 to 20 carbon atoms;
    organic groups consisting only of carbon, oxygen, nitrogen, and hydrogen atoms, and having from 1 to 20 carbon atoms;
  each $R^N$ is independently selected from the group consisting of:
    hydrogen;
    linear or branched alkyl groups having from 1 to 15 carbon atoms;
    alkyl groups comprising an alicyclic structure and having from 1 to 15 carbon atoms;
    aromatic groups having from 6 to 20 carbon atoms;
    heteroaromatic groups having from 3 to 20 carbon atoms;
  each Z is independently selected from the group consisting of:
    —H
    —C(=O)OR$^{CARB}$
    —C(=O)R$^{ESTER}$
    —C(=O)NR$^A$R$^B$
  wherein:
    each R$^{CARB}$ is organic groups comprising from 1 to about 20 carbon atoms;
    each R$^{ESTER}$ is organic groups comprising from 1 to about 20 carbon atoms;
    each group —NR$^A$R$^B$ is independently selected from the group consisting of:
      —NH$_2$
      —NHR$^A$
      —NR$^A$R$^B$
      13 NR$^{AB}$
    wherein each monovalent R$^A$ and R$^B$ and each divalent R$^{AB}$ is independently an organic group comprising from 1 to 20 carbon atoms, and further comprising a reactive conjugating functional group;
  wherein the compound has at least three carbamate linkages and at least two branches.

19. A compound according to claim 18, wherein said compound has the structure of Formula V.

20. A compound according to claim 18, wherein said compound has the structure of Formula VI.

21. A compound according to claim 18, wherein n is a positive integer from 2 to 4.

22. A compound according to claim 18, wherein $y^1$, $y^2$, and $y^3$ are each 2.

23. A compound according to claim 18, wherein J is an oxygen atom.

24. A compound according to claim 18, wherein J is a covalent bond.

25. A compound according to claim 18, wherein $R^C$ is selected from the group consisting of hydrocarbyl groups having from 1 to 20 carbon atoms.

26. A compound according to claim 18, wherein $R^C$ is selected from the group consisting of:

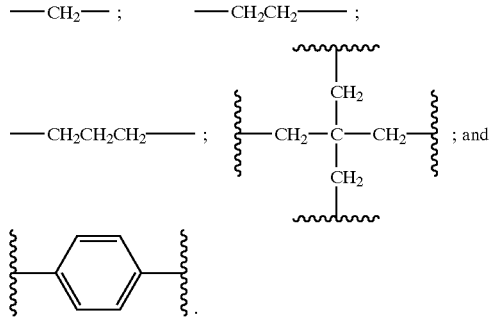

27. A compound according to claim 18, wherein $R^C$ is selected from the group consisting of organic groups consisting only of carbon, oxygen, and hydrogen atoms, and having from 1 to 20 carbon atoms.

28. A compound according to claim 18, wherein $R^C$ is:

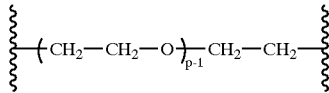

wherein p is a positive integer from 2 to 20.

29. A compound according to claim 18, wherein each $G^1$, $G^2$, and $G^3$ is independently selected from the group consisting of hydrocarbyl groups having from 1 to 20 carbon atoms.

30. A compound according to claim 18, wherein each $G^1$, $G^2$, and $G^3$ is selected from the group consisting of:

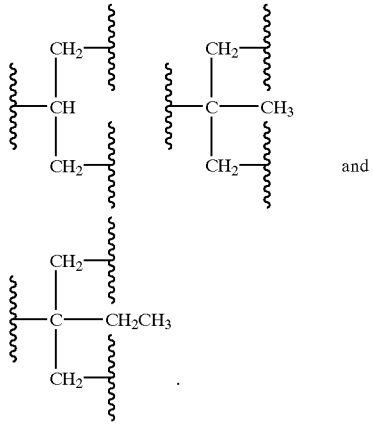

31. A compound according to claim 18, wherein each $G^1$, $G^2$, and $G^3$ is independently selected from the group consisting of organic groups consisting only of carbon, oxygen, and hydrogen atoms, and having from 1 to 20 carbon atoms.

32. A compound according to claim 18, wherein each $R^N$ is independently selected from the group consisting of —H, —CH$_3$, and —CH$_2$CH$_3$.

33. A compound according to claim 19, wherein each Z is —NR$^A$R$^B$ and is independently selected from the group consisting of:

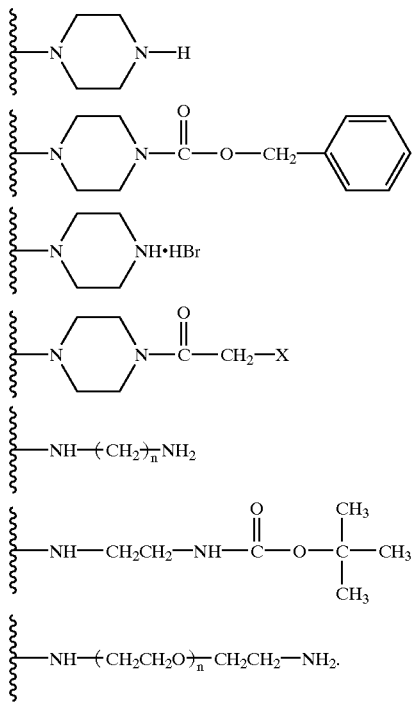

34. A compound having the structure of the following formula:

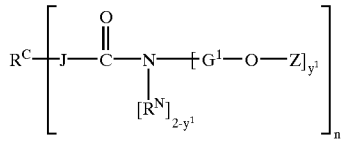

Formula I wherein:
n is a positive integer from 1 to 10;
y$^1$, y$^2$, and y$^3$ are independently 1 or 2;
J is an oxygen atom;
R$^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms; and
  organic groups consisting only of carbon, oxygen, sulfur, and hydrogen atoms, and having from 1 to 20 carbon atoms;
each G$^1$, G$^2$, and G$^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms; and
  organic groups consisting only of carbon, oxygen, nitrogen, and hydrogen atoms, and having from 1 to 20 carbon atoms;

each R$^N$ is independently selected from the group consisting of:
  hydrogen;
  linear or branched alkyl groups having from 1 to 15 carbon atoms;
  alkyl groups comprising an alicyclic structure and having from 1 to 15 carbon atoms;
  aromatic groups having from 6 to 20 carbon atoms; and
  heteroaromatic groups having from 3 to 20 carbon atoms;
each Z is independently selected from the group consisting of:
  —H
  —C(=O)OR$^{CARB}$
  —C(=O)R$^{ESTER}$
  —C(=O)NR$^A$R$^B$;
wherein:
  each R$^{CARB}$ is organic groups comprising from 1 to about 20 carbon atoms;
  each R$^{ESTER}$ is organic groups comprising from 1 to about 20 carbon atoms;
  each group —NR$^A$R$^B$ is independently selected from the group consisting of:
    —NH$_2$;
    —NHR$^A$;
    —NR$^A$R$^B$; and
    —NR$^{AB}$;
  wherein each monovalent R$^A$ and R$^B$ and each divalent R$^{AB}$ is independently an organic group comprising from 1 to 20 carbon atoms, and further comprising a reactive conjugating functional group;
wherein the compound has at least three carbamate linkages and at least two branches.

35. A compound having the structure of the following formula:

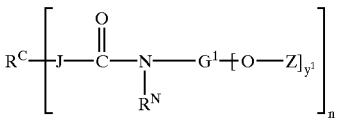

Formula IV wherein:
n is a positive integer from 1 to 10;
y$^1$, y$^2$, and y$^3$ are independently a positive integer from 1 to 10;
J is an oxygen atom;
R$^C$ is selected from the group consisting of:
  hydrocarbyl groups having from 1 to 20 carbon atoms;
  organic groups consisting only of carbon, oxygen, and hydrogen atoms, and having from 1 to 20 carbon atoms;
  organic groups consisting only of carbon, oxygen, nitrogen, and hydrogen atoms, and having from 1 to 20 carbon atoms; and
  organic groups consisting only of carbon, oxygen, sulfur, and hydrogen atoms, and having from 1 to 20 carbon atoms;
each G$^1$, G$^2$, and G$^3$ is independently selected from the group consisting of:
  hydrocarbyl groups having from 1 to 20 carbon atoms;
  organic groups consisting only of carbon, oxygen, and hydrogen atoms, and having from 1 to 20 carbon atoms; and
  organic groups consisting only of carbon, oxygen, nitrogen, and hydrogen atoms, and having from 1 to 20 carbon atoms;

each $R^N$ is independently selected from the group consisting of:
hydrogen;
linear or branched alkyl groups having from 1 to 15 carbon atoms;
alkyl groups comprising an alicyclic structure and having from 1 to 15 carbon atoms;
aromatic groups having from 6 to 20 carbon atoms; and
heteroaromatic groups having from 3 to 20 carbon atoms;
each Z is independently selected from the group consisting of:
—H
—C(=O)OR$^{CARB}$
—C(=O)R$^{ESTER}$
—C(=O)NR$^A$R$^B$;
wherein:
each R$^{CARB}$ is organic groups comprising from 1 to about 20 carbon atoms;
each R$^{ESTER}$ is organic groups comprising from 1 to about 20 carbon atoms;
each group —NR$^A$R$^B$ is independently selected from the group consisting of:
—NH$_2$;
—NHR$^A$;
—NR$^A$R$^B$; and
—NR$^{AB}$;
wherein each monovalent R$^A$ and R$^B$ and each divalent R$^{AB}$ is independently an organic group comprising from 1 to 20 carbon atoms, and further comprising a reactive conjugating functional group;
wherein the compound has at least three carbamate linkages and at least two branches.

36. A conjugate comprising a compound according to claim 1 covalently linked to one or more biologically active molecules.

37. A conjugate according to claim 36, wherein said biologically active molecules are selected from the group consisting of: oligonucleotides, peptides, polypeptides, proteins, antibodies, saccharides, polysaccharides, epitopes, mimotopes, and drugs.

* * * * *